United States Patent
Duerner et al.

(10) Patent No.: US 10,040,843 B2
(45) Date of Patent: Aug. 7, 2018

(54) INTERLEUKIN-10 FUSION PROTEINS AND USES THEREOF

(71) Applicant: Roche Glycart AG, Schlieren (CH)

(72) Inventors: Lydia Jasmin Duerner, Birmensdorf (CH); Thomas Emrich, Iffeldorf (DE); Jens Fischer, Weilheim in Oberbayern (DE); Ralf Hosse, Cham (CH); Ekkehard Moessner, Kreuzlingen (CH); Pablo Umana, Wollerau (CH); Daigen Xu, North Caldwell, NJ (US)

(73) Assignee: ROCHE GLYCART AG (CH)

(*) Notice: Subject to any disclaimer, the term of this patent is extended or adjusted under 35 U.S.C. 154(b) by 0 days.

(21) Appl. No.: 15/140,414

(22) Filed: Apr. 27, 2016

(65) Prior Publication Data

US 2016/0340413 A1  Nov. 24, 2016

Related U.S. Application Data

(63) Continuation of application No. 13/959,051, filed on Aug. 5, 2013, now Pat. No. 9,346,872.

(30) Foreign Application Priority Data

Aug. 8, 2012 (EP) ..................... 12179709

(51) Int. Cl.
*C07K 14/52* (2006.01)
*C07K 16/00* (2006.01)
*C07K 14/54* (2006.01)
*C07K 16/40* (2006.01)
*A61K 38/00* (2006.01)
*A61K 39/00* (2006.01)

(52) U.S. Cl.
CPC .......... *C07K 16/00* (2013.01); *C07K 14/5428* (2013.01); *C07K 16/40* (2013.01); *A61K 38/00* (2013.01); *A61K 39/00* (2013.01); *C07K 2317/21* (2013.01); *C07K 2317/55* (2013.01); *C07K 2317/92* (2013.01); *C07K 2319/00* (2013.01)

(58) Field of Classification Search
CPC . C07K 14/5428; C07K 2319/00; A61K 39/00
See application file for complete search history.

(56) References Cited

U.S. PATENT DOCUMENTS

2015/0218244 A1  8/2015  Emrich et al.

FOREIGN PATENT DOCUMENTS

| JP | 2008505174 A | 2/2008 |
| JP | 2011502137 A | 1/2011 |
| WO | WO 2006019447 A1 | 2/2006 |
| WO | 2007/128563 A1 | 11/2007 |
| WO | 2009/056268 A1 | 5/2009 |
| WO | 2010/005389 A1 | 1/2010 |
| WO | 2011/020783 A2 | 2/2011 |
| WO | 2012/146628 A1 | 11/2012 |

OTHER PUBLICATIONS

Naramura et al., "Mechanisms of cellular cytotoxicity mediated by a recombinant antibody-IL2 fusion protein against human melanoma cells," Immunol. Lett. 39(1):91-99 (1993).
Osenga et al., "A phase I clinical trial of the hu14.18-IL2 (EMD 273063) as a treatment for children with refractory or recurrent neuroblastoma and melanoma: a study of the Children's Oncology Group," Clin. Cancer Res. 12(6):1750-1759 (2006).
Penichet et al., "Antibody-IL-2 fusion proteins: a novel strategy for immune protection," Hum. Antibodies 8(3):106-118 (1997).
Schwager et al., "Preclinical characterization of DEKAVIL (F8-IL10), a novel clinical-stage immunocytokine which inhibits the progression of collagen-induced arthritis," Arthritis Res. Ther. 11(5):R142 (2009) (Epub Sep. 25, 2009).
Schwager et al., "The antibody-mediated targeted delivery of interleukin-10 inhibits endometriosis in a syngeneic mouse model," Hum. Reprod. 26(9):2344-2352 (2011) (Epub Jun. 24, 2011).
Trachsel et al., "A human mAb specific to oncofetal fibronectin selectively targets chronic skin inflammation in vivo," J. Invest. Dermatol. 127(4):881-886 (2007) (Epub Dec. 21, 2006).
Trachsel et al., "Antibody-mediated delivery of IL-10 inhibits the progression of established collagen-induced arthritis," Arthritis Research & Therapy, 2007, pp. 1-9, http://arthritis-research.com/content/9/1/R9.
Zheng et al., "A noncytolytic IL-10/Fc fusion protein prevents diabetes, blocks autoimmunity, and promotes suppressor phenomena in NOD mice," J. Immunol. 158(9):4507-4513 (1997).
The International Search Report by the European Patent Office, dated Oct. 24, 2013, in the corresponding PCT Application No. PCT/EP2013/066342.

*Primary Examiner* — Prema Mertz
(74) *Attorney, Agent, or Firm* — Jones Day

(57) ABSTRACT

The present invention generally relates to fusion proteins of antibodies and interleukin-10 (IL-10). In addition, the present invention relates to polynucleotides encoding such fusion proteins, and vectors and host cells comprising such polynucleotides. The invention further relates to methods for producing the fusion proteins of the invention, and to methods of using them in the treatment of disease.

22 Claims, 19 Drawing Sheets

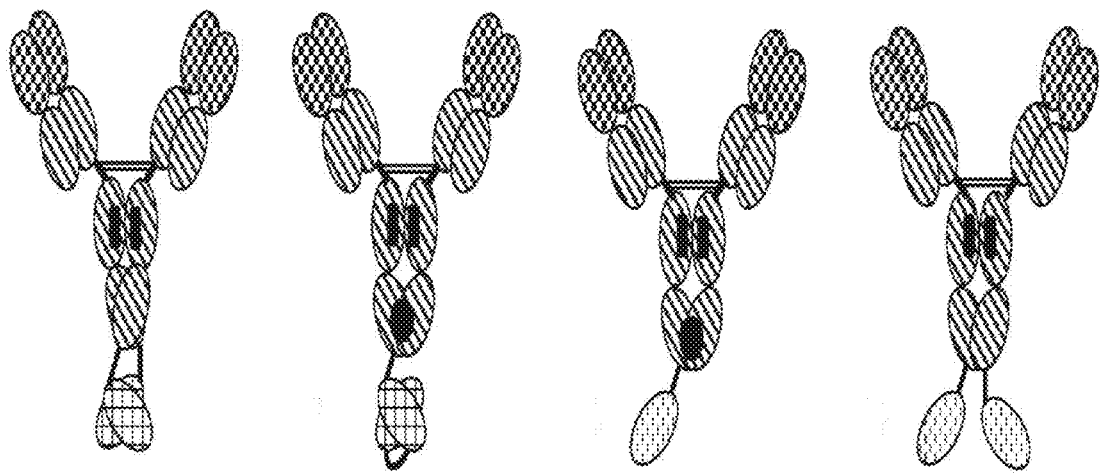
FIG. 1A     FIG. 1B     FIG. 1C     FIG. 1D
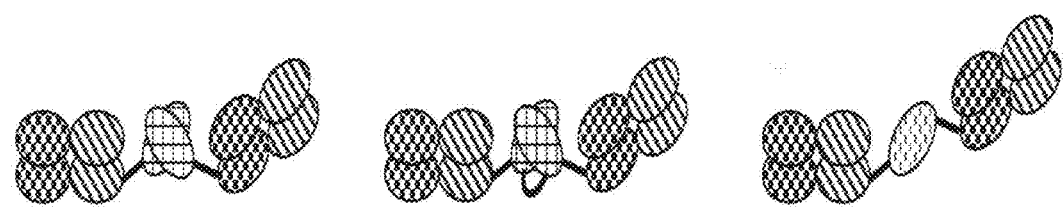
FIG. 1E     FIG. 1F     FIG. 1G
 antibody V-domain      LALA P329G mutation
 antibody C-domain      knob-into-hole modification
 IL-10      monomeric IL-10

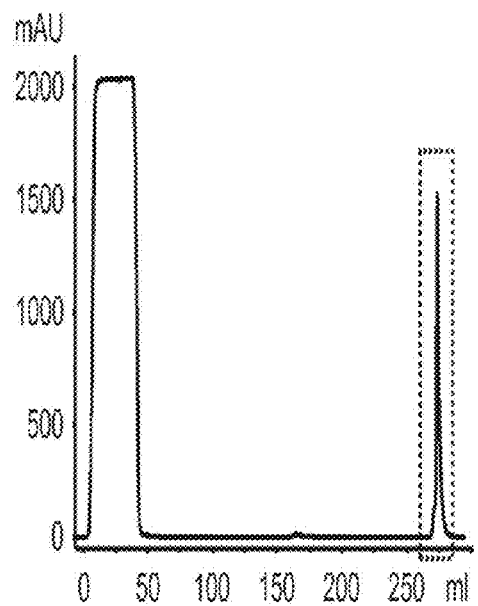
FIG. 4A
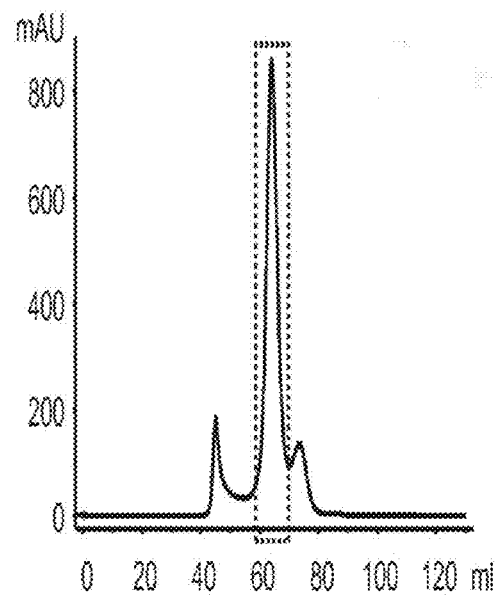
FIG. 4B
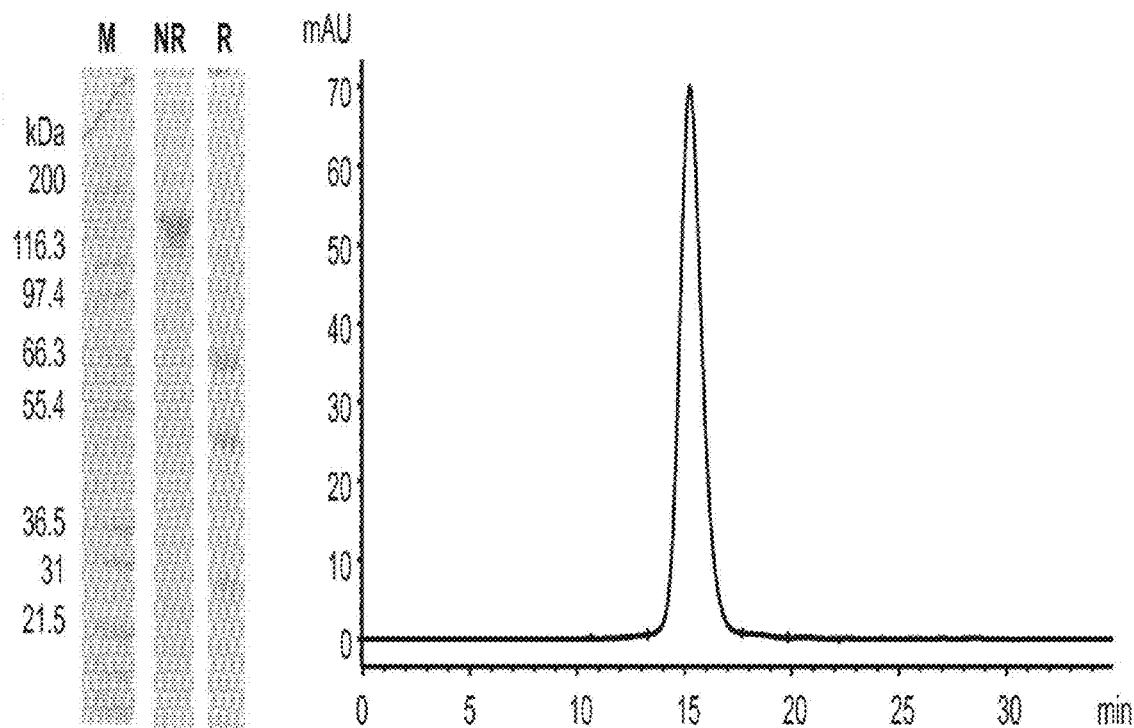
FIG. 4C
FIG. 4D

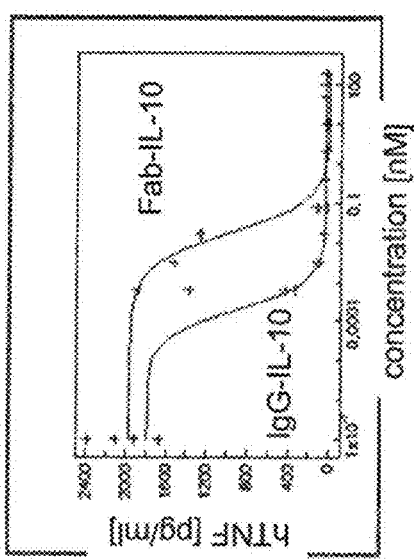
FIG. 11A
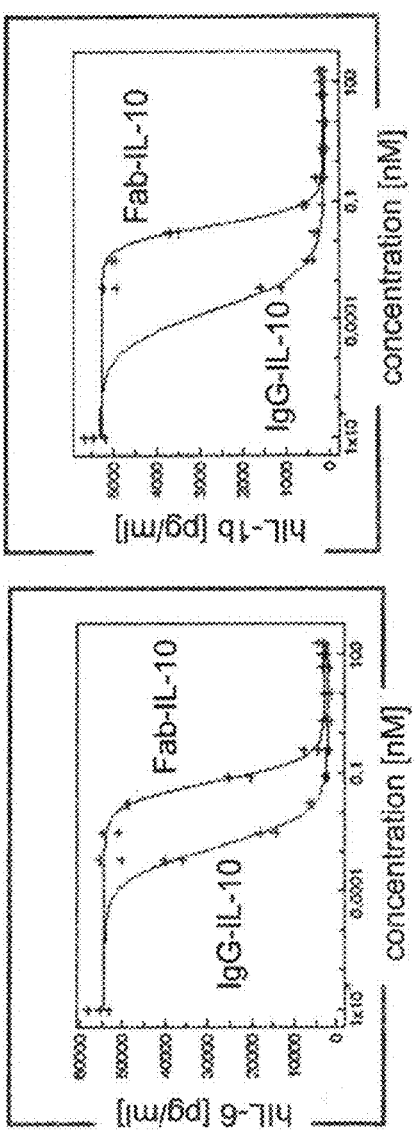
FIG. 11B
FIG. 11C
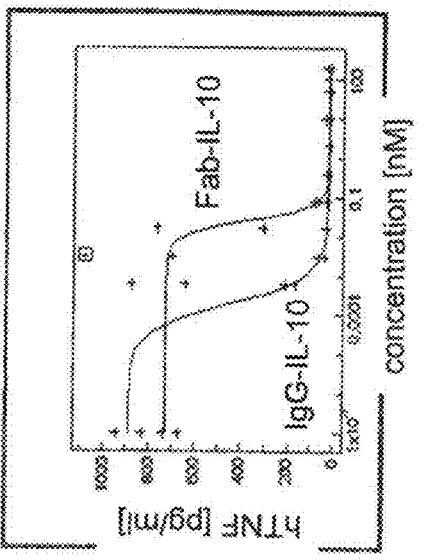
FIG. 11D
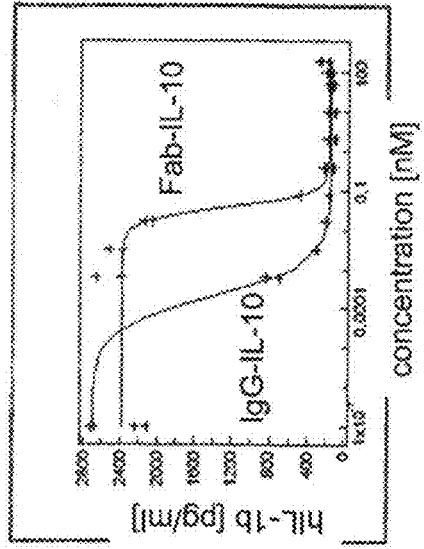
FIG. 11E
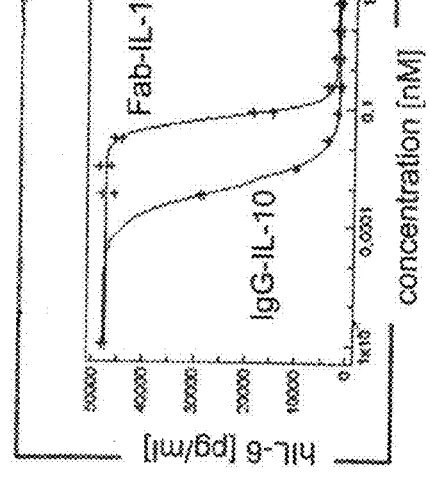
FIG. 11F

INTERLEUKIN-10 FUSION PROTEINS AND USES THEREOF

This application is a continuation of U.S. application Ser. No. 13/959,051, filed Aug. 3, 2013, which claims the benefit of European Application No. 12179709.6, filed Aug. 8, 2012, the contents of which is incorporated herein by reference in its entirety.

The content of the following submission on ASCII text file is incorporated herein by reference in its entirety: a computer readable form (CRF) of the Sequence Listing (file name: 12279-716-999_SEQ.txt, date recorded: Apr. 21, 2016, size: 164 kilobytes, and was prepared using PatentIn version 3.5).

FIELD OF THE INVENTION

The present invention generally relates to fusion proteins of antibodies and interleukin-10 (IL-10). In addition, the present invention relates to polynucleotides encoding such fusion proteins, and vectors and host cells comprising such polynucleotides. The invention further relates to methods for producing the fusion proteins of the invention, and to methods of using them in the treatment of disease.

BACKGROUND

Biological Function of IL-10

IL-10 is an α-helical cytokine that is expressed as a non-covalently linked homodimer of ~37 kDa. It plays a key role in the induction and maintenance of tolerance. Its predominantly anti-inflammatory properties have been known for a long time. IL-10 suppresses the secretion of pro-inflammatory cytokines like TNF α, IL-1, IL-6, IL-12 as well as Th1 cytokines such as IL-2 and INFγ and controls differentiation and proliferation of macrophages, B-cells and T-cells (Glocker, E. O. et al., Ann. N.Y. Acad. Sci. 1246, 102-107 (2011); Moore, K. W. et al., Annu. Rev. Immunol. 19, 683-765 (2001); de Waal Malefyt, R. et al., J. Exp. Med. 174, 915-924 (1991); Williams, L. M. et al., Immunology 113, 281-292 (2004). Moreover, it is a potent inhibitor of antigen presentation, inhibiting MHC II expression as well as upregulation of co-stimulatory molecules CD80 and CD86 (Mosser, D. M. & Yhang, X., Immunological Reviews 226, 205-218 (2008)).

Nevertheless, also immunostimulatory properties have been reported. IL-10 can costimulate B-cell activation, prolong B-cell survival, and contribute to class switching in B-cells. Moreover, it can costimulate natural killer (NK) cell proliferation and cytokine production and act as a growth factor to stimulate the proliferation of certain subsets of $CD8^+$ T cells (Mosser, D. M. & Yhang, X., Immunological Reviews 226, 205-218 (2008); Cai, G. et al., Eur. J. Immunol. 29, 2658-2665 (1999); Santin, A. D. et al., J. Virol. 74, 4729-4737 (2000); Rowbottom, A. W. et al., Immunology 98, 80-89 (1999); Groux, H. et al., J. Immunol. 160, 3188-3193 (1998)). Importantly, high doses of IL-10 (20 and 25 μg/kg, respectively) in humans can lead to an increased production of INFγ (Lauw, F. N. et al., J. Immunol. 165, 2783-2789 (2000); Tilg, H. et al., Gut 50, 191-195 (2002)).

IL-10 signals through a two-receptor complex consisting of two copies each of IL-10 receptor 1 (IL-10R1) and IL-10R2. IL-10R1 binds IL-10 with a relatively high affinity (~35-200 pM) (Moore, K. W. et al., Annu. Rev. Immunol. 19, 683-765 (2001)), and the recruitment of IL-10R2 to the receptor complex makes only a marginal contribution to ligand binding. However, the engagement of this second receptor to the complex enables signal transduction following ligand binding. Thus, the functional receptor consists of a dimer of heterodimers of IL-10R1 and IL-10R2. Most hematopoietic cells constitutively express low levels of IL-10R1, and receptor expression can often be dramatically upregulated by various stimuli. Non-hematopoietic cells, such as fibroblasts and epithelial cells, can also respond to stimuli by upregulating IL-10R1. In contrast, the IL-10R2 is expressed on most cells. The binding of IL-10 to the receptor complex activates the Janus tyrosine kinases, JAK1 and Tyk2, associated with IL-10R1 and IL-10R2, respectively, to phosphorylate the cytoplasmic tails of the receptors. This results in the recruitment of STAT3 to the IL-10R1. The homodimerization of STAT3 results in its release from the receptor and translocation of the phosphorylated STAT homodimer into the nucleus, where it binds to STAT3-binding elements in the promoters of various genes. One of these genes is IL-10 itself, which is positively regulated by STAT3. STAT3 also activates the suppressor of cytokine signaling 3 (SOCS3), which controls the quality and quantity of STAT activation. SOCS3 is induced by IL-10 and exerts negative regulatory effects on various cytokine genes (Mosser, D. M. & Yhang, X., Immunological Reviews 226, 205.218 (2008)).

Genetic linkage analyses and candidate gene sequencing revealed a direct link between mutations in IL-10R1 and IL-10R2 and early-onset enterocolitis, a form of inflammatory bowel disease (IBD) (Glocker, E. O. et al., N. Engl. J. Med. 361(21), 2033-2045 (2009)). Recent data suggest that early onset IBD can even be monogenic. Mutations in the IL-10 cytokine or its receptors lead to a loss of IL-10 function and cause severe enterocolitis in infants and small children (Glocker, E. O. et al., Ann. N.Y. Acad. Sci. 1246, 102-107 (2011)). Moreover, patients with severe forms of Crohn's disease have a defective IL-10 production in whole blood cell cultures and monocyte-derived dentritic cells (Correa, I. et al., J. Leukoc. Biol. 85(5), 896-903 (2009)). IBD affects about 1.4 million people in the United States and 2.2 million in Europe (Carter, M. J. et al., Gut 53 (Suppl. 5), V1-V16 (2004); Engel, M. A. & Neurath, M. F., J. Gastroenterol. 45, 571-583 (2010)).

Therapeutic Approaches Using IL-10

The therapeutic benefit of recombinant IL-10 in inflammatory disorders and autoimmune disease has been assessed in phase I & II clinical trials investigating safety, tolerance, pharmacokinetics, pharmacodynamics, immunological and hematological effects of single or multiple doses administered intravenously or subcutaneously in various settings on healthy volunteers as well as specific patient populations (Moore, K. W. et al., Annu. Rev. Immunol. 19, 683-765 (2001); Chernoff, A. E. et al., J. Immunol. 154, 5492-5499 (1995); Huhn, R. D. et al., Blood 87, 699-705 (1996); Huhn, R. D. et al., Clin. Pharmacol. Ther. 62, 171-180 (1997)). IL-10 was well tolerated without serious side effects at doses up to 25 μg/kg and only mild to moderate flu-like symptoms were observed in a fraction of recipients at doses up to 100 μg/kg (Moore, K. W. et al., Annu. Rev. Immunol. 19, 683-765 (2001); Chernoff, A. E. et al., J. Immunol. 154, 5492-5499 (1995)). Tendencies towards clinical improvement were most often seen in psoriasis (a compilation of clinical studies can be found in Mosser, D. M. & Yhang, X., Immunological Reviews 226, 205-218 (2008)), Crohn's disease (Van Deventer S. J. et al, Gastroenterology 113, 383-389 (1997); Fedorak, R. N. et al., Gastroenterology 119, 1473-1482 (2000); Schreiber, S. et al., Gastroenterolotgy 119, 1461-1472 (2000); Colombel J. F. et al., Gut 49, 42-46 (2001)) and rheumatoid arthritis (Keystone, E. et al., Rheum. Dis. Clin. N. Am. 24, 629-639 (1998); Mosser, D. M. & Yhang, X., Immunological Reviews 226, 205-218 (2008)).

Overall, the clinical results were unsatisfying and clinical development of recombinant human IL-10 which is identical to endogenous human IL-10 with the exception of a methionine residue at the amino terminus (ilodecakin, TENOVIL, Schering-Plough Research Institue, Kenilworth, N.J.) was discontinued due to a lack of efficacy. A recent systematic review of the efficacy and tolerability of recombinant human IL-10 for induction of remission in Crohn's disease found no statistically significant differences between IL-10 and placebo for complete or clinical remission and stated that patients treated with IL-10 were significantly more likely to withdraw from the studies due to adverse events relative to placebo (Buruiana, F. E. et al., Cochrane Database Syst. Rev. 11, CD005109 (2010)) For Crohn's disease, several reasons for these unsatisfying results have been discussed (Herfarth, H. & Schölmerich, J., Gut 50, 146-147 (2002)): 1) local cytokine concentrations in the gut that were too low to mediate a sustained anti-inflammatory effect, 2) dose escalation of systemically administered IL-10 was limited due to side effects, and 3) the immunostimulatory properties of IL-10 on B cells and on INFγ production by $CD4^+$, $CD8^+$, and/or natural killer cells counterbalance its immunosuppressive properties (Asadullah, K. et al., Pharmacol. Rev. 55, 241-269 (2003); Tilg, H. et al., Gut 50, 191-195 (2002); Lauw, F. N. et al., J. Immunol. 165, 2783-2789 (2000)).

IL-10 exhibits a very short plasma half-life due to its small size of ~37 kDa which leads to rapid kidney clearance. In fact, its half life in the systemic compartment is 2.5 h which limits the mucosal bioavailability (Braat, H. et al., Expert Opin. Biol. Ther. 3(5), 725-731 (2003). In order to improve circulation time, exposure, efficacy and to reduce renal uptake, several publications report the PEGylation of this cytokine (Mattos, A. et al., J. Control Release 162, 84-91 (2012); Mumm, J. B. et al., Cancer Cell 20(6), 781-796 (2011); Alvarez, H. M. et al., Drug Metab. Dispos. 40(2), 360-373 (2012)). Nevertheless, the longer systemic half-life of PEGylated non-targeted IL-10 can exacerbate known adverse events of this molecule.

It has become clear that systemic treatment using recombinant human IL-10 is not sufficiently effective and that the focus has to be on local delivery of the cytokine. There are several ways to achieve this goal: 1) IL-10 gene therapy of immune cells, 2) genetically modified, non-pathogenic, IL-10 expression bacteria and 3) antibody-IL-10 fusion proteins in order to target the cytokine to and to accumulate the cytokine in inflamed tissues.

IL-10 gene therapy of immune cells has demonstrated effectiveness in experimental colitis but clinical trials are hampered by concerns over the safety of this approach for non-lethal diseases (Braat, H. et al., Expert Opin. Biol. Ther. 3(5), 725-731 (2003)). Transgenic bacteria (*Lactococcus lactis*) expressing IL-10 represent an alternative route of delivery and the outcome of a phase I trial in Crohn's disease was published claiming to avoid systemic side effects due to local delivery into the mucosal compartment and to be biologically contained (Braat, H. et al., Gastroenterol. Hepatol. 4, 754-759 (2006); Steidler, L. et al., Science 289, 1352-1355 (2000)). A phase IIa randomized placebo-controlled double-blind multi-center dose escalation study to evaluate the safety, tolerability, pharmacodynamics and efficacy of genetically modified *Lactococcus lactis* secreting human IL-10 (AG011, ActoGeniX) in patients with moderately active ulcerative colitis was well-tolerated and safe. However, there was no significant improvement of mucosal inflammation, as measured by the modified Baron score, or clinical symptoms in patients receiving AG011 compared with placebo (Vermeire, S. et al., abstract 46 presented at the Digestive Disease Week Annual Meeting in New Orleans 2 May 2010).

Antibody-cytokine fusion proteins, also called immunocytokines, offer several advantages in terms of drug delivery and the format of the drug itself. Local delivery of cytokines, e.g. IL-10, is achieved by fusion to antibodies or fragments thereof specific for suitable disease markers. Thus, systemic side effects can be reduced and local accumulation and retention of the compound at the site of inflammation can be achieved. Moreover, depending on the fusion format and antibody or antibody fragment used, properties like plasma half-life, stability and developability can be improved. Although an already established approach in oncology, it was only recently adapted in order to treat inflammatory disorders and autoimmunity. Several cytokines (IL-10 amongst others) and a photosensitizer were targeted to psoriatic lesions by fusion to a scFv antibody fragment specific for the extra domain B of fibronectin (Trachsel, E. et al., J. Invest. Dermatol. 127(4), 881-886 (2007). Moreover, antibody fragments specific for the extra domain A of fibronectin (F8, DEKAVIL, Philogen SpA)-IL-10 fusion proteins were used preclinically to inhibit the progression of established collagen-induced arthritis (Trachsel, E. et al., Arthritis Res. Ther. 9(1), R 9 (2007); Schwager, K. et al., Arthritis Res. Ther. 11(5), R142 (2009)) and entered clinical trials. Recently, the same F8-IL-10 fusion protein was used for targeting endometriotic lesions in a syngeneic mouse model and reduced the average lesion sizes compared to the saline control group (Schwager, K. et al., Hum. Reprod. 26(9), 2344-2352 (2011)).

The IgG-IL-10 fusion proteins of this invention have several advantages over the known antibody fragment-based (e.g. scFv, diabody, Fab) IL-10 fusion proteins, including improved produceability, stability, serum half-life and, surprisingly, significantly increased biological activity upon binding to target antigen.

SUMMARY OF THE INVENTION

In one aspect, the invention provides a fusion protein of an IgG-class antibody and an IL-10 molecule, wherein the fusion protein comprises two identical heavy chain polypeptides and two identical light chain polypeptides. In one embodiment, each of said heavy chain polypeptides comprises an IgG-class antibody heavy chain and an IL-10 monomer. In a more specific embodiment, said IL-10 monomer is fused at its N-terminus to the C-terminus of said IgG-class antibody heavy chain, optionally through a peptide linker. In one embodiment, said heavy chain polypeptides each essentially consist of an IgG-class antibody heavy chain, an IL-10 monomer and optionally a peptide linker. In one embodiment, each of said light chain polypeptides comprises an IgG-class antibody light chain. In one embodiment, said light chain polypeptides each essentially consist of an IgG-class antibody light chain.

In some embodiments, said IL-10 monomer is a native IL-10 monomer, particularly a native human IL-10 monomer. In a specific embodiment, said IL-10 monomer comprises the polypeptide sequence of SEQ ID NO: 1. In one embodiment, said IL-10 monomers comprised in said heavy chain polypeptides form a functional homodimeric IL-10 molecule.

In other embodiments, said IL-10 monomer is a modified IL-10 monomer, particularly a modified human IL-10 monomer. In one embodiment, said modified IL-10 monomer is stable at pH 7.0, 37° C. in monomeric form. In one embodiment, said modified IL-10 monomer has improved stability at pH 7.0, 37° C. as compared to a native IL-10 monomer. In a specific embodiment, said IL-10 monomer comprises the polypeptide sequence of SEQ ID NO: 5. In one embodiment, said IL-10 monomers comprised in said heavy chain polypeptides do not homodimerize with each other.

In one embodiment, said IgG-class antibody comprises a modification reducing binding affinity of the antibody to an Fc receptor, as compared to a corresponding IgG-class antibody without said modification. In a specific embodiment, said Fc receptor is an Fcγ receptor, particularly a human Fcγ receptor. In one embodiment, said Fc receptor is an activating Fc receptor, particularly an activating Fcγ receptor. In a specific embodiment, said Fc receptor is selected from the group of FcγRIIIa (CD16a), FcγRI (CD64), FcγRIIa (CD32) and FcαRI (CD89). In an even more specific embodiment, said Fc receptor is FcγRIIIa, particularly human FcγRIIIa. In one embodiment, said modification reduces effector function of the IgG-class antibody. In a specific embodiment, said effector function is antibody-dependent cell-mediated cytotoxicity (ADCC). In one embodiment, said modification is in the Fc region, particularly the CH2 region, of said IgG-class antibody. In one embodiment, said IgG-class antibody comprises an amino acid substitution at position 329 (EU numbering) of the antibody heavy chains. In a specific embodiment, said amino acid substitution is P329G. In one embodiment, said IgG-class antibody comprises amino acid substitutions at positions 234 and 235 (EU numbering) of the antibody heavy chains. In a specific embodiment, said amino acid substitutions are L234A and L235A (LALA). In a particular embodiment, said IgG-class antibody comprises amino acid substitutions L234A, L235A and P329G (EU numbering) in the antibody heavy chains.

In one embodiment, said IgG-class antibody is an IgG$_1$-subclass antibody. In one embodiment, said IgG-class antibody is a full-length antibody. In one embodiment, said IgG-class antibody is a human antibody. In one embodiment, said IgG-class antibody is a monoclonal antibody.

In one embodiment, said IgG-class antibody is capable of specific binding to Fibroblast Activation Protein (FAP). In a specific embodiment, the fusion protein is capable of binding to FAP with an affinity constant ($K_D$) of smaller than 1 nM, particularly smaller than 100 pM, when measured by Surface Plasmon Resonance (SPR) at 25° C. In one embodiment, said FAP is human, mouse and/or cynomolgus FAP. In a specific embodiment, said IgG-class antibody comprises the heavy chain CDR (HCDR) 1 of SEQ ID NO: 37, the HCDR 2 of SEQ ID NO: 41, the HCDR 3 of SEQ ID NO: 49, the light chain CDR (LCDR) 1 of SEQ ID NO: 53, the LCDR 2 of SEQ ID NO: 57 and the LCDR 3 of SEQ ID NO: 61. In an even more specific embodiment, said IgG-class antibody comprises the heavy chain variable region (VH) of SEQ ID NO: 63 and the light chain variable region (VL) of SEQ ID NO: 65. In another, particular, specific embodiment, said IgG-class antibody comprises the HCDR 1 of SEQ ID NO: 37, the HCDR 2 of SEQ ID NO: 43, the HCDR 3 of SEQ ID NO: 47, the LCDR 1 of SEQ ID NO: 51, the LCDR 2 of SEQ ID NO: 55 and the LCDR 3 of SEQ ID NO: 59. In an even more specific embodiment, said IgG-class antibody comprises the VH of SEQ ID NO: 67 and the VL of SEQ ID NO: 69.

In one embodiment, the fusion protein is capable of binding to IL-10 receptor-1 (IL-10R1) with an affinity constant ($K_D$) of smaller than 1 nM, particularly smaller than 100 pM, when measured by SPR at 25° C. In a specific embodiment, said IL-10R1 is human IL-10R1. In one embodiment, said affinity constant ($K_D$) for binding to IL-10R1 is about equal or greater than said affinity constant ($K_D$) for binding to FAP, when measured by SPR at 25° C. In a specific embodiment, said $K_D$ for binding to IL-10R1 is greater than about half of said $K_D$ for binding to FAP.

In a particular embodiment, the invention provides a fusion protein of an IgG-class antibody and an IL-10 molecule, wherein the fusion protein comprises two identical heavy chain polypeptides and two identical light chain polypeptides; and wherein
(i) said IgG-class antibody comprises the heavy chain CDR (HCDR) 1 of SEQ ID NO: 37, the HCDR 2 of SEQ ID NO: 43, the HCDR 3 of SEQ ID NO: 47, the light chain CDR (LCDR) 1 of SEQ ID NO: 51, the LCDR 2 of SEQ ID NO: 55 and the LCDR 3 of SEQ ID NO: 59, or comprises the heavy chain variable region (VH) of SEQ ID NO: 67 and the light chain variable region (VL) of SEQ ID NO: 69;
(ii) said IgG-class antibody comprises amino acid substitutions L234A, L235A and P329G (EU numbering) in the antibody heavy chains;
(iii) said IL-10 molecule comprises the sequence of SEQ ID NO: 1; and
(iv) said heavy chain polypeptides each comprise an IgG-class antibody heavy chain and an IL-10 monomer fused at its N-terminus to the C-terminus of said IgG-class antibody heavy chain through a peptide linker.

In another embodiment, the invention provides a fusion protein of an IgG-class antibody and an IL-10 molecule, wherein the fusion protein comprises two identical heavy chain polypeptides and two identical light chain polypeptides; and wherein
(i) said IgG-class antibody comprises the heavy chain CDR (HCDR) 1 of SEQ ID NO: 37, the HCDR 2 of SEQ ID NO: 41, the HCDR 3 of SEQ ID NO: 49, the light chain CDR (LCDR) 1 of SEQ ID NO: 53, the LCDR 2 of SEQ ID NO: 57 and the LCDR 3 of SEQ ID NO: 61, or comprises the heavy chain variable region (VH) of SEQ ID NO: 63 and the light chain variable region (VL) of SEQ ID NO: 65;
(ii) said IgG-class antibody comprises amino acid substitutions L234A, L235A and P329G (EU numbering) in the antibody heavy chains;
(iii) said IL-10 molecule comprises the sequence of SEQ ID NO: 1; and
(iv) said heavy chain polypeptides each comprise an IgG-class antibody heavy chain and an IL-10 monomer fused at its N-terminus to the C-terminus of said IgG-class antibody heavy chain through a peptide linker.

The invention further provides a polynucleotide encoding the fusion protein of the invention. Further provided is a vector, particularly an expression vector, comprising the polynucleotide of the invention. In another aspect, the invention provides a host cell comprising the polynucleotide or the vector of the invention. The invention also provides a method for producing a fusion protein of the invention, comprising the steps of (i) culturing the host cell of the invention under conditions suitable for expression of the fusion protein, and (i) recovering the fusion protein. Also provided is a fusion protein of an IgG-class antibody and an IL-10 molecule produced by said method.

In one aspect, the invention provides a pharmaceutical composition comprising the fusion protein of the invention and a pharmaceutically acceptable carrier. The fusion protein or the pharmaceutical composition of the invention is also provided for use as a medicament, and for use in the treatment or prophylaxis of an inflammatory disease, specifically inflammatory bowel disease or rheumatoid arthritis, most specifically inflammatory bowel disease. Further provided is the use of the fusion protein of the invention for the manufacture of a medicament for the treatment of a disease in an individual in need thereof, and a method of treating a disease in an individual, comprising administering to said individual a therapeutically effective amount of a composition comprising the fusion protein of the invention in a pharmaceutically acceptable form. In one embodiment, said disease is an inflammatory disease. In a more specific embodiment, said inflammatory disease is inflammatory bowel disease or rheumatoid arthritis. In an even more specific embodiment, said inflammatory disease is inflammatory bowel disease. In one embodiment, said individual is a mammal, particularly a human.

BRIEF DESCRIPTION OF THE DRAWINGS

FIGS. 1A-1G Schematic representation of various antibody-IL-10 fusion formats. FIGS. 1A-1D show formats based on an IgG antibody, FIGS. 1E-1G show formats based on Fab fragments. (FIG. 1A) "IgG-IL-10", human IgG (with engineered Fc-region to avoid effector functions, e.g. by amino acid substitutions L234A L235A (LALA) P329G) with one IL-10 molecule (wild type human IL-10 cytokine sequence) fused to C-terminus of each IgG heavy chain (IL-10 molecules on both heavy chains dimerize within the same IgG molecule). Connector between heavy chain and IL-10: e.g. $(G_4S)_4$ 20-mer. (FIG. 1B) "IgG-single chain (sc) IL-10", human IgG (with engineered Fc-region to avoid effector functions and combination of one "knob" heavy chain and one "hole" heavy chain to facilitate heterodimerization of the two) with single chain IL-10 dimer (scIL-10) fused to C-terminus of one of the IgG heavy chains. Connector between the heavy chain and single chain IL-10: e.g. $(G_4S)_3$ 15-mer. (FIG. 1C) "IgG-IL-10M1", human IgG (with engineered Fc-part to avoid effector functions and combination of one "knob" heavy chain and one "hole" heavy chain to facilitate heterodimerization of the two) with engineered monomeric IL-10 molecule fused to C-terminus of one of the IgG heavy chains. Connector between the heavy chain and monomeric IL-10: e.g. $(G_4S)_3$ 15-mer. (FIG. 1D) "IgG-(IL-10M1)$_2$", human IgG (with engineered Fc-part to avoid effector functions) with one IL-10 monomer fused to the C-terminus of each IgG heavy chain (monomeric IL-10 molecules on either heavy chain do not dimerize). Connector between the heavy chain and IL-10: e.g. $(G_4S)_3$ 15-mer linker. (FIG. 1E) "Fab-IL-10", Fab fragment with one IL-10 molecule (wild type human IL-10 cytokine sequence) fused to C-terminus of the Fab heavy chain (two of these fusions form a homodimeric active molecule by dimerization via IL-10 portion). Connector between the heavy chain and IL-10: e.g. $(G_4S)_3$ 15-mer. (FIG. 1F) "Fab-scIL-10-Fab", tandem Fab fragments intermitted by a single chain IL-10 dimer (i.e. two IL-10 molecules have been linked by e.g. a $(G_4S)_4$ 20-mer linker and inserted between the C-terminus of the first Fab heavy chain (HC1) and the N-terminus of the second Fab heavy chain (HC2), resulting in a single peptide chain comprising HC1-IL-10-IL-10-HC2). Two light chains (which can be identical to the ones used for the other constructs) pair with these two heavy chains. (FIG. 1G) "Fab-IL-10M1-Fab", tandem Fab fragments intermitted by an engineered monomeric IL-10 molecule. Apart from the monomeric IL-10 portion, this format is identical to (FIG. 1F).

(FIG. 2A) Elution profile of the protein A purification step. (FIG. 2B) Elution profile of the size exclusion chromatography step. (FIG. 2C) Analytical SDS-PAGE (reduced (R): NuPAGE Novex Bis-Tris Mini Gel, Invitrogen, MOPS running buffer, non-reduced (NR): NuPAGE Tris-Acetate, Invitrogen, Tris-Acetate running buffer) of the final product. M: size marker (FIG. 2D) Analytical size exclusion chromatography on a Superdex 200 column of the final product. Monomer content 99.8%.

(FIG. 3A) Elution profile of the protein A purification step. (FIG. 3B) Elution profile of the size exclusion chromatography step (desired product indicated by dotted square). (FIG. 3C) Analytical SDS-PAGE (reduced (R): NuPAGE Novex Bis-Tris Mini Gel, Invitrogen, MOPS running buffer, non-reduced (NR): NuPAGE Tris-Acetate, Invitrogen, Tris-Acetate running buffer) of the final product; additional lower MW-band on non-reduced gel may represent a half-molecule consisting of one heavy chain and light chain. (FIG. 3D) Analytical size exclusion chromatography on a TSKgel G3000 SW XL column of the final product. Monomer content 80.6%.

FIGS. 4A-4D Purification of FAP-targeted 4G8-based IgG-IL-10M1 construct (see SEQ ID NOs 7, 13 and 15). (FIG. 4A) Elution profile of the protein A purification step. (FIG. 4B) Elution profile of the size exclusion chromatography step. (FIG. 4C) Analytical SDS-PAGE (reduced (R): NuPAGE Novex Bis-Tris Mini Gel, Invitrogen, MOPS running buffer, non-reduced (NR): NuPAGE Tris-Acetate, Invitrogen, Tris-Acetate running buffer) of the final product. (FIG. 4D) Analytical size exclusion chromatography on a Superdex 200 column of the final product. Monomer content 98.2%.

(FIG. 5A) Elution profile of the protein A purification step. (FIG. 5B) Elution profile of the size exclusion chromatography step. (FIG. 5C) LabChip GX (Caliper) analysis of the final product. (FIG. 5D) Analytical size exclusion chromatography on a TKSgel G3000 SW XL column of the final product. Monomer content 100%.

(FIG. 6A) Elution profile of the protein A purification step. (FIG. 6B) Elution profile of the size exclusion chromatography step. (FIG. 6C) Analytical SDS-PAGE (reduced (R): NuPAGE Novex Bis-Tris Mini Gel, Invitrogen, MOPS running buffer, non-reduced (NR): NuPAGE Tris-Acetate, Invitrogen, Tris-Acetate running buffer) of the final product. (FIG. 6D) Analytical size exclusion chromatography on a Superdex 200 column of the final product. Monomer content 92.9%.

(FIG. 7A) Elution profile of the protein A purification step. (FIG. 7B) Elution profile of the size exclusion chromatography step. (FIG. 7C) Analytical SDS-PAGE (reduced (R): NuPAGE Novex Bis-Tris Mini Gel, Invitrogen, MOPS running buffer, non-reduced (NR): NuPAGE Tris-Acetate, Invitrogen, Tris-Acetate running buffer) of the final product. (FIG. 7D) Analytical size exclusion chromatography on a Superdex 200 column of the final product. Monomer content 100%.

(FIG. 8A) Elution profile of the protein A purification step. (FIG. 8B) Elution profile of the size exclusion chromatography step. (FIG. 8C) Analytical SDS-PAGE (reduced (R): NuPAGE Novex Bis-Tris Mini Gel, Invitrogen, MOPS running buffer, non-reduced (NR): NuPAGE Tris-Acetate, Invitrogen, Tris-Acetate running buffer) of the final product. (FIG. 8D) Analytical size exclusion chromatography on a Superdex 200 column of the final product. Monomer content 100%.

(FIG. 9A) Covalent immobilization of anti-penta His IgG (capture agent) on GLM chip by amine coupling followed by capture of FAP (ligand) and subsequent injection of anti-FAP antibody-IL-10 fusion constructs (analyte). (FIG. 9B) Immobilization of biotinylated human IL-10R1 (ligand) on neutravidin-derivatized sensor chip (NLC) followed by injection of anti-FAP antibody-IL-10 fusion constructs (analyte).

(FIGS. 10A-10C) 4G8 Fab-IL-10 (see SEQ ID NOs 7 and 19) or 4G8 IgG-IL-10 (see SEQ ID NOs 7 and 9) were immobilized on cell culture plates coated with recombinant human FAP before monocytes and 100 ng/ml LPS as stimulus were added for 24 h. Concentrations of IL-6 (FIG. 10A), IL-1β (FIG. 10B) and TNFα (FIG. 10C) in supernatant were measured subsequently (n=2). (FIGS. 10D-10F) Monocytes were incubated with 0-200 nM 4G8 Fab-IL-10 or 4G8 IgG-IL-10 (in solution) and 100 ng/ml LPS as stimulus for 24 h. Concentrations of IL-6 (FIG. 10D), IL-1β (FIG. 10E) and TNFα (FIG. 10F) in supernatant were measured subsequently (n=2).

FIGS. 11A-11L Reproduction of the results shown in FIGS. 1A-1G using two different blood donors. (FIGS. 11A-11F) 4G8 Fab-IL-10 or 4G8 IgG-IL-10 were immobilized on cell culture plates coated with recombinant human FAP before monocytes and 100 ng/ml LPS as stimulus were added for 24 h. Concentrations of IL-6 (FIGS. 11A and 11D), IL-1β (FIGS. 11B and 11E) and TNFα (FIGS. 11C and 11F) in supernatant were measured subsequently (each row (FIGS. 11A-11C and FIGS. 11D-11F) represents a blood donor). (FIGS. 11G-11L) Monocytes were incubated with 0-200 nM 4G8 Fab-IL-10, 4G8 IgG-IL-10 or wild-type human IL-10 (in solution) and 100 ng/ml LPS as stimulus for 24 h. Concentrations of IL-6 (FIGS. 11G and 11J), IL-1β (FIGS. 11H and 11K) and TNFα (FIGS. 11I and 11L) in supernatant were measured subsequently (each row (FIGS. 11G-11I and FIGS. 11J-11L) represents a blood donor).

(FIGS. 12A-12C) 4G8 Fab-IL-10, 4G8 IgG-IL-10 or corresponding untargeted constructs were immobilized on cell culture plates coated with recombinant human FAP before monocytes and 100 ng/ml LPS as stimulus were added for 24 h. Concentrations of IL-6 in supernatant were measured subsequently. (FIGS. 12D-12F) Monocytes were incubated with 0-200 nM 4G8 Fab-IL-10, 4G8 IgG-IL-10, corresponding untargeted constructs or wild-type human IL-10 (in solution) and 100 ng/ml LPS as stimulus for 24 h. Concentrations of IL-6 in supernatant were measured subsequently.

(FIG. 15A) 4B9 Fab-IL-10 (see SEQ ID NOs 25 and 31) or 4B9 IgG-IL-10 (see SEQ ID NOs 25 and 27) constructs were immobilized on cell culture plates coated with recombinant human FAP before monocytes and 100 ng/ml LPS as stimulus were added for 24 h. Concentrations of IL-6 in supernatant were measured subsequently. (FIG. 15B) Monocytes were incubated with 0-200 nM 4B9 Fab-IL-10 or 4B9 IgG-IL-10 constructs (in solution) and 100 ng/ml LPS as stimulus for 24 h. Concentrations of IL-6 in supernatant were measured subsequently.

DETAILED DESCRIPTION OF THE INVENTION

Definitions

Figure 2A:
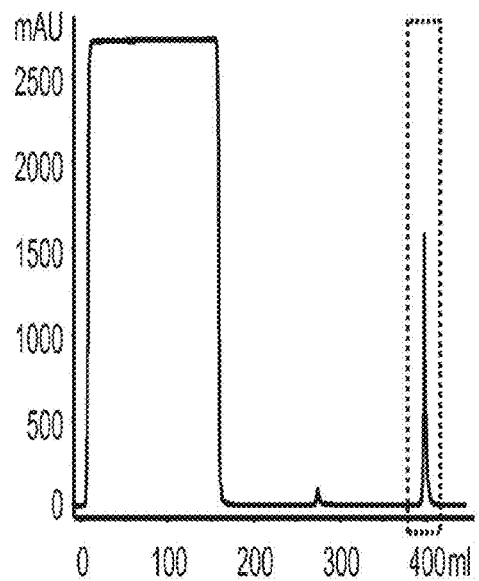
FIGS. 2A-2D Purification of FAP-targeted 4B9-based IgG-IL-10 construct (see SEQ ID NOs 25 and 27).
Figure 2B:
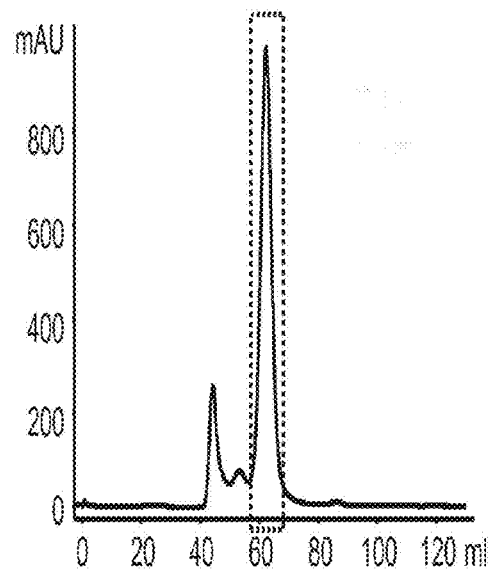
Figure 2C:
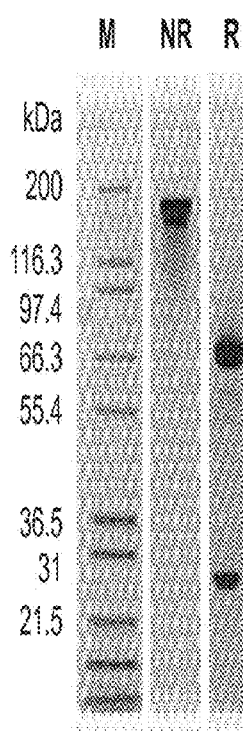
Figure 2D:
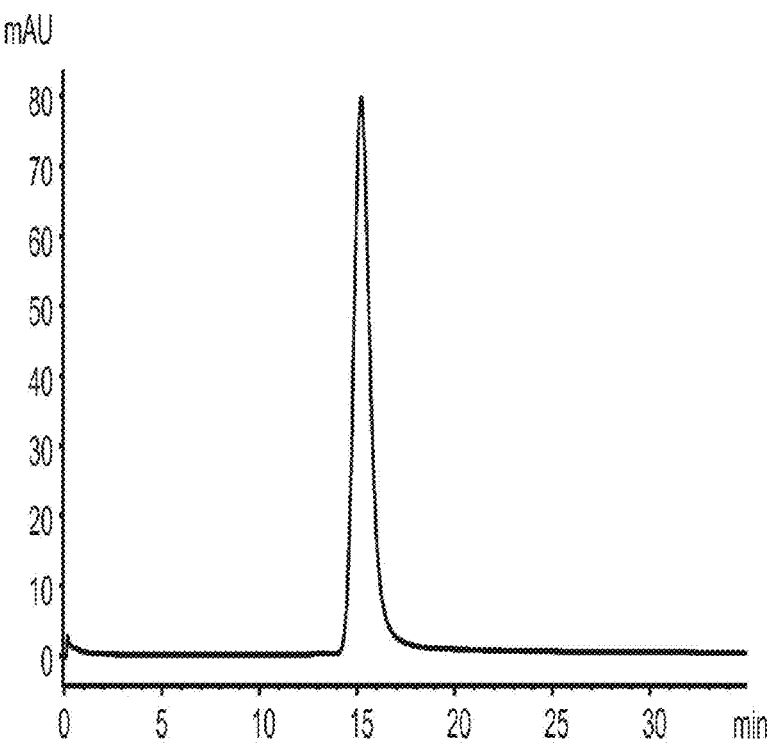
Figure 3A:
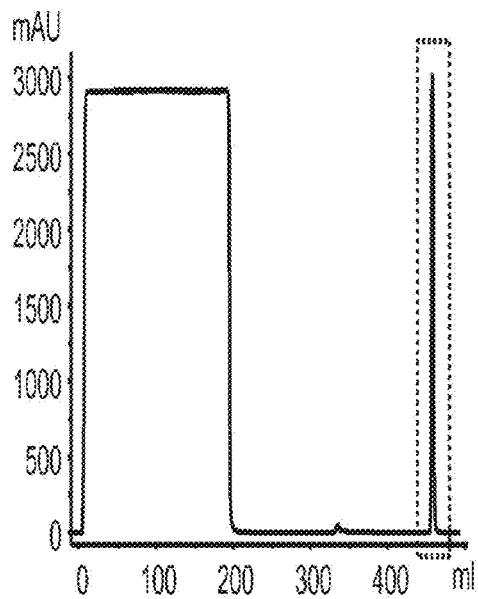
FIGS. 3A-3D Purification of FAP-targeted 4G8-based IgG-scIL-10 construct (see SEQ ID NOs 7, 11 and 13).
Figure 3B:
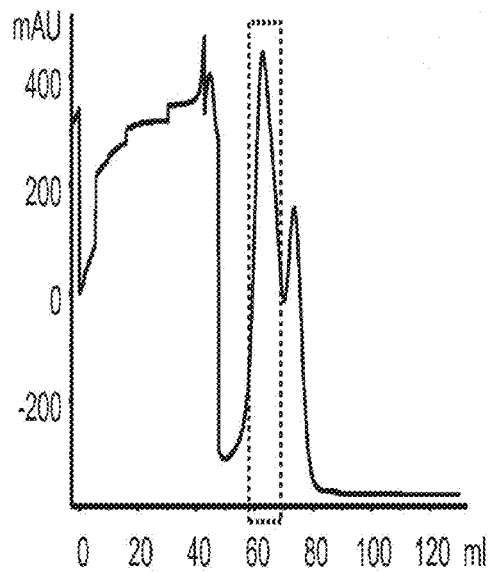
Figure 3C:
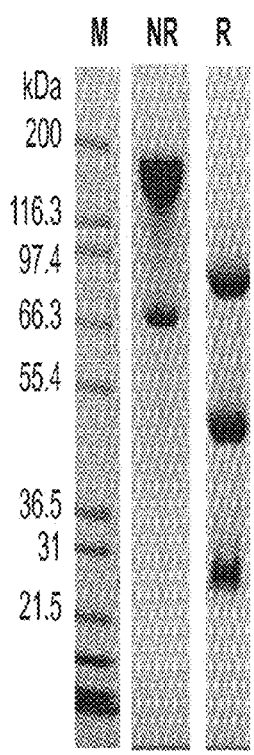
Figure 3D:
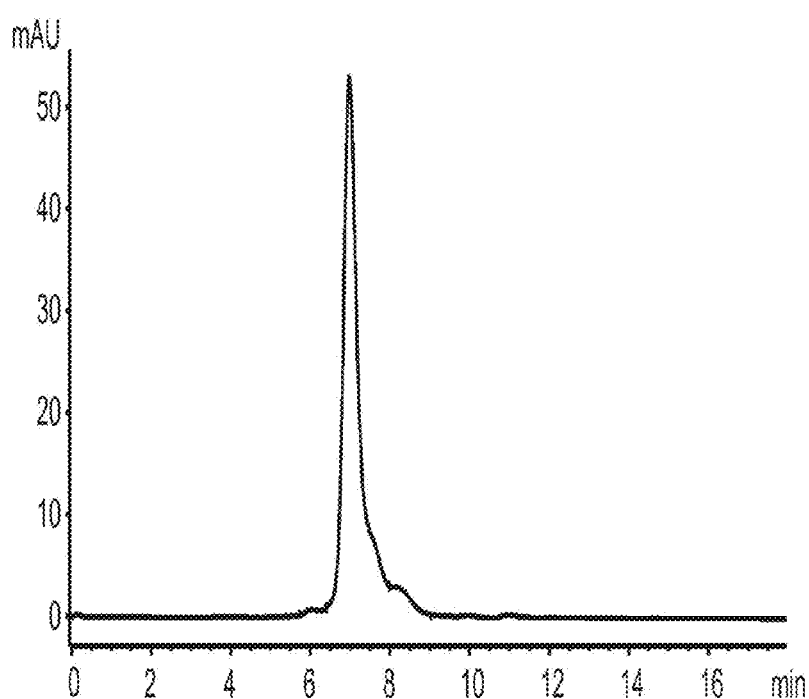
Figure 5A:
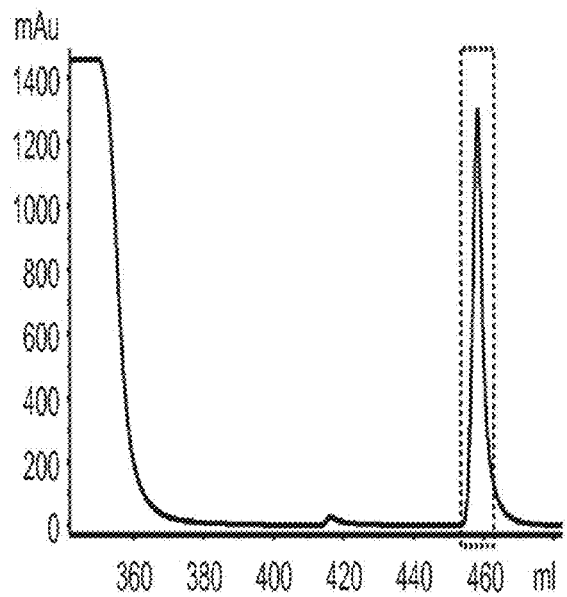
FIGS. 5A-5D Purification of FAP-targeted 4B9-based IgG-(IL-10M1)2 construct (see SEQ ID NOs 25 and 29).
Figure 5B:
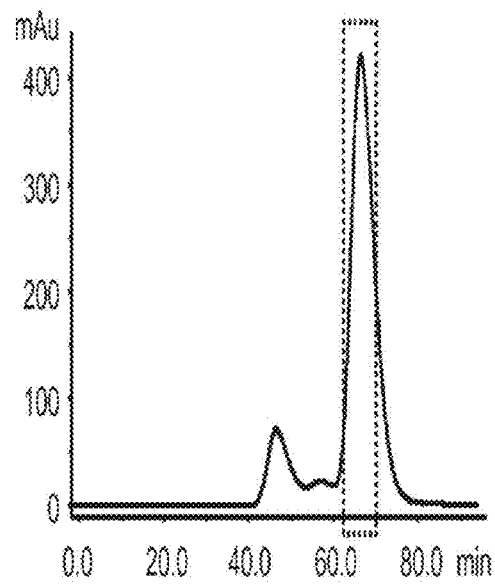
Figure 5C:
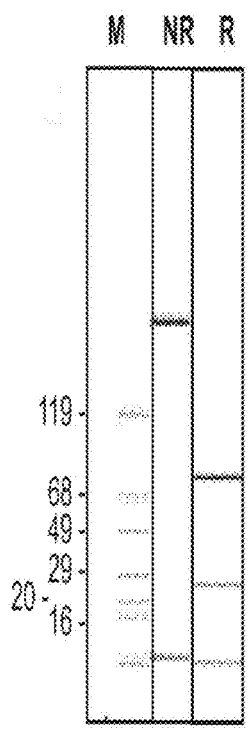
Figure 5D:
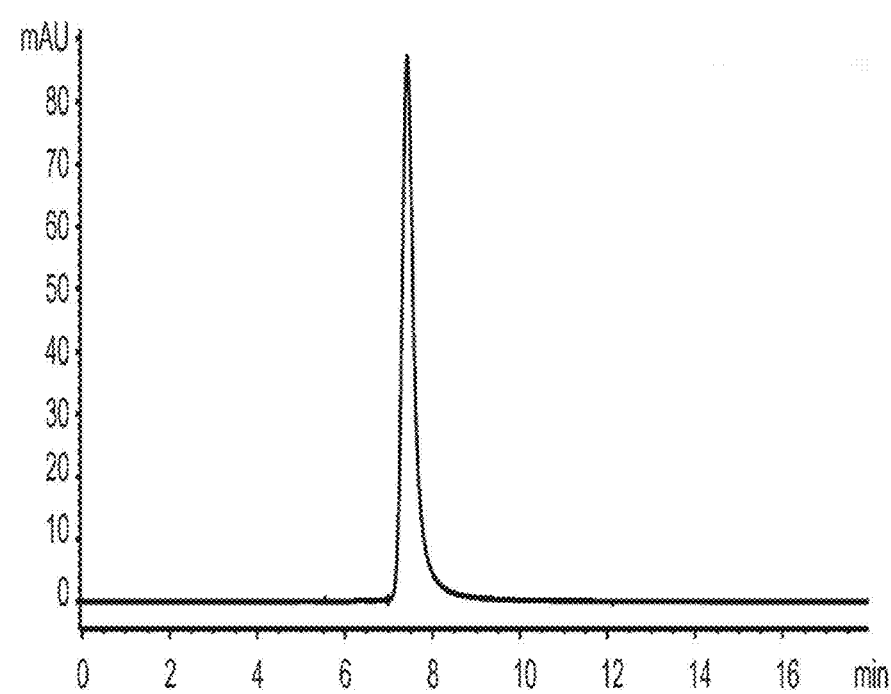

Terms are used herein as generally used in the art, unless otherwise defined in the following.

"Fibroblast Activation Protein", abbreviated as FAP, also known as Seprase (EC 3.4.21), refers to any native FAP from any vertebrate source, including mammals such as primates (e.g. humans), non-human primates (e.g. cynomolgus monkeys) and rodents (e.g. mice and rats), unless otherwise indicated. The term encompasses "full-length," unprocessed FAP as well as any form of FAP that results from processing in the cell. The term also encompasses naturally occurring variants of FAP, e.g., splice variants or allelic variants. In one embodiment, the antibody of the invention is capable of specific binding to human, mouse and/or cynomolgus FAP. The amino acid sequence of human FAP is shown in UniProt (www.uniprot.org) accession no. Q12884 (version 128), or NCBI (www.ncbi.nlm.nih.gov/) RefSeq NP_004451.2. The extracellular domain (ECD) of human FAP extends from amino acid position 26 to 760. The amino acid and nucleotide sequences of a His-tagged human FAP ECD is shown in SEQ ID NOs 81 and 82, respectively. The amino acid sequence of mouse FAP is shown in UniProt accession no. P97321 (version 107), or NCBI RefSeq NP_032012.1. The extracellular domain (ECD) of mouse FAP extends from amino acid position 26 to 761. SEQ ID NOs 83 and 84 show the amino acid and nucleotide sequences, respectively, of a His-tagged mouse FAP ECD. SEQ ID NOs 85 and 86 show the amino acid and nucleotide sequences, respectively, of a His-tagged cynomolgus FAP ECD.

By "human IL-10R1" is meant the protein described in UniProt accession no. Q13651 (version 115), particularly the extracellular domain of said protein which extends from amino acid position 22 to amino acid position 235 of the full sequence. SEQ ID NOs 87 and 88 show the amino acid and nucleotide sequences, respectively, of a human IL-10R1 ECD fused to a human Fc region.

As used herein, the term "fusion protein" refers to a fusion polypeptide molecule comprising an antibody and an IL-10 molecule, wherein the components of the fusion protein are linked to each other by peptide-bonds, either directly or through peptide linkers. For clarity, the individual peptide chains of the antibody component of the fusion protein may be linked non-covalently, e.g. by disulfide bonds.

"Fused" refers to components that are linked by peptide bonds, either directly or via one or more peptide linkers.

By "specific binding" is meant that the binding is selective for the antigen and can be discriminated from unwanted or non-specific interactions. The ability of an antibody to bind to a specific antigen can be measured either through an enzyme-linked immunosorbent assay (ELISA) or other techniques familiar to one of skill in the art, e.g. Surface Plasmon Resonance (SPR) technique (analyzed on a BIAcore instrument) (Liljeblad et al., Glyco J 17, 323-329 (2000)), and traditional binding assays (Heeley, Endocr Res 28, 217-229 (2002)). In one embodiment, the extent of binding of an antibody to an unrelated protein is less than about 10% of the binding of the antibody to the antigen as measured, e.g. by SPR. In certain embodiments, an antibody that binds to the antigen has a dissociation constant ($K_D$) of ≤1 µM, ≤100 nM, ≤10 nM, ≤1 nM, ≤0.1 nM, ≤0.01 nM, or ≤0.001 nM (e.g. $10^{-8}$M or less, e.g. from $10^{-8}$M to $10^{-13}$M, e.g. from $10^{-9}$M to $10^{-13}$ M).

"Affinity" or "binding affinity" refers to the strength of the sum total of non-covalent interactions between a single binding site of a molecule (e.g. an antibody) and its binding partner (e.g. an antigen). Unless indicated otherwise, as used herein, "binding affinity" refers to intrinsic binding affinity which reflects a 1:1 interaction between members of a binding pair (e.g. antibody and antigen). The affinity of a molecule X for its partner Y can generally be represented by the dissociation constant ($K_D$), which is the ratio of dissociation and association rate constants ($k_{off}$ and $k_{on}$, respectively). Thus, equivalent affinities may comprise different rate constants, as long as the ratio of the rate constants remains the same. Affinity can be measured by common methods known in the art, including those described herein. A particular method for measuring affinity is Surface Plasmon Resonance (SPR).

"Reduced binding", for example reduced binding to an Fc receptor, refers to a decrease in affinity for the respective interaction, as measured for example by SPR. For clarity the term includes also reduction of the affinity to zero (or below the detection limit of the analytic method), i.e. complete abolishment of the interaction. Conversely, "increased binding" refers to an increase in binding affinity for the respective interaction.

As used herein, the term "single-chain" refers to a molecule comprising amino acid monomers linearly linked by peptide bonds.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$, diabodies, linear antibodies, single-chain antibody molecules (e.g. scFv), and single-domain antibodies. For a review of certain antibody fragments, see Hudson et al., Nat Med 9, 129-134 (2003). For a review of scFv fragments, see e.g. Plückthun, in The Pharmacology of Monoclonal Antibodies, vol. 113, Rosenburg and Moore eds., Springer-Verlag, New York, pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046. Diabodies are antibody fragments with two antigen-binding sites that may be bivalent or bispecific. See, for example, EP 404,097; WO 1993/01161; Hudson et al., Nat Med 9, 129-134 (2003); and Hollinger et al., Proc Natl Acad Sci USA 90, 6444-6448 (1993). Triabodies and tetrabodies are also described in Hudson et al., Nat Med 9, 129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see e.g. U.S. Pat. No. 6,248,516 B1). Antibody fragments can be made by various techniques, including but not limited to proteolytic digestion of an intact antibody as well as production by recombinant host cells (e.g. E. coli or phage), as described herein.

The terms "full length antibody", "intact antibody", and "whole antibody" are used herein interchangeably to refer to an antibody having a structure substantially similar to a native antibody structure.

"Native antibodies" refer to naturally occurring immunoglobulin molecules with varying structures. For example, native IgG-class antibodies are heterotetrameric glycoproteins of about 150,000 daltons, composed of two light chains and two heavy chains that are disulfide-bonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a light chain constant domain (CL), also called a light chain constant region. The heavy chain of an antibody may be assigned to one of five types, called α (IgA), δ (IgD), ε (IgE), γ (IgG), or µ (IgM), some of which may be further divided into subtypes, e.g. $\gamma_1$ (IgG$_1$), $\gamma_2$ (IgG$_2$), $\gamma_3$ (IgG$_3$), $\gamma_4$ (IgG$_4$), $\alpha_1$ (IgA$_1$) and $\alpha_2$ (IgA$_2$). The light chain of an antibody may be assigned to one of two types, called kappa (κ) and lambda (λ), based on the amino acid sequence of its constant domain. As used herein, "Fab fragment" refers to an antibody fragment comprising a light chain fragment comprising a VL domain and a constant domain of a light chain (CL), and a VH domain and a first constant domain (CH1) of a heavy chain.

The "class" of an antibody or immunoglobulin refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and µ, respectively.

An "IgG-class antibody" refers to an antibody having the structure of a naturally occurring immunoglobulin G (IgG) molecule. The antibody heavy chain of an IgG-class antibody has the domain structure VH-CH1-CH2-CH3. The antibody light chain of an IgG-class antibody has the domain structure VL-CL. An IgG-class antibody essentially consists of two Fab fragments and an Fc domain, linked via the immunoglobulin hinge region.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). See, e.g. Kindt et al., Kuby Immunology, 6$^{th}$ ed., W.H. Freeman and Co., page 91 (2007). A single VH or VL domain may be sufficient to confer antigen-binding specificity.

The term "hypervariable region" or "HVR", as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the complementarity determining regions (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3) (Chothia and Lesk, J. Mol. Biol. 196, 901-917 (1987)). Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3 (Kabat et al., Sequences of Proteins of Immunological Interest, 5th Ed. Public Health Service, National Institutes of Health, Bethesda, Md. (1991)). With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3 (see Almagro and Fransson, Front. Biosci. 13, 1619-1633 (2008)). Unless otherwise indicated, HVR residues and other residues in the variable domain (e.g. FR residues) are numbered herein according to Kabat et al., supra (refered to as "Kabat numbering").

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

The term "monoclonal antibody" as used herein refers to an antibody obtained from a population of substantially homogeneous antibodies, i.e., the individual antibodies comprising the population are identical and/or bind the same epitope, except for possible variant antibodies, e.g. containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "Fc domain" or "Fc region" herein is used to define a C-terminal region of an antibody heavy chain that contains at least a portion of the constant region. The term includes native sequence Fc regions and variant Fc regions. An IgG Fc region comprises an IgG CH2 and an IgG CH3 domain. The "CH2 domain" of a human IgG Fc region usually extends from an amino acid residue at about position 231 to an amino acid residue at about position 340. In one embodiment, a carbohydrate chain is attached to the CH2 domain. The CH2 domain herein may be a native sequence CH2 domain or variant CH2 domain. The "CH3 domain" comprises the stretch of residues C-terminal to a CH2 domain in an Fc region (i.e. from an amino acid residue at about position 341 to an amino acid residue at about position 447 of an IgG). The CH3 region herein may be a native sequence CH3 domain or a variant CH3 domain (e.g. a CH3 domain with an introduced "protuberance" ("knob") in one chain thereof and a corresponding introduced "cavity" ("hole") in the other chain thereof; see U.S. Pat. No. 5,821,333, expressly incorporated herein by reference). Such variant CH3 domains may be used to promote heterodimerization of two non-identical antibody heavy chains as herein described. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

The term "effector functions" refers to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g. B cell receptor), and B cell activation.

An "activating Fc receptor" is an Fc receptor that following engagement by an Fc region of an antibody elicits signaling events that stimulate the receptor-bearing cell to perform effector functions. Activating Fc receptors include FcγRIIIa (CD16a), FcγRI (CD64), FcγRIIa (CD32), and FcαRI (CD89). A particular activating Fc receptor is human FcγRIIIa (see UniProt accession no. P08637 (version 141)).

By a "native IL-10", also termed "wild-type IL-10", is meant a naturally occurring IL-10, as opposed to a "modified IL-10", which has been modified from a naturally occurring IL-10, e.g. to alter one or more of its properties such as stability. A modified IL-10 molecule may for example comprise modifications in the amino acid sequence, e.g. amino acid substitutions, deletions or insertions. A particular modified IL-10 molecule with increased stability in monomeric form has been described by Josephson et al. (J Biol Chem 275, 13552-13557 (2000)).

Native IL-10 is a homodimer composed of two α-helical, monomeric domains. The sequence of a native human IL-10 monomeric domain is shown in SEQ ID NO: 1. Hence, an "IL-10 monomer" is a protein of substantially similar sequence and/or structure as a monomeric domain of native IL-10.

By "stable" or "stability" when used with reference to a protein is meant that the structural integrity of the protein (e.g. its secondary structure) is preserved.

By "functional" when used with reference to a protein is meant that the protein is able to mediate biological functions, particularly the biological functions that a corresponding protein occurring in nature (e.g. native IL-10) would mediate. In the case of IL-10, biological functions may include activation of IL-10 receptor signaling, suppression of secretion of pro-inflammatory cytokines such as TNF α, IL-1, IL-6, IL-12, IL-2 and/or INFγ, inhibition of MEW II expression and upregulation of co-stimulatory molecules such as CD80 and/or CD86 in cells expressing IL-10 receptors (e.g. monocytes).

The term "peptide linker" refers to a peptide comprising one or more amino acids, typically about 2-20 amino acids. Peptide linkers are known in the art or are described herein. Suitable, non-immunogenic linker peptides include, for example, $(G_4S)_n$, $(SG_4)_n$, or $G_4(SG_4)_n$ peptide linkers. "n" is generally a number between 1 and 10, typically between 2 and 4.

A "knob-into-hole modification" refers to a modification within the interface between two antibody heavy chains in the CH3 domain, wherein i) in the CH3 domain of one heavy chain, an amino acid residue is replaced with an amino acid residue having a larger side chain volume, thereby generating a protuberance ("knob") within the interface in the CH3 domain of one heavy chain which is positionable in a cavity ("hole") within the interface in the CH3 domain of the other heavy chain, and ii) in the CH3 domain of the other heavy chain, an amino acid residue is replaced with an amino acid residue having a smaller side chain volume, thereby generating a cavity ("hole") within the interface in the second CH3 domain within which a protuberance ("knob") within the interface in the first CH3 domain is positionable. In one embodiment, the "knob-into-hole modification" comprises the amino acid substitution T366W and optionally the amino acid substitution S354C in one of the antibody heavy chains, and the amino acid substitutions T366S, L368A, Y407V and optionally Y349C in the other one of the antibody heavy chains. The knob-into-hole technology is described e.g. in U.S. Pat. No. 5,731,168; U.S. Pat. No. 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine). Introduction of two cysteine residues at position S354 and Y349, respectively, results in formation of a disulfide bridge between the two antibody heavy chains in the Fc region, further stabilizing the dimer (Carter, J Immunol Methods 248, 7-15 (2001)).

An amino acid "substitution" refers to the replacement in a polypeptide of one amino acid with another amino acid. In one embodiment, an amino acid is replaced with another amino acid having similar structural and/or chemical properties, e.g., conservative amino acid replacements. "Conservative" amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. Non-conservative substitutions will entail exchanging a member of one of these classes for another class. For example, amino acid substitutions can also result in replacing one amino acid with another amino acid having different structural and/or chemical properties, for example, replacing an amino acid from one group (e.g., polar) with another amino acid from a different group (e.g., basic). Amino acid substitutions can be generated using genetic or chemical methods well known in the art. Genetic methods may include site-directed mutagenesis, PCR, gene synthesis and the like. It is contemplated that methods of altering the side chain group of an amino acid by methods other than genetic engineering, such as chemical modification, may also be useful. Various designations may be used herein to indicate the same amino acid substitution. For example, a substitution from proline at position 329 of the antibody heavy chain to glycine can be indicated as 329G, G329, $G_{329}$, P329G, or Pro329Gly.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

"Polynucleotide" or "nucleic acid" as used interchangeably herein, refers to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. A sequence of nucleotides may be interrupted by non-nucleotide components. A polynucleotide may comprise modification(s) made after synthesis, such as conjugation to a label.

The term "modification" refers to any manipulation of the peptide backbone (e.g. amino acid sequence) or the post-translational modifications (e.g. glycosylation) of a polypeptide.

The term "vector" as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

The terms "host cell", "host cell line", and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate the fusion proteins of the present invention. Host cells include cultured cells, e.g. mammalian cultured cells, such as CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

An "effective amount" of an agent refers to the amount that is necessary to result in a physiological change in the cell or tissue to which it is administered.

A "therapeutically effective amount" of an agent, e.g. a pharmaceutical composition, refers to an amount effective, at dosages and for periods of time necessary, to achieve the desired therapeutic or prophylactic result. A therapeutically effective amount of an agent for example eliminates, decreases, delays, minimizes or prevents adverse effects of a disease.

An "individual" or "subject" is a mammal. Mammals include, but are not limited to, domesticated animals (e.g. cows, sheep, cats, dogs, and horses), primates (e.g. humans and non-human primates such as monkeys), rabbits, and rodents (e.g. mice and rats). Particularly, the individual or subject is a human.

The term "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical composition, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of a disease in the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

Fusion Proteins of the Invention

The invention provides novel antibody-IL-10 fusion protein with particularly advantageous properties such as produceability, stability, binding affinity and biological activity.

In a first aspect, the invention provides a fusion protein of an IgG-class antibody and an IL-10 molecule, wherein the fusion protein comprises two identical heavy chain polypeptides and two identical light chain polypeptides. In one embodiment, each of said heavy chain polypeptides comprises an IgG-class antibody heavy chain and an IL-10 monomer. In a more specific embodiment, said IL-10 monomer is fused at its N-terminus to the C-terminus of said IgG-class antibody heavy chain, optionally through a peptide linker. In one embodiment, said heavy chain polypeptides each essentially consist of an IgG-class antibody heavy chain, an IL-10 monomer and optionally a peptide linker. In one embodiment, each of said light chain polypeptides comprises an IgG-class antibody light chain. In one embodiment, said light chain polypeptides each essentially consist of an IgG-class antibody light chain. As compared to fusion proteins based on antibody fragments, the presence of an IgG-class antibody confers to the fusion protein of the invention favorable pharmacokinetic properties including a prolonged serum half-life (due to recycling through binding to FcRn, and molecular size being well above the threshold for renal filtration). The presence of an IgG-class antibody also enables simple purification of fusion proteins by e.g. protein A affinity chromatography. Surprisingly, as shown in the examples comparing the IgG-based IgG-IL-10 fusion protein of the invention to a corresponding fusion protein based on Fab fragments (Fab-IL-10), the presence of an IgG-class antibody also improves biological activity of the fusion protein when bound to its target antigen. The use of identical heavy (and light) chain polypeptides allows for simple production of the fusion protein, avoiding the formation of undesired side products and obviating the need for modifications promoting heterodimerization of non-identical heavy chains, such as a knob-into-hole modification.

Figure 16B:
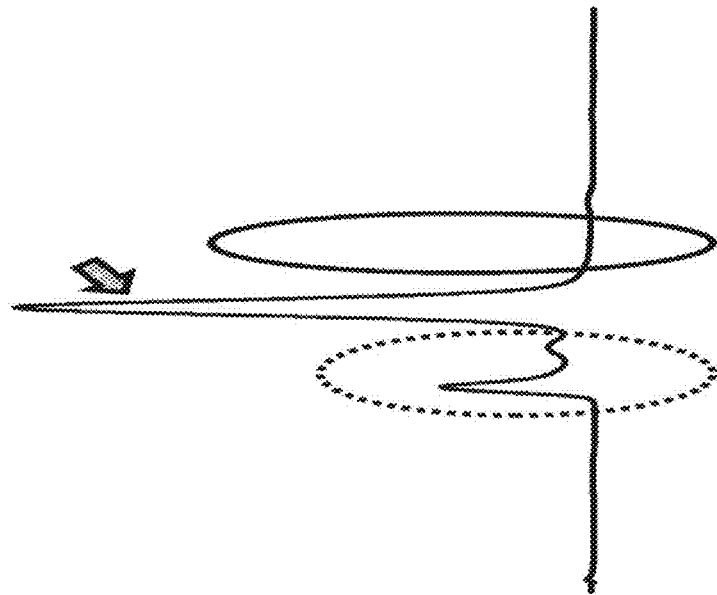
FIGS. 16A-16B Comparison of size exclusion chromatography (SEC) profiles of Fab-IL-10 and IgG-IL-10 formats. Arrows indicate the desired dimeric products, aggregates are indicated by dotted circles and monomers are indicated by solid circles. In contrast to the Fab-IL-10 format, the IgG-IL-10 format does not lead to monomers or 'half-molecules' due to the disulfide-linked covalent homodimerization of its heavy chains.
Figure 16A:
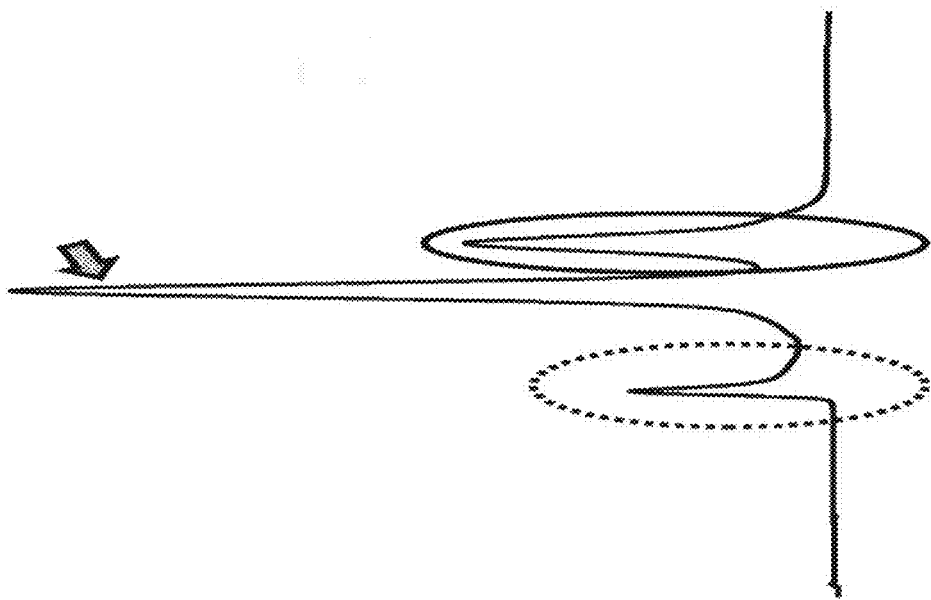

In some embodiments, said IL-10 monomer is a native IL-10 monomer, particularly a native human IL-10 monomer. In a specific embodiment, said IL-10 monomer comprises the polypeptide sequence of SEQ ID NO: 1. In one embodiment, said IL-10 monomers comprised in said heavy chain polypeptides form a functional homodimeric IL-10 molecule. This fusion protein format is particularly advantageous in that the two IL-10 monomers form a fully functional, biologically active IL-10 dimer. Moreover, in contrast to fusion proteins based on antibody fragments, in the fusion protein of the invention dimerization not only occurs in between the IL-10 monomers, but also between the antibody heavy chains to which the monomers are fused. Therefore, the tendency of the IL-10 dimer comprised the fusion proteins of the invention of disassembling into two monomers is reduced, as compared e.g. to the Fab-IL-10 fusion proteins described herein (see FIGS. 16A-16B). Importantly, this fusion protein format is also superior to other fusion protein formats described herein in terms of biological activity.

In other embodiments, said IL-10 monomer is a modified IL-10 monomer, particularly a modified human IL-10 monomer. In one embodiment, said modified IL-10 monomer is stable at pH 7.0, 37° C. in monomeric form. In one embodiment, said modified IL-10 monomer has improved stability at pH 7.0, 37° C. as compared to a native IL-10 monomer. A suitable modified IL-10 monomer is described in Josephson et al., J Biol Chem 275, 13552-13557 (2000), which also describes methods for measuring stability of IL-10 monomers. In a specific embodiment, said IL-10 monomer comprises the polypeptide sequence of SEQ ID NO: 5. In one embodiment, said IL-10 monomers comprised in said heavy chain polypeptides do not homodimerize with each other. This fusion protein format comprises two separate modified IL-10 monomers, rather than an IL-10 dimer. As shown in the examples, this fusion protein format has similar binding affinity (avidity) to the IL-10 receptor 1 as the fusion proteins comprising an IL-10 dimer. Moreover, it is particularly well produceable, with high expression yields and little aggregation propensity.

In one embodiment, said IgG-class antibody is an $IgG_1$-subclass antibody. In one embodiment, said IgG-class antibody is a human antibody, i.e. it comprises human variable and constant regions. Sequences of exemplary human $IgG_1$ heavy and light chain constant regions are shown in SEQ ID NOs 79 and 80, respectively. In one embodiment, the IgG-class antibody comprises a human Fc region, particularly a human IgG Fc region, more particularly a human $IgG_1$ Fc region. In one embodiment, said IgG-class antibody is a full-length antibody. In one embodiment, said IgG-class antibody is a monoclonal antibody.

While the Fc domain of the IgG-class antibody confers to the fusion proteins favorable pharmacokinetic properties, including a long serum half-life which contributes to good accumulation in the target tissue and a favorable tissue-blood distribution ratio, it may at the same time lead to undesirable targeting of the fusion protein to cells expressing Fc receptors rather than to the preferred antigen-bearing cells. Moreover, the activation of Fc receptor signaling pathways may lead to cytokine release resulting in activation of (pro-inflammatory) cytokine receptors and severe side effects upon systemic administration. Therefore, in one embodiment, said IgG-class antibody comprises a modification reducing binding affinity of the antibody to an Fc receptor, as compared to a corresponding IgG-class antibody without said modification. In a specific embodiment, said Fc receptor is an Fcγ receptor, particularly a human Fcγ receptor. Binding affinity to Fc receptors can be easily determined e.g. by ELISA, or by Surface Plasmon Resonance (SPR) using standard instrumentation such as a BIAcore instrument (GE Healthcare) and Fc receptors such as may be obtained by recombinant expression. A specific illustrative and exemplary embodiment for measuring binding affinity is described in the following. According to one embodiment, Binding affinity to an Fc receptor is measured by surface plasmon resonance using a BIACORE® T100 machine (GE Healthcare) at 25° C. with ligand (Fc receptor) immobilized on CM5 chips. Briefly, carboxymethylated dextran biosensor chips (CM5, GE Healthcare) are activated with N-ethyl-N'-(3-dimethylaminopropyl)-carbodiimide hydrochloride (EDC) and N-hydroxysuccinimide (NHS) according to the supplier's instructions. Recombinant ligand is diluted with 10 mM sodium acetate, pH 5.5, to 0.5-30 μg/ml before injection at a flow rate of 10 μl/min to achieve approximately 100-5000 response units (RU) of coupled protein. Following the injection of the ligand, 1 M ethanolamine is injected to block unreacted groups. For kinetics measurements, three- to five-fold serial dilutions of antibody (range between ~0.01 nM to 300 nM) are injected in HBS-EP+ (GE Healthcare, 10 mM HEPES, 150 mM NaCl, 3 mM EDTA, 0.05% Surfactant P20, pH 7.4) at 25° C. at a flow rate of approximately 30-50 μl/min. Association rates ($k_{on}$) and dissociation rates ($k_{off}$) are calculated using a simple one-to-one Langmuir binding model (BIACORE® T100 Evaluation Software version 1.1.1) by simultaneously fitting the association and dissociation sensorgrams. The equilibrium dissociation constant ($K_D$) is calculated as the ratio $k_{off}/k_{on}$. See, e.g., Chen et al., J Mol Biol 293, 865-881 (1999). Alternatively, binding affinity antibodies to Fc receptors may be evaluated using cell lines known to express particular Fc receptors, such as NK cells expressing FcγIIIa receptor.

In one embodiment, the modification comprises one or more amino acid mutation that reduces the binding affinity of the antibody to an Fc receptor. In one embodiment the amino acid mutation is an amino acid substitution. Typically, the same one or more amino acid mutation is present in each of the two antibody heavy chains. In one embodiment said amino acid mutation reduces the binding affinity of the antibody to the Fc receptor by at least 2-fold, at least 5-fold, or at least 10-fold. In embodiments where there is more than one amino acid mutation that reduces the binding affinity of the antibody to the Fc receptor, the combination of these amino acid mutations may reduce the binding affinity of the antibody to the Fc receptor by at least 10-fold, at least 20-fold, or even at least 50-fold. In one embodiment said IgG-class antibody exhibits less than 20%, particularly less than 10%, more particularly less than 5% of the binding affinity to an Fc receptor as compared to a corresponding IgG-class antibody without said modification.

In one embodiment, said Fc receptor is an activating Fc receptor. In a specific embodiment, said Fc receptor is selected from the group of FcγRIIIa (CD16a), FcγRI (CD64), FcγRIIa (CD32) and FcγRI (CD89). In a specific embodiment the Fc receptor is an Fcγ receptor, more specifically an FcγRIIIa, FcγRI or FcγRIIa receptor. Preferably, binding affinity to each of these receptors is reduced. In an even more specific embodiment, said Fc receptor is FcγIIIa, particularly human FcγIIIa. In some embodiments binding affinity to a complement component, specifically binding affinity to C1q, is also reduced. In one embodiment binding affinity to neonatal Fc receptor (FcRn) is not reduced. Substantially similar binding to FcRn, i.e. preservation of the binding affinity of the antibody to said receptor, is achieved when the antibody exhibits greater than about 70% of the binding affinity of an unmodified form of the antibody to FcRn. IgG-class antibodies comprised in the fusion proteins of the invention may exhibit greater than about 80% and even greater than about 90% of such affinity.

In one embodiment, said modification reducing binding affinity of the antibody to an Fc receptor is in the Fc region, particularly the CH2 region, of the IgG-class antibody. In one embodiment, said IgG-class antibody comprises an amino acid substitution at position 329 (EU numbering) of the antibody heavy chains. In a more specific embodiment said amino acid substitution is P329A or P329G, particularly P329G. In one embodiment, said IgG-class antibody comprises amino acid substitutions at positions 234 and 235 (EU numbering) of the antibody heavy chains. In a specific embodiment, said amino acid substitutions are L234A and L235A (LALA). In one embodiment said IgG-class antibody comprises an amino acid substitution at position 329 (EU numbering) of the antibody heavy chains and a further amino acid substitution at a position selected from position 228, 233, 234, 235, 297 and 331 of the antibody heavy chains. In a more specific embodiment the further amino acid substitution is S228P, E233P, L234A, L235A, L235E, N297A, N297D or P331S. In a particular embodiment, said IgG-class antibody comprises amino acid substitutions at positions P329, L234 and L235 (EU numbering) of the antibody heavy chains. In a more particular embodiment, said IgG-class antibody comprises the amino acid substitutions L234A, L235A and P329G (LALA P329G) in the antibody heavy chains. This combination of amino acid substitutions almost particularly efficiently abolishes Fcγ receptor binding of a human IgG-class antibody, as described in PCT publication no. WO 2012/130831, incorporated herein by reference in its entirety. PCT publication no. WO 2012/130831 also describes methods of preparing such modified antibody and methods for determining its properties such as Fc receptor binding or effector functions.

Antibodies comprising modifications in the antibody heavy chains can be prepared by amino acid deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing.

Antibodies which comprise modifications reducing Fc receptor binding generally have reduced effector functions, particularly reduced ADCC, as compared to corresponding unmodified antibodies. Hence, in one embodiment, said modification reducing binding affinity of the IgG-class antibody to an Fc receptor reduces effector function of the IgG-class antibody. In a specific embodiment, said effector function is antibody-dependent cell-mediated cytotoxicity (ADCC). In one embodiment, ADCC is reduced to less than 20% of the ADCC induced by a corresponding IgG-class antibody without said modification. Effector function of an antibody can be measured by methods known in the art. Examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assays methods may be employed (see, for example, ACTI™ non-radioactive cytotoxicity assay for flow cytometry (CellTechnology, Inc. Mountain View, Calif.); and CytoTox 96® non-radioactive cytotoxicity assay (Promega, Madison, Wis.)). Useful effector cells for such assays include peripheral blood mononuclear cells (PBMC) and Natural Killer (NK) cells. Alternatively, or additionally, ADCC activity of the molecule of interest may be assessed in vivo, e.g. in a animal model such as that disclosed in Clynes et al., Proc Natl Acad Sci USA 95, 652-656 (1998). In some embodiments binding of the IgG-class antibody to a complement component, specifically to C1q, is also reduced. Accordingly, complement-dependent cytotoxicity (CDC) may also be reduced. C1q binding assays may be carried out to determine whether the antibody is able to bind C1q and hence has CDC activity. See e.g. C1q and C3c binding ELISA in WO 2006/029879 and WO 2005/100402. To assess complement activation, a CDC assay may be performed (see, for example, Gazzano-Santoro et al., J Immunol Methods 202, 163 (1996); Cragg et al., Blood 101, 1045-1052 (2003); and Cragg and Glennie, Blood 103, 2738-2743 (2004)).

In addition to the IgG-class antibodies described hereinabove and in PCT publication no. WO 2012/130831, antibodies with reduced Fc receptor binding and/or effector function also include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

IgG$_4$-subclass antibodies exhibit reduced binding affinity to Fc receptors and reduced effector functions as compared to IgG$_1$ antibodies. Hence, in some embodiments, said IgG-class antibody comprised in the fusion protein of the invention is an IgG$_4$-subclass antibody, particularly a human IgG$_4$-subclass antibody. In one embodiment said IgG$_4$-subclass antibody comprises amino acid substitutions in the Fc region at position S228, specifically the amino acid substitution S228P. To further reduce its binding affinity to an Fc receptor and/or its effector function, in one embodiment, said IgG$_4$-subclass antibody comprises an amino acid substitution at position L235, specifically the amino acid substitution L235E. In another embodiment, said IgG$_4$-subclass antibody comprises an amino acid substitution at position P329, specifically the amino acid substitution P329G. In a particular embodiment, said IgG$_4$-subclass antibody comprises amino acid substitutions at positions S228, L235 and P329, specifically amino acid substitutions S228P, L235E and P329G. Such modified IgG$_4$-subclass antibodies and their Fcγ receptor binding properties are described in PCT publication no. WO 2012/130831, incorporated herein by reference in its entirety.

The antibodies of the invention combine a number of properties which are particularly advantageous, for example for therapeutic applications.

In one embodiment, said IgG-class antibody is capable of specific binding to Fibroblast Activation Protein (FAP). FAP has been identified as a suitable target for the treatment of inflammatory diseases using the fusion proteins of the invention. In a specific embodiment, the fusion protein is capable of binding to FAP with an affinity constant ($K_D$) of smaller than 1 nM, particularly smaller than 100 pM, when measured by Surface Plasmon Resonance (SPR) at 25° C. A method for measuring binding affinity to FAP by SPR is described herein. In one embodiment, affinity ($K_D$) of fusion proteins is measured by SPR using a ProteOn XPR36 instrument (Biorad) at 25° C. with His-tagged FAP antigens immobilized by anti-His antibodies covalently coupled to GLM chips. In an exemplary method, the target protein (FAP) is captured via its H6-tag by a covalently immobilized anti-penta His IgG (Qiagen #34660, mouse monoclonal antibody), immobilized at high levels (up to ~5.000 RU) at 30 µl/min onto separate vertical channels of a GLM chip by simultaneously activating all channels for 5 min with a freshly prepared mixture of 1-ethyl-3-(3-dimethylaminopropyl)-carboiimide (EDC) and N-hydroxysuccinimide (sNHS), and subsequently injecting 15 µg/ml anti-penta His IgG in 10 mM sodium acetate buffer pH 4.5 for 180 sec. Channels are blocked using a 5-min injection of ethanolamine. His6-tagged FAP is captured from a 5 µg/ml dilution in running buffer along the vertical channels for 60 s at 30 µl/min to achieve ligand densities between ~250 and 600 RU. In a one-shot kinetic assay set-up (OSK), fusion protein are injected as analytes along the horizontal channels in a five-fold dilution series ranging from 50 to 0.08 nM at 100 µl/min. Association phase is recorded for 180 s, dissociation phase for 600 s. In case of interactions exhibiting very slow off-rates, recording of off-rates is extended up to 1800 s in order to observe the dissociation of the complex. Running buffer (PBST) is injected along the sixth channel to provide an "in-line" blank for referencing. Association rates ($k_{on}$) and dissociation rates ($k_{off}$) are calculated using a simple 1:1 Langmuir binding model (ProteOn Manager software version 2.1) by simultaneously fitting the association and dissociation sensorgrams. The equilibrium dissociation constant ($K_D$) is calculated as the ratio $k_{off}/k_{on}$.

In one embodiment, said FAP is human, mouse and/or cynomolgus FAP. Preferably, the IgG-class antibody comprised in the fusion protein of the invention is cross-reactive for human and cynomolgus monkey and/or mouse FAP, which enables e.g. in vivo studies in cynomolgus monkeys and/or mice prior to human use.

In a specific embodiment, said IgG-class antibody comprises the heavy chain CDR (HCDR) 1 of SEQ ID NO: 37, the HCDR 2 of SEQ ID NO: 41, the HCDR 3 of SEQ ID NO: 49, the light chain CDR (LCDR) 1 of SEQ ID NO: 53, the LCDR 2 of SEQ ID NO: 57 and the LCDR 3 of SEQ ID NO: 61. In an even more specific embodiment, said IgG-class antibody comprises the heavy chain variable region (VH) of SEQ ID NO: 63 and the light chain variable region (VL) of SEQ ID NO: 65. In another, particular, specific embodiment, said IgG-class antibody comprises the HCDR 1 of SEQ ID NO: 37, the HCDR 2 of SEQ ID NO: 43, the HCDR 3 of SEQ ID NO: 47, the LCDR 1 of SEQ ID NO: 51, the LCDR 2 of SEQ ID NO: 55 and the LCDR 3 of SEQ ID NO: 59. In an even more specific embodiment, said IgG-class antibody comprises the VH of SEQ ID NO: 67 and the VL of SEQ ID NO: 69. As shown in the examples, these antibodies show particularly strong binding affinity/avidity to human, mouse as well as cynomolgus FAP.

In further specific embodiments, said IgG-class antibody comprises the HCDR 1 of SEQ ID NO: 39, the HCDR 2 of SEQ ID NO: 45, the HCDR 3 of SEQ ID NO: 49, the light chain CDR (LCDR) 1 of SEQ ID NO: 53, the LCDR 2 of SEQ ID NO: 57 and the LCDR 3 of SEQ ID NO: 61. In an even more specific embodiment, said IgG-class antibody comprises the VH of SEQ ID NO: 71 and the VL of SEQ ID NO: 73. In another specific embodiment, said IgG-class antibody comprises the HCDR 1 of SEQ ID NO: 37, the HCDR 2 of SEQ ID NO: 41, the HCDR 3 of SEQ ID NO: 47, the LCDR 1 of SEQ ID NO: 51, the LCDR 2 of SEQ ID NO: 55 and the LCDR 3 of SEQ ID NO: 59. In an even more specific embodiment, said IgG-class antibody comprises the VH of SEQ ID NO: 75 and the VL of SEQ ID NO: 77.

In one embodiment, the fusion protein is capable of binding to IL-10 receptor-1 (IL-10R1) with an affinity constant ($K_D$) of smaller than 1 nM, particularly smaller than 100 pM, when measured by SPR at 25° C. A method for measuring binding affinity to IL-10R1 by SPR is described herein. In one embodiment, affinity ($K_D$) of fusion proteins is measured by SPR using a ProteOn XPR36 instrument (Biorad) at 25° C. with biotinylated IL-10R1 immobilized on NLC chips by neutravidin capture. In an exemplary method, between 400 and 1600 RU of IL-10R1 are captured on the neutravidin-derivatized chip matrix along vertical channels at a concentration of 10 µg/ml and a flow rate of 30 µl/sec for varying contact times. Binding to biotinylated IL10R1 is measured at six different analyte concentrations (50, 10, 2, 0.4, 0.08, 0 nM) by injections in horizontal orientation at 100 µl/min, recording the association rate for 180 s, the dissociation rate for 600 s. Running buffer (PBST) is injected along the sixth channel to provide an "in-line" blank for referencing. Association rates ($k_{on}$) and dissociation rates ($k_{off}$) are calculated using a simple 1:1 Langmuir binding model (ProteOn Manager software version 2.1) by simultaneously fitting the association and dissociation sensorgrams. The equilibrium dissociation constant ($K_D$) is calculated as the ratio $k_{off}/k_{on}$.

In a specific embodiment, said IL-10R1 is human IL-10R1. In one embodiment, said affinity constant ($K_D$) for binding to IL-10R1 is about equal or greater than said affinity constant ($K_D$) for binding to FAP, when measured by SPR at 25° C. In a specific embodiment, said $K_D$ for binding to IL-10R1 is greater than about half of said $K_D$ for binding to FAP. The particular ratio of KD values of the fusion protein of the invention for binding to FAP and IL-10R1 makes them particularly suitable for efficient targeting IL-10 to FAP-expressing tissues. Without wishing to be bound by theory, the fusion proteins of the invention, due to their binding affinity to FAP being at least equally high as their binding affinity to IL-10R1, are less likely to bind to IL-10R1-expressing cells outside the target tissue (e.g. in the circulation) prior to reaching the FAP-expressing target tissue.

In a particular aspect, the invention provides a fusion protein of a human $IgG_1$-subclass antibody, capable of specific binding to FAP and comprising a modification reducing binding affinity of the antibody to an Fc receptor as compared to a corresponding human $IgG_1$-subclass antibody without said modification, and an IL-10 molecule, wherein the fusion protein comprises two identical heavy chain polypeptides, each comprising a native IL-10 monomer fused at its N-terminus to the C-terminus of a human $IgG_1$-subclass antibody heavy chain, and two identical light chains.

In a specific embodiment, said fusion protein comprises a heavy chain polypeptide that is at least about 80%, 85%, 90%, 95%, 96%, 97%, 98%, 99% or 100% identical to the polypeptide of SEQ ID NO: 9, and a light chain polypeptide that is at least about 80%, 85%, 90%, 95%, 96%, 97%, 98%, 99% or 100% identical to the polypeptide of SEQ ID NO: 7. In another specific embodiment, said fusion protein comprises a heavy chain polypeptide that is at least about 80%, 85%, 90%, 95%, 96%, 97%, 98%, 99% or 100% identical to the polypeptide of SEQ ID NO: 27, and a light chain polypeptide that is at least about 80%, 85%, 90%, 95%, 96%, 97%, 98%, 99% or 100% identical to the polypeptide of SEQ ID NO: 25.

In a further aspect, the invention provides a fusion protein of a human IgG$_1$-subclass antibody, capable of specific binding to FAP and comprising a modification reducing binding affinity of the antibody to an Fc receptor as compared to a corresponding human IgG$_1$-subclass antibody without said modification, and an IL-10 molecule, wherein the fusion protein comprises two identical heavy chain polypeptides, each comprising a modified IL-10 monomer fused at its N-terminus to the C-terminus of a human IgG$_1$-subclass antibody heavy chain, and two identical light chains.

In a specific embodiment, said fusion protein comprises a heavy chain polypeptide that is at least about 80%, 85%, 90%, 95%, 96%, 97%, 98%, 99% or 100% identical to the polypeptide of SEQ ID NO: 17, and a light chain polypeptide that is at least about 80%, 85%, 90%, 95%, 96%, 97%, 98%, 99% or 100% identical to the polypeptide of SEQ ID NO: 7. In another specific embodiment, said fusion protein comprises a heavy chain polypeptide that is at least about 80%, 85%, 90%, 95%, 96%, 97%, 98%, 99% or 100% identical to the polypeptide of SEQ ID NO: 29, and a light chain polypeptide that is at least about 80%, 85%, 90%, 95%, 96%, 97%, 98%, 99% or 100% identical to the polypeptide of SEQ ID NO: 25.

Polynucleotides

The invention further provides polynucleotides encoding a fusion as described herein or an antigen-binding fragment thereof.

Polynucleotides of the invention include those that are at least about 80%, 85%, 90%, 95%, 96%, 97%, 98%, 99%, or 100% identical to the sequences set forth in SEQ ID NOs 2, 6, 8, 10, 18, 26, 28, 30, 38, 40, 42, 44, 46, 48, 50, 52, 54, 56, 58, 60, 62, 64, 66, 68, 70, 72, 74, 76, 78 and 89 including functional fragments or variants thereof.

The polynucleotides encoding fusion proteins of the invention may be expressed as a single polynucleotide that encodes the entire fusion protein or as multiple (e.g., two or more) polynucleotides that are co-expressed. Polypeptides encoded by polynucleotides that are co-expressed may associate through, e.g., disulfide bonds or other means to form a functional fusion protein. For example, the light chain portion of an antibody may be encoded by a separate polynucleotide from the heavy chain portion of the antibody. When co-expressed, the heavy chain polypeptides will associate with the light chain polypeptides to form the antibody.

In one embodiment, the present invention is directed to a polynucleotide encoding a fusion protein of an IgG-class antibody and an IL-10 molecule, or an antigen-binding fragment thereof, wherein the polynucleotide comprises a sequence that encodes a variable region sequence as shown in SEQ ID NO 63, 65, 67, 69, 71, 73, 75 or 77. In another embodiment, the present invention is directed to a polynucleotide encoding a fusion protein of an IgG-class antibody and an IL-10 molecule, or a fragment thereof, wherein the polynucleotide comprises a sequence that encodes a polypeptide sequence as shown in SEQ ID NO 7, 9, 17, 25, 27 or 29. In another embodiment, the invention is further directed to a polynucleotide encoding a fusion protein of an IgG-class antibody and an IL-10 molecule, or a fragment thereof, wherein the polynucleotide comprises a sequence that is at least about 80%, 85%, 90%, 95%, 96%, 97%, 98%, or 99% identical to a nucleic acid sequence shown SEQ ID NO 2, 6, 8, 10, 18, 26, 28, 30, 38, 40, 42, 44, 46, 48, 50, 52, 54, 56, 58, 60, 62, 64, 66, 68, 70, 72, 74, 76, 78 or 89. In another embodiment, the invention is directed to a polynucleotide encoding a fusion protein of an IgG-class antibody and an IL-10 molecule, or a fragment thereof, wherein the polynucleotide comprises a nucleic acid sequence shown in SEQ ID NO 2, 6, 8, 10, 18, 26, 28, 30, 38, 40, 42, 44, 46, 48, 50, 52, 54, 56, 58, 60, 62, 64, 66, 68, 70, 72, 74, 76, 78 or 89. In another embodiment, the invention is directed to a polynucleotide encoding a fusion protein of an IgG-class antibody and an IL-10 molecule, or a fragment thereof, wherein the polynucleotide comprises a sequence that encodes a variable region sequence that is at least about 80%, 85%, 90%, 95%, 96%, 97%, 98%, or 99% identical to an amino acid sequence of SEQ ID NO 63, 65, 67, 69, 71, 73, 75 or 77. In another embodiment, the invention is directed to a polynucleotide encoding a fusion protein of an IgG-class antibody and an IL-10 molecule, or a fragment thereof, wherein the polynucleotide comprises a sequence that encodes a polypeptide sequence that is at least 80%, 85%, 90%, 95%, 96%, 97%, 98%, or 99% identical to an amino acid sequence of SEQ ID NO 7, 9, 17, 25, 27 or 29. The invention encompasses a polynucleotide encoding an a fusion protein of an IgG-class antibody and an IL-10 molecule, or a fragment thereof, wherein the polynucleotide comprises a sequence that encodes the variable region sequences of SEQ ID NO 63, 65, 67, 69, 71, 73, 75 or 77 with conservative amino acid substitutions. The invention also encompasses a polynucleotide encoding a fusion protein of an IgG-class antibody and an IL-10 molecule, or a fragment thereof, wherein the polynucleotide comprises a sequence that encodes the polypeptide sequences of SEQ ID NO 7, 9, 17, 25, 27 or 29 with conservative amino acid substitutions.

In certain embodiments the polynucleotide or nucleic acid is DNA. In other embodiments, a polynucleotide of the present invention is RNA, for example, in the form of messenger RNA (mRNA). RNA of the present invention may be single stranded or double stranded.

Recombinant Methods

Fusion proteins of the invention may be obtained, for example, by solid-state peptide synthesis (e.g. Merrifield solid phase synthesis) or recombinant production. For recombinant production one or more polynucleotide encoding the fusion protein (fragment), e.g., as described above, is isolated and inserted into one or more vectors for further cloning and/or expression in a host cell. Such polynucleotide may be readily isolated and sequenced using conventional procedures. In one embodiment a vector, preferably an expression vector, comprising one or more of the polynucleotides of the invention is provided. Methods which are well known to those skilled in the art can be used to construct expression vectors containing the coding sequence of a fusion protein (fragment) along with appropriate transcriptional/translational control signals. These methods include in vitro recombinant DNA techniques, synthetic techniques and in vivo recombination/genetic recombination. See, for example, the techniques described in Maniatis et al., MOLECULAR CLONING: A LABORATORY MANUAL, Cold Spring Harbor Laboratory, N.Y. (1989); and Ausubel et al., CURRENT PROTOCOLS IN MOLECULAR BIOLOGY, Greene Publishing Associates and Wiley Interscience, N.Y (1989). The expression vector can be part of a plasmid, virus, or may be a nucleic acid fragment. The expression vector includes an expression cassette into which the polynucleotide encoding the fusion protein (fragment) (i.e. the coding region) is cloned in operable association with a promoter and/or other transcription or translation control elements. As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' untranslated regions, and the like, are not part of a coding region. Two or more coding regions can be present in a single polynucleotide construct, e.g. on a single vector, or in separate polynucleotide constructs, e.g. on separate (different) vectors. Furthermore, any vector may contain a single coding region, or may comprise two or more coding regions, e.g. a vector of the present invention may encode one or more polypeptides, which are post- or co-translationally separated into the final proteins via proteolytic cleavage. In addition, a vector, polynucleotide, or nucleic acid of the invention may encode heterologous coding regions, either fused or unfused to a polynucleotide encoding the fusion protein (fragment) of the invention, or variant or derivative thereof. Heterologous coding regions include without limitation specialized elements or motifs, such as a secretory signal peptide or a heterologous functional domain. An operable association is when a coding region for a gene product, e.g. a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein. A variety of transcription control regions are known to those skilled in the art. These include, without limitation, transcription control regions, which function in vertebrate cells, such as, but not limited to, promoter and enhancer segments from cytomegaloviruses (e.g. the immediate early promoter, in conjunction with intron-A), simian virus 40 (e.g. the early promoter), and retroviruses (such as, e.g. Rous sarcoma virus). Other transcription control regions include those derived from vertebrate genes such as actin, heat shock protein, bovine growth hormone and rabbit â-globin, as well as other sequences capable of controlling gene expression in eukaryotic cells. Additional suitable transcription control regions include tissue-specific promoters and enhancers as well as inducible promoters (e.g. promoters inducible tetracyclins). Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence). The expression cassette may also include other features such as an origin of replication, and/or chromosome integration elements such as retroviral long terminal repeats (LTRs), or adeno-associated viral (AAV) inverted terminal repeats (ITRs).

Polynucleotide and nucleic acid coding regions of the present invention may be associated with additional coding regions which encode secretory or signal peptides, which direct the secretion of a polypeptide encoded by a polynucleotide of the present invention. For example, if secretion of the fusion is desired, DNA encoding a signal sequence may be placed upstream of the nucleic acid encoding a fusion protein of the invention or a fragment thereof. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the translated polypeptide to produce a secreted or "mature" form of the polypeptide. In certain embodiments, the native signal peptide, e.g. an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase. The amino acid and nucleotide sequences of an exemplary secretory signal peptide are shown in SEQ ID NOs 35 and 36, respectively.

DNA encoding a short protein sequence that could be used to facilitate later purification (e.g. a histidine tag) or assist in labeling the fusion protein may be included within or at the ends of the fusion protein (fragment) encoding polynucleotide.

In a further embodiment, a host cell comprising one or more polynucleotides of the invention is provided. In certain embodiments a host cell comprising one or more vectors of the invention is provided. The polynucleotides and vectors may incorporate any of the features, singly or in combination, described herein in relation to polynucleotides and vectors, respectively. In one such embodiment a host cell comprises (e.g. has been transformed or transfected with) a vector comprising a polynucleotide that encodes (part of) a fusion protein of the invention. As used herein, the term "host cell" refers to any kind of cellular system which can be engineered to generate the fusion proteins of the invention or fragments thereof. Host cells suitable for replicating and for supporting expression of fusion proteins are well known in the art. Such cells may be transfected or transduced as appropriate with the particular expression vector and large quantities of vector containing cells can be grown for seeding large scale fermenters to obtain sufficient quantities of the fusion protein for clinical applications. Suitable host cells include prokaryotic microorganisms, such as *E. coli*, or various eukaryotic cells, such as Chinese hamster ovary cells (CHO), insect cells, or the like. For example, polypeptides may be produced in bacteria in particular when glycosylation is not needed. After expression, the polypeptide may be isolated from the bacterial cell paste in a soluble fraction and can be further purified. In addition to prokaryotes, eukaryotic microbes such as filamentous fungi or yeast are suitable cloning or expression hosts for polypeptide-encoding vectors, including fungi and yeast strains whose glycosylation pathways have been "humanized", resulting in the production of a polypeptide with a partially or fully human glycosylation pattern. See Gerngross, Nat Biotech 22, 1409-1414 (2004), and Li et al., Nat Biotech 24, 210-215 (2006). Suitable host cells for the expression of (glycosylated) polypeptides are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells. Plant cell cultures can also be utilized as hosts. See e.g. U.S. Pat. Nos. 5,959,177, 6,040,498, 6,420,548, 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham et al., J Gen Virol 36, 59 (1977)), baby hamster kidney cells (BHK), mouse sertoli cells (TM4 cells as described, e.g., in Mather, Biol Reprod 23, 243-251 (1980)), monkey kidney cells (CV1), African green monkey kidney cells (VERO-76), human cervical carcinoma cells (HELA), canine kidney cells (MDCK), buffalo rat liver cells (BRL 3A), human lung cells (W138), human liver cells (Hep G2), mouse mammary tumor cells (MMT 060562), TRI cells (as described, e.g., in Mather et al., Annals N.Y. Acad Sci 383, 44-68 (1982)), MRC 5 cells, and FS4 cells. Other useful mammalian host cell lines include Chinese hamster ovary (CHO) cells, including dhfr⁻ CHO cells (Urlaub et al., Proc Natl Acad Sci USA 77, 4216 (1980)); and myeloma cell lines such as YO, NS0, P3X63 and Sp2/0. For a review of certain mammalian host cell lines suitable for protein production, see, e.g., Yazaki and Wu, Methods in Molecular Biology, Vol. 248 (B. K. C. Lo, ed., Humana Press, Totowa, N.J.), pp. 255-268 (2003). Host cells include cultured cells, e.g., mammalian cultured cells, yeast cells, insect cells, bacterial cells and plant cells, to name only a few, but also cells comprised within a transgenic animal, transgenic plant or cultured plant or animal tissue. In one embodiment, the host cell is a eukaryotic cell, preferably a mammalian cell, such as a Chinese Hamster Ovary (CHO) cell, a human embryonic kidney (HEK) cell or a lymphoid cell (e.g., Y0, NS0, Sp20 cell).

Standard technologies are known in the art to express foreign genes in these systems. Cells expressing a polypeptide comprising either the heavy or the light chain of an antibody, may be engineered so as to also express the other of the antibody chains such that the expressed product is an antibody that has both a heavy and a light chain.

In one embodiment, a method of producing a fusion protein according to the invention is provided, wherein the method comprises culturing a host cell comprising a polynucleotide encoding the fusion protein, as provided herein, under conditions suitable for expression of the fusion protein, and recovering the fusion protein from the host cell (or host cell culture medium).

In the fusion proteins of the invention, the components (IgG-class antibody and IL-10 molecule) are genetically fused to each other. Fusion proteins can be designed such that its components are fused directly to each other or indirectly through a linker sequence. The composition and length of the linker may be determined in accordance with methods well known in the art and may be tested for efficacy. Additional sequences may also be included to incorporate a cleavage site to separate the individual components of the fusion protein if desired, for example an endopeptidase recognition sequence.

In certain embodiments the fusion proteins of the invention comprise at least an antibody variable region capable of binding to an antigen such as FAP. Variable regions can form part of and be derived from naturally or non-naturally occurring antibodies and fragments thereof. Methods to produce polyclonal antibodies and monoclonal antibodies are well known in the art (see e.g. Harlow and Lane, "Antibodies, a laboratory manual", Cold Spring Harbor Laboratory, 1988). Non-naturally occurring antibodies can be constructed using solid phase-peptide synthesis, can be produced recombinantly (e.g. as described in U.S. Pat. No. 4,186,567) or can be obtained, for example, by screening combinatorial libraries comprising variable heavy chains and variable light chains (see e.g. U.S. Pat. No. 5,969,108 to McCafferty).

Any animal species of antibody can be used in the invention. Non-limiting antibodies useful in the present invention can be of murine, primate, or human origin. If the antibody is intended for human use, a chimeric form of antibody may be used wherein the constant regions of the antibody are from a human. A humanized or fully human form of the antibody can also be prepared in accordance with methods well known in the art (see e. g. U.S. Pat. No. 5,565,332 to Winter). Humanization may be achieved by various methods including, but not limited to (a) grafting the non-human (e.g., donor antibody) CDRs onto human (e.g. recipient antibody) framework and constant regions with or without retention of critical framework residues (e.g. those that are important for retaining good antigen binding affinity or antibody functions), (b) grafting only the non-human specificity-determining regions (SDRs or a-CDRs; the residues critical for the antibody-antigen interaction) onto human framework and constant regions, or (c) transplanting the entire non-human variable domains, but "cloaking" them with a human-like section by replacement of surface residues. Humanized antibodies and methods of making them are reviewed, e.g., in Almagro and Fransson, Front Biosci 13, 1619-1633 (2008), and are further described, e.g., in Riechmann et al., Nature 332, 323-329 (1988); Queen et al., Proc Natl Acad Sci USA 86, 10029-10033 (1989); U.S. Pat. Nos. 5,821,337, 7,527,791, 6,982,321, and 7,087,409; Jones et al., Nature 321, 522-525 (1986); Morrison et al., Proc Natl Acad Sci 81, 6851-6855 (1984); Morrison and Oi, Adv Immunol 44, 65-92 (1988); Verhoeyen et al., Science 239, 1534-1536 (1988); Padlan, Molec Immun 31(3), 169-217 (1994); Kashmiri et al., Methods 36, 25-34 (2005) (describing SDR (a-CDR) grafting); Padlan, Mol Immunol 28, 489-498 (1991) (describing "resurfacing"); Dall'Acqua et al., Methods 36, 43-60 (2005) (describing "FR shuffling"); and Osbourn et al., Methods 36, 61-68 (2005) and Klimka et al., Br J Cancer 83, 252-260 (2000) (describing the "guided selection" approach to FR shuffling). Particular antibodies according to the invention are human antibodies. Human antibodies and human variable regions can be produced using various techniques known in the art. Human antibodies are described generally in van Dijk and van de Winkel, Curr Opin Pharmacol 5, 368-74 (2001) and Lonberg, Curr Opin Immunol 20, 450-459 (2008). Human variable regions can form part of and be derived from human monoclonal antibodies made by the hybridoma method (see e.g. Monoclonal Antibody Production Techniques and Applications, pp. 51-63 (Marcel Dekker, Inc., New York, 1987)). Human antibodies and human variable regions may also be prepared by administering an immunogen to a transgenic animal that has been modified to produce intact human antibodies or intact antibodies with human variable regions in response to antigenic challenge (see e.g. Lonberg, Nat Biotech 23, 1117-1125 (2005). Human antibodies and human variable regions may also be generated by isolating Fv clone variable region sequences selected from human-derived phage display libraries (see e.g., Hoogenboom et al. in Methods in Molecular Biology 178, 1-37 (O'Brien et al., ed., Human Press, Totowa, N.J., 2001); and McCafferty et al., Nature 348, 552-554; Clackson et al., Nature 352, 624-628 (1991)). Phage typically display antibody fragments, either as single-chain Fv (scFv) fragments or as Fab fragments. A detailed description of the preparation of antibodies by phage display can be found in the Examples appended to WO 2012/020006, which is incorporated herein by reference in its entirety.

In certain embodiments, the antibodies comprised in the fusion proteins of the present invention are engineered to have enhanced binding affinity according to, for example, the methods disclosed in PCT publication WO 2012/020006 (see Examples relating to affinity maturation) or U.S. Pat. Appl. Publ. No. 2004/0132066, the entire contents of which are hereby incorporated by reference. The ability of the antibody of the invention to bind to a specific antigenic determinant can be measured either through an enzyme-linked immunosorbent assay (ELISA) or other techniques familiar to one of skill in the art, e.g. surface plasmon resonance technique (Liljeblad, et al., Glyco J 17, 323-329 (2000)), and traditional binding assays (Heeley, Endocr Res 28, 217-229 (2002)). Competition assays may be used to identify an antibody that competes with a reference antibody for binding to a particular antigen, e.g. an antibody that competes with the 4G8 antibody for binding to FAP. In certain embodiments, such a competing antibody binds to the same epitope (e.g. a linear or a conformational epitope) that is bound by the reference antibody. Detailed exemplary methods for mapping an epitope to which an antibody binds are provided in Morris (1996) "Epitope Mapping Protocols", in Methods in Molecular Biology vol. 66 (Humana Press, Totowa, N.J.). In an exemplary competition assay, immobilized antigen (e.g. FAP) is incubated in a solution comprising a first labeled antibody that binds to the antigen (e.g. 4G8 antibody) and a second unlabeled antibody that is being tested for its ability to compete with the first antibody for binding to the antigen. The second antibody may be present in a hybridoma supernatant. As a control, immobilized antigen is incubated in a solution comprising the first labeled antibody but not the second unlabeled antibody. After incubation under conditions permissive for binding of the first antibody to the antigen, excess unbound antibody is removed, and the amount of label associated with immobilized antigen is measured. If the amount of label associated with immobilized antigen is substantially reduced in the test sample relative to the control sample, then that indicates that the second antibody is competing with the first antibody for binding to the antigen. See Harlow and Lane (1988) Antibodies: A Laboratory Manual ch. 14 (Cold Spring Harbor Laboratory, Cold Spring Harbor, N.Y.).

Fusion proteins prepared as described herein may be purified by art-known techniques such as high performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purification an antibody, ligand, receptor or antigen can be used to which the fusion protein binds. For example, for affinity chromatography purification of fusion proteins of the invention, a matrix with protein A or protein G may be used. Sequential Protein A or G affinity chromatography and size exclusion chromatography can be used to isolate a fusion protein essentially as described in the Examples. The purity of the fusion protein can be determined by any of a variety of well known analytical methods including gel electrophoresis, high pressure liquid chromatography, and the like. For example, the fusion proteins expressed as described in the Examples were shown to be intact and properly assembled as demonstrated by reducing and non-reducing SDS-PAGE (see e.g. FIGS. 2A-2D, FIGS. 5A-5D).

Compositions, Formulations, and Routes of Administration

In a further aspect, the invention provides pharmaceutical compositions comprising any of the fusion proteins provided herein, e.g., for use in any of the below therapeutic methods. In one embodiment, a pharmaceutical composition comprises any of the fusion proteins provided herein and a pharmaceutically acceptable carrier. In another embodiment, a pharmaceutical composition comprises any of the fusion proteins provided herein and at least one additional therapeutic agent, e.g. as described below.

Further provided is a method of producing a fusion protein of the invention in a form suitable for administration in vivo, the method comprising (a) obtaining a fusion protein according to the invention, and (b) formulating the fusion protein with at least one pharmaceutically acceptable carrier, whereby a preparation of fusion protein is formulated for administration in vivo.

Pharmaceutical compositions of the present invention comprise a therapeutically effective amount of one or more fusion protein dissolved or dispersed in a pharmaceutically acceptable carrier. The phrases "pharmaceutical or pharmacologically acceptable" refers to molecular entities and compositions that are generally non-toxic to recipients at the dosages and concentrations employed, i.e. do not produce an adverse, allergic or other untoward reaction when administered to an animal, such as, for example, a human, as appropriate. The preparation of a pharmaceutical composition that contains at least one fusion protein and optionally an additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards or corresponding authorities in other countries. Preferred compositions are lyophilized formulations or aqueous solutions. As used herein, "pharmaceutically acceptable carrier" includes any and all solvents, buffers, dispersion media, coatings, surfactants, antioxidants, preservatives (e.g. antibacterial agents, antifungal agents), isotonic agents, absorption delaying agents, salts, preservatives, antioxidants, proteins, drugs, drug stabilizers, polymers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The composition may comprise different types of carriers depending on whether it is to be administered in solid, liquid or aerosol form, and whether it need to be sterile for such routes of administration as injection. Fusion proteins of the present invention (and any additional therapeutic agent) can be administered intravenously, intradermally, intraarterially, intraperitoneally, intralesionally, intracranially, intraarticularly, intraprostatically, intrasplenically, intrarenally, intrapleurally, intratracheally, intranasally, intravitreally, intravaginally, intrarectally, intratumorally, intramuscularly, intraperitoneally, subcutaneously, subconjunctivally, intravesicularly, mucosally, intrapericardially, intraumbilically, intraocularly, orally, topically, locally, by inhalation (e.g. aerosol inhalation), injection, infusion, continuous infusion, localized perfusion bathing target cells directly, via a catheter, via a lavage, in cremes, in lipid compositions (e.g. liposomes), or by other method or any combination of the forgoing as would be known to one of ordinary skill in the art (see, for example, Remington's Pharmaceutical Sciences, 18th Ed. Mack Printing Company, 1990, incorporated herein by reference). Parenteral administration, in particular intravenous injection, is most commonly used for administering polypeptide molecules such as the fusion proteins of the invention.

Parenteral compositions include those designed for administration by injection, e.g. subcutaneous, intradermal, intralesional, intravenous, intraarterial intramuscular, intrathecal or intraperitoneal injection. For injection, the fusion proteins of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. Alternatively, the fusion proteins may be in powder form for constitution with a suitable vehicle, e.g., sterile pyrogen-free water, before use. Sterile injectable solutions are prepared by incorporating the fusion proteins of the invention in the required amount in the appropriate solvent with various of the other ingredients enumerated below, as required. Sterility may be readily accomplished, e.g., by filtration through sterile filtration membranes. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein. Suitable pharmaceutically acceptable carriers include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Aqueous injection suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions. Additionally, suspensions of the active compounds may be prepared as appropriate oily injection suspensions. Suitable lipophilic solvents or vehicles include fatty oils such as sesame oil, or synthetic fatty acid esters, such as ethyl cleats or triglycerides, or liposomes.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (18th Ed. Mack Printing Company, 1990). Sustained-release preparations may be prepared. Suitable examples of sustained-release preparations include semipermeable matrices of solid hydrophobic polymers containing the polypeptide, which matrices are in the form of shaped articles, e.g. films, or microcapsules. In particular embodiments, prolonged absorption of an injectable composition can be brought about by the use in the compositions of agents delaying absorption, such as, for example, aluminum monostearate, gelatin or combinations thereof.

In addition to the compositions described previously, the fusion proteins may also be formulated as a depot preparation. Such long acting formulations may be administered by implantation (for example subcutaneously or intramuscularly) or by intramuscular injection. Thus, for example, the fusion proteins may be formulated with suitable polymeric or hydrophobic materials (for example as an emulsion in an acceptable oil) or ion exchange resins, or as sparingly soluble derivatives, for example, as a sparingly soluble salt.

Pharmaceutical compositions comprising the fusion proteins of the invention may be manufactured by means of conventional mixing, dissolving, emulsifying, encapsulating, entrapping or lyophilizing processes. Pharmaceutical compositions may be formulated in conventional manner using one or more physiologically acceptable carriers, diluents, excipients or auxiliaries which facilitate processing of the proteins into preparations that can be used pharmaceutically. Proper formulation is dependent upon the route of administration chosen.

The fusion proteins may be formulated into a composition in a free acid or base, neutral or salt form. Pharmaceutically acceptable salts are salts that substantially retain the biological activity of the free acid or base. These include the acid addition salts, e.g. those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Pharmaceutical salts tend to be more soluble in aqueous and other protic solvents than are the corresponding free base forms.

Therapeutic Methods and Compositions

Any of the fusion proteins provided herein may be used in therapeutic methods.

For use in therapeutic methods, fusion proteins of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

In one aspect, fusion proteins of the invention for use as a medicament are provided. In further aspects, fusion proteins of the invention for use in treating a disease are provided. In certain embodiments, fusion proteins of the invention for use in a method of treatment are provided. In one embodiment, the invention provides a fusion protein as described herein for use in the treatment of a disease in an individual in need thereof. In certain embodiments, the invention provides a fusion protein for use in a method of treating an individual having a disease comprising administering to the individual a therapeutically effective amount of the fusion protein. In certain embodiments the disease to be treated is an inflammatory disease. Exemplary inflammatory diseases include inflammatory bowel disease (e.g. Crohn's disease or ulcerative colitis) and rheumatoid arthritis. In a particular embodiment the disease is inflammatory bowel disease or rheumatoid arthritis, particularly inflammatory bowel disease, more particularly Crohn's disease or ulcerative colitis. In certain embodiments the method further comprises administering to the individual a therapeutically effective amount of at least one additional therapeutic agent, e.g., an anti-inflammatory agent if the disease to be treated is an inflammatory disease. An "individual" according to any of the above embodiments is a mammal, preferably a human.

In a further aspect, the invention provides for the use of a fusion protein of the invention in the manufacture or preparation of a medicament for the treatment of a disease in an individual in need thereof. In one embodiment, the medicament is for use in a method of treating a disease comprising administering to an individual having the disease a therapeutically effective amount of the medicament. In certain embodiments the disease to be treated is an inflammatory disease. In a particular embodiment the disease is inflammatory bowel disease or rheumatoid arthritis, particularly inflammatory bowel disease, more particularly Crohn's disease or ulcerative colitis. In one embodiment, the method further comprises administering to the individual a therapeutically effective amount of at least one additional therapeutic agent, e.g., an anti-inflammatory agent if the disease to be treated is an inflammatory disease. An "individual" according to any of the above embodiments may be a mammal, preferably a human.

In a further aspect, the invention provides a method for treating a disease in an individual, comprising administering to said individual a therapeutically effective amount of a fusion protein of the invention. In one embodiment a composition is administered to said individual, comprising a fusion protein of the invention in a pharmaceutically acceptable form. In certain embodiments the disease to be treated is an inflammatory disease. In a particular embodiment the disease is inflammatory bowel disease or rheumatoid arthritis, particularly inflammatory bowel disease, more particularly Crohn's disease or ulcerative colitis. In certain embodiments the method further comprises administering to the individual a therapeutically effective amount of at least one additional therapeutic agent, e.g. an anti-inflammatory agent if the disease to be treated is an inflammatory disease. An "individual" according to any of the above embodiments may be a mammal, preferably a human.

The fusion proteins of the invention are also useful as diagnostic reagents. The binding of a fusion proteins to an antigenic determinant can be readily detected e.g. by a label attached to the fusion protein or by using a labeled secondary antibody specific for the fusion protein of the invention.

In some embodiments, an effective amount of a fusion protein of the invention is administered to a cell. In other embodiments, a therapeutically effective amount of a fusion protein of the invention is administered to an individual for the treatment of disease.

For the prevention or treatment of disease, the appropriate dosage of a fusion protein of the invention (when used alone or in combination with one or more other additional therapeutic agents) will depend on the type of disease to be treated, the route of administration, the body weight of the patient, the type of fusion protein, the severity and course of the disease, whether the fusion protein is administered for preventive or therapeutic purposes, previous or concurrent therapeutic interventions, the patient's clinical history and response to the fusion protein, and the discretion of the attending physician. The practitioner responsible for administration will, in any event, determine the concentration of active ingredient(s) in a composition and appropriate dose(s) for the individual subject. Various dosing schedules including but not limited to single or multiple administrations over various time-points, bolus administration, and pulse infusion are contemplated herein.

The fusion protein is suitably administered to the patient at one time or over a series of treatments. Depending on the type and severity of the disease, about 1 μg/kg to 15 mg/kg (e.g. 0.1 mg/kg-10 mg/kg) of fusion protein can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of the fusion protein would be in the range from about 0.005 mg/kg to about 10 mg/kg. In other non-limiting examples, a dose may also comprise from about 1 μg/kg body weight, about 5 μg/kg body weight, about 10 μg/kg body weight, about 50 μg/kg body weight, about 100 μg/kg body weight, about 200 µg/kg body weight, about 350 µg/kg body weight, about 500 µg/kg body weight, about 1 mg/kg body weight, about 5 mg/kg body weight, about 10 mg/kg body weight, about 50 mg/kg body weight, about 100 mg/kg body weight, about 200 mg/kg body weight, about 350 mg/kg body weight, about 500 mg/kg body weight, to about 1000 mg/kg body weight or more per administration, and any range derivable therein. In non-limiting examples of a derivable range from the numbers listed herein, a range of about 5 mg/kg body weight to about 100 mg/kg body weight, about 5 µg/kg body weight to about 500 mg/kg body weight etc., can be administered, based on the numbers described above. Thus, one or more doses of about 0.5 mg/kg, 2.0 mg/kg, 5.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the fusion protein). An initial higher loading dose, followed by one or more lower doses may be administered. However, other dosage regimens may be useful. The progress of this therapy is easily monitored by conventional techniques and assays.

The fusion proteins of the invention will generally be used in an amount effective to achieve the intended purpose. For use to treat or prevent a disease condition, the fusion proteins of the invention, or pharmaceutical compositions thereof, are administered or applied in a therapeutically effective amount. Determination of a therapeutically effective amount is well within the capabilities of those skilled in the art, especially in light of the detailed disclosure provided herein.

For systemic administration, a therapeutically effective dose can be estimated initially from in vitro assays, such as cell culture assays. A dose can then be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the fusion proteins which are sufficient to maintain therapeutic effect. Usual patient dosages for administration by injection range from about 0.1 to 50 mg/kg/day, typically from about 0.5 to 1 mg/kg/day. Therapeutically effective plasma levels may be achieved by administering multiple doses each day. Levels in plasma may be measured, for example, by HPLC.

In cases of local administration or selective uptake, the effective local concentration of the fusion protein may not be related to plasma concentration. One having skill in the art will be able to optimize therapeutically effective local dosages without undue experimentation.

A therapeutically effective dose of the fusion proteins described herein will generally provide therapeutic benefit without causing substantial toxicity. Toxicity and therapeutic efficacy of a fusion protein can be determined by standard pharmaceutical procedures in cell culture or experimental animals. Cell culture assays and animal studies can be used to determine the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LD_{50}/ED_{50}$. Fusion proteins that exhibit large therapeutic indices are preferred. In one embodiment, the fusion protein according to the present invention exhibits a high therapeutic index. The data obtained from cell culture assays and animal studies can be used in formulating a range of dosages suitable for use in humans. The dosage lies preferably within a range of circulating concentrations that include the $ED_{50}$ with little or no toxicity. The dosage may vary within this range depending upon a variety of factors, e.g., the dosage form employed, the route of administration utilized, the condition of the subject, and the like. The exact formulation, route of administration and dosage can be chosen by the individual physician in view of the patient's condition (see, e.g., Fingl et al., 1975, in: The Pharmacological Basis of Therapeutics, Ch. 1, p. 1, incorporated herein by reference in its entirety).

The attending physician for patients treated with fusion proteins of the invention would know how and when to terminate, interrupt, or adjust administration due to toxicity, organ dysfunction, and the like. Conversely, the attending physician would also know to adjust treatment to higher levels if the clinical response were not adequate (precluding toxicity). The magnitude of an administered dose in the management of the disorder of interest will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient.

Other Agents and Treatments

The fusion proteins of the invention may be administered in combination with one or more other agents in therapy. For instance, a fusion protein of the invention may be co-administered with at least one additional therapeutic agent. The term "therapeutic agent" encompasses any agent administered to treat a symptom or disease in an individual in need of such treatment. Such additional therapeutic agent may comprise any active ingredients suitable for the particular indication being treated, preferably those with complementary activities that do not adversely affect each other. In certain embodiments, an additional therapeutic agent is an anti-inflammatory agent.

Such other agents are suitably present in combination in amounts that are effective for the purpose intended. The effective amount of such other agents depends on the amount of fusion protein used, the type of disorder or treatment, and other factors discussed above. The fusion proteins are generally used in the same dosages and with administration routes as described herein, or about from 1 to 99% of the dosages described herein, or in any dosage and by any route that is empirically/clinically determined to be appropriate.

Such combination therapies noted above encompass combined administration (where two or more therapeutic agents are included in the same or separate compositions), and separate administration, in which case, administration of the fusion protein of the invention can occur prior to, simultaneously, and/or following, administration of the additional therapeutic agent and/or adjuvant.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic.

The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is a fusion protein of the invention. The label or package insert indicates that the composition is used for treating the condition of choice. Moreover, the article of manufacture may comprise (a) a first container with a composition contained therein, wherein the composition comprises an fusion protein of the invention; and (b) a second container with a composition contained therein, wherein the composition comprises a further therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Examples

The following are examples of methods and compositions of the invention. It is understood that various other embodiments may be practiced, given the general description provided above.

Recombinant DNA Techniques

Standard methods were used to manipulate DNA as described in Sambrook et al., Molecular cloning: A laboratory manual; Cold Spring Harbor Laboratory Press, Cold Spring Harbor, N.Y., 1989. The molecular biological reagents were used according to the manufacturer's instructions. DNA sequences were determined by double strand sequencing. General information regarding the nucleotide sequences of human immunoglobulins light and heavy chains is given in: Kabat, E. A. et al., (1991) Sequences of Proteins of Immunological Interest, Fifth Ed., NIH Publication No 91-3242.

Gene Synthesis

Desired gene segments were either generated by PCR using appropriate templates or synthesized at Geneart AG (Regensburg, Germany) from synthetic oligonucleotides and PCR products by automated gene synthesis. The gene segments flanked by singular restriction endonuclease cleavage sites were cloned into standard cloning/sequencing vectors. The plasmid DNA was purified from transformed bacteria and the concentration determined by UV spectroscopy. The DNA sequences of the subcloned gene fragments were confirmed by DNA sequencing. Gene segments were designed with suitable restriction sites to allow subcloning into the respective expression vectors. All constructs were designed with a 5'-end DNA sequence coding for a leader peptide (MGWSCIILFLVATATGVHS) which targets proteins for secretion in eukaryotic cells.

Cloning of Antibody-IL-10 Fusion Constructs

The amplified DNA fragments of heavy and light chain V-domains were inserted in frame either into the human IgG$_1$ or the Fab constant heavy chain or the human constant light chain containing respective recipient mammalian expression vector. Heavy chains and light chains were always encoded on separate plasmids. Whereas the plasmids coding for the light chains are identical for IgG-based and Fab-based IL-10 fusion constructs, the plasmids encoding the heavy chains for the Fab-based constructs contain, depending on the format, one or two VH-CH1 domains alongside with the respective IL-10 portion. In the case where the Fab heavy chain plasmid comprises two VH-CH1 domains (tandem Fab intermitted by a single chain IL-10 dimer or by an engineered monomeric IL-10 (Josephson et al., J Biol Chem 275, 13552-7 (2000)), the two V-domains had to be inserted in a two-step cloning procedure using different combinations of restriction sites for each of them. The IL-10 portions of these constructs were always cloned in frame with the heavy chains of these antibodies using a $(G_4S)_3$ 15-mer linker between the C-terminus of the Fab or IgG heavy chain and the N-terminus of the cytokine, respectively. Only the IgG-IL-10 format (FIG. 1A) comprises a $(G_4S)_4$ 20-mer linker between the C-terminus of the IgG heavy chain and the N-terminus of the cytokine. The C-terminal lysine residue of the IgG heavy chain was removed upon addition of the connector. For the single chain IL-10, a $(G_4S)_4$ 20-mer linker was inserted between the two IL-10 chains. In the case of two different IgG heavy chains with only one of them fused to IL-10, two heavy chain plasmids needed to be constructed and transfected for heterodimerization facilitated by a knob-into-hole modification in the IgG CH3 domains. The "hole" heavy chain connected to the IL-10 portion carried the Y349C, T366S, L368A and Y407V mutations in the CH3 domain, whereas the unfused "knob" heavy chain carried the S354C and T366W mutations in the CH3 domain (EU numbering). To abolish FcγR binding/effector function and prevent FcR co-activation, the following mutations were introduced into the CH2 domain of each of the IgG heavy chains: L234A, L235A and P329G (EU numbering). The expression of the antibody-IL-10 fusion constructs was driven by an MPSV promoter and transcription was terminated by a synthetic polyA signal sequence located downstream of the CDS. In addition to the expression cassette, each vector contained an EBV oriP sequence for autonomous replication in EBV-EBNA expressing cell lines.

Preparation of Antibody-IL-10 Fusion Proteins

Details about the generation, affinity maturation and characterization of antigen binding moieties directed to FAP can be found in the Examples (particularly Example 2-6 (preparation) and 7-13 (characterization)) appended to PCT publication no. WO 2012/020006, which is incorporated herein by reference in its entirety. As described therein, various antigen binding domains directed to FAP have been generated by phage display, including the ones designated 4G8 and 4B9 used in the following examples.

Antibody IL-10 fusion constructs as used in the examples were produced by co-transfecting exponentially growing HEK293-EBNA cells with the mammalian expression vectors using a calcium phosphate-transfection. Alternatively, HEK293 EBNA cells growing in suspension were transfected by polyethylenimine (PEI) with the expression vectors. All FAP-targeting antibody-IL-10 fusion constructs based on clones 4G8 and 4B9 can be purified by affinity chromatography using a protein A matrix.

Briefly, FAP-targeted constructs fused to IL-10, single chain (sc) IL-10 or IL-10M1 were purified by a method composed of one affinity chromatography step (protein A) followed by size exclusion chromatography (Superdex 200, GE Healthcare). The protein A column was equilibrated in 20 mM sodium phosphate, 20 mM sodium citrate pH 7.5, supernatant was loaded, and the column was washed with 20 mM sodium phosphate, 20 mM sodium citrate (optionally with or without 500 mM sodium chloride), pH 7.5, followed by a wash with 13.3 mM sodium phosphate, 20 mM sodium citrate, 500 mM sodium chloride, pH 5.45 in case FBS was present in the supernatant. A third wash with 10 mM IVIES, 50 mM sodium chloride pH 5 was optionally performed. The fusion constructs were eluted with 20 mM sodium citrate, 100 mM sodium chloride, 100 mM glycine, pH 3. The eluted fractions were pooled and polished by size exclusion chromatography in the final formulation buffer which was either 25 mM potassium phosphate, 125 mM sodium chloride, 100 mM glycine pH 6.7 or 20 mM histidine, 140 mM NaCl pH6.0.

The protein concentration of purified antibody-IL-10 fusion constructs was determined by measuring the optical density (OD) at 280 nm, using the molar extinction coefficient calculated on the basis of the amino acid sequence. Purity, integrity and monomeric state of the fusion constructs were analyzed by SDS-PAGE in the presence and absence of a reducing agent (5 mM 1,4-dithiotreitol) and stained with Coomassie blue (SimpleBlue™ SafeStain, Invitrogen). The NuPAGE® Pre-Cast gel system (Invitrogen) was used according to the manufacturer's instructions (4-20% Tris-glycine gels or 3-12% Bis-Tris). Alternatively, reduced and non-reduced antibody-IL-10 fusion constructs were analyzed using a LabChip GX (Caliper) according to manufacturer's specifications. The aggregate content of immunoconjugate samples was analyzed using a Superdex 200 10/300GL analytical size-exclusion column (GE Healthcare) with 2 mM MOPS, 150 mM NaCl, 0.02% $NaN_3$, pH 7.3 running buffer, or a TSKgel G3000 SW XL column in 25 mM K2HPO4, 125 mM NaCl, 200 mM arginine, 0.02% NaN3, pH 6.7 running buffer at 25° C.

Figure 6A:
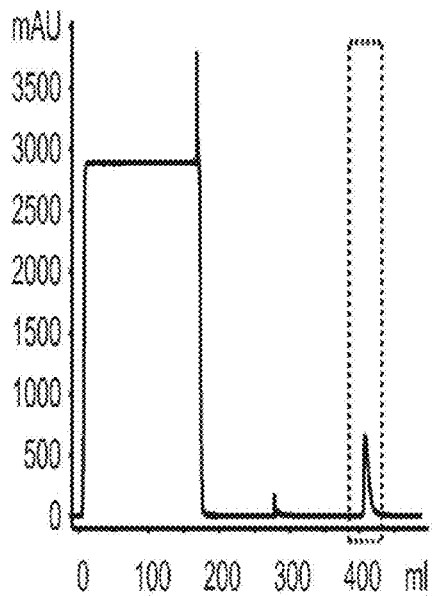
FIGS. 6A-6D Purification of FAP-targeted 4B9-based Fab-IL-10 construct (see SEQ ID NOs 25 and 31).
Figure 6B:
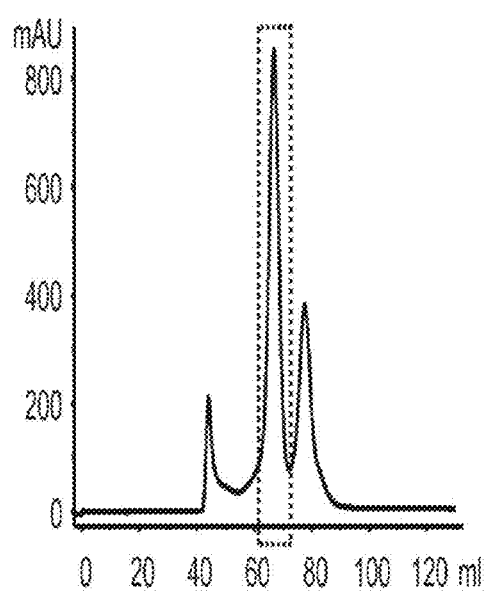
Figure 6C:
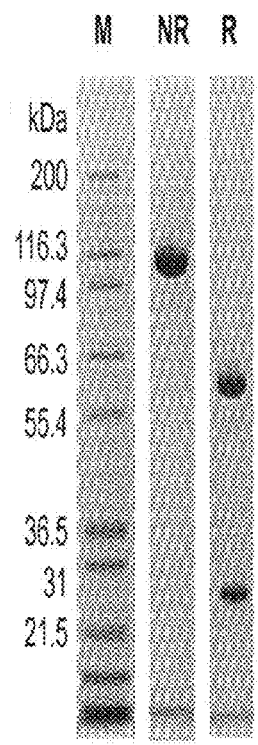
Figure 6D:
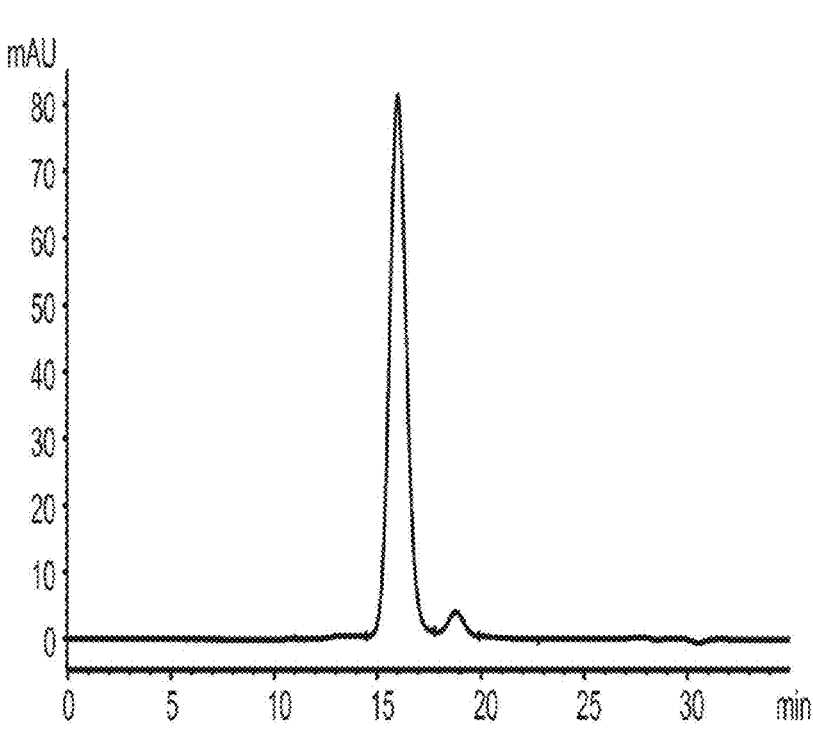
Figure 7A:
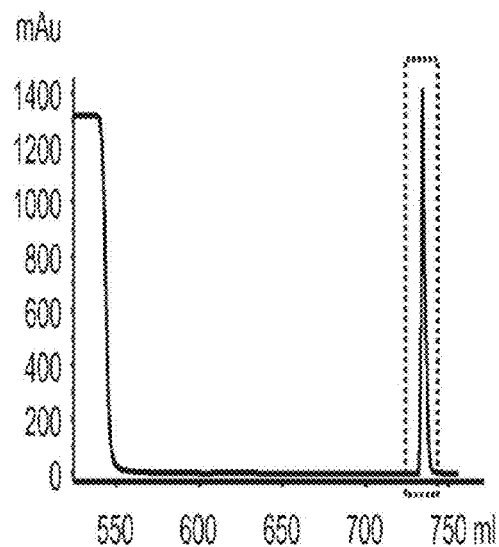
FIGS. 7A-7D Purification of FAP-targeted 4G8-based Fab-scIL-10-Fab construct (see SEQ ID NOs 7 and 21).
Figure 7B:
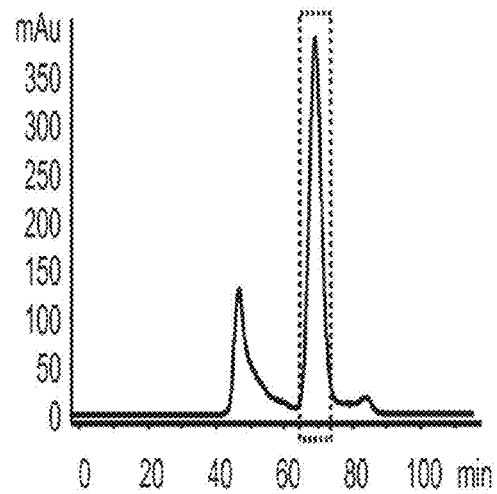
Figure 7C:
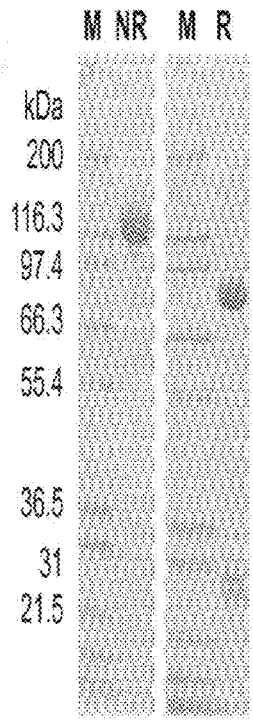
Figure 7D:
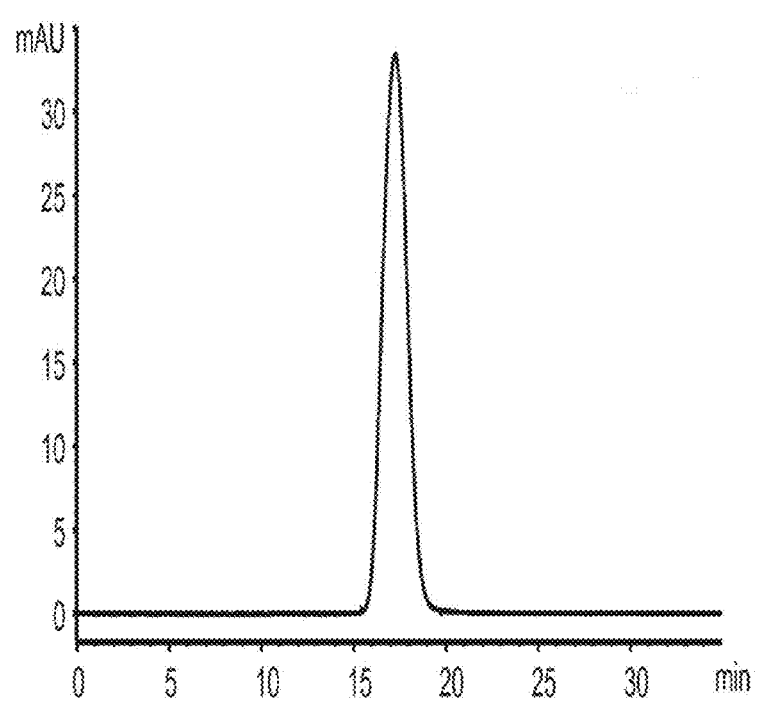
Figure 8A:
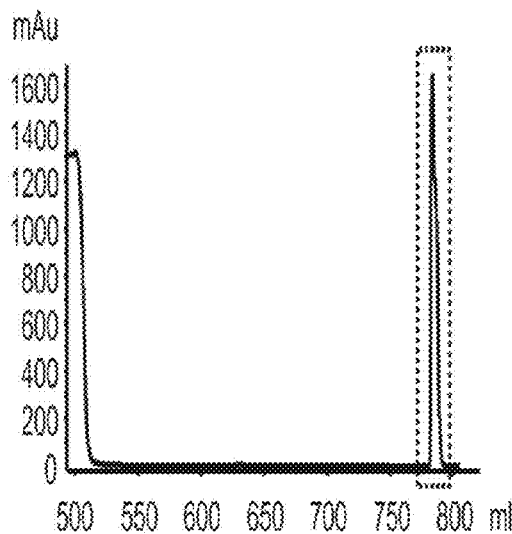
FIGS. 8A-8D Purification of FAP-targeted 4G8-based Fab-IL-10M1-Fab fusion (see SEQ ID NOs 7 and 23).
Figure 8B:
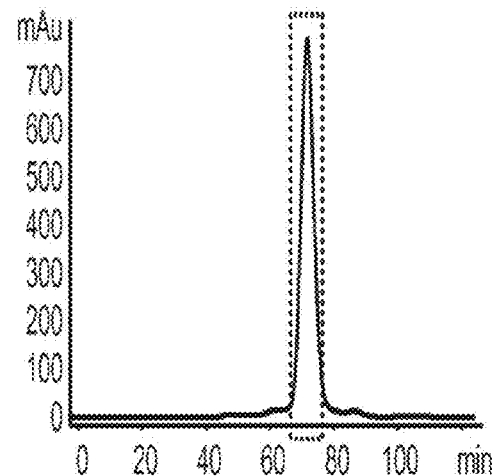
Figure 8C:
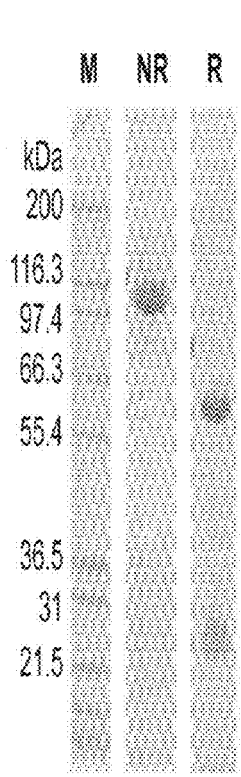
Figure 8D:
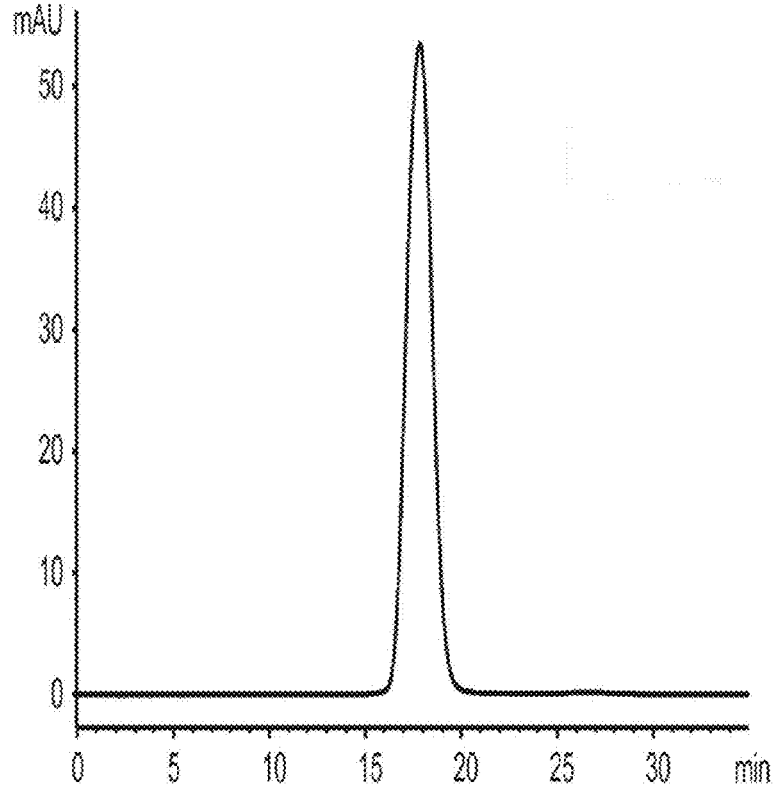

Results of the purifications and subsequent analysis for the different constructs are shown in FIGS. 2A-2D, FIGS. 3A-3D, FIGS. 4A-4D, FIGS. 5A-5D, FIGS. 6A-6D, FIGS. 7A-7D, 8A-8D. The IgG-IL-10 construct exhibited several production advantages over the other IL-10 fusion formats. Firstly, in comparison to the Fab-IL-10 format, the IL-10 homodimer is anchored within the same antibody molecule. Consequently, upon production, no monomeric IL-10 molecules can occur as seen for the Fab-IL-10 format for which after affinity chromatography, monomeric and dimeric protein species were observed with only the dimer being the desired active product (compare FIG. 2B and FIG. 6B). Secondly, in contrast to heterodimeric IgG-based formats comprising a knob-into-hole modification (e.g. IgG-scIL-10 and IgG-IL-10M1), the IgG-IL-10 construct comprises two identical heavy chains. This avoids undesired byproducts like hole-hole or knob-knob homodimers.

Affinity-Determination by SPR

Figure 9A:
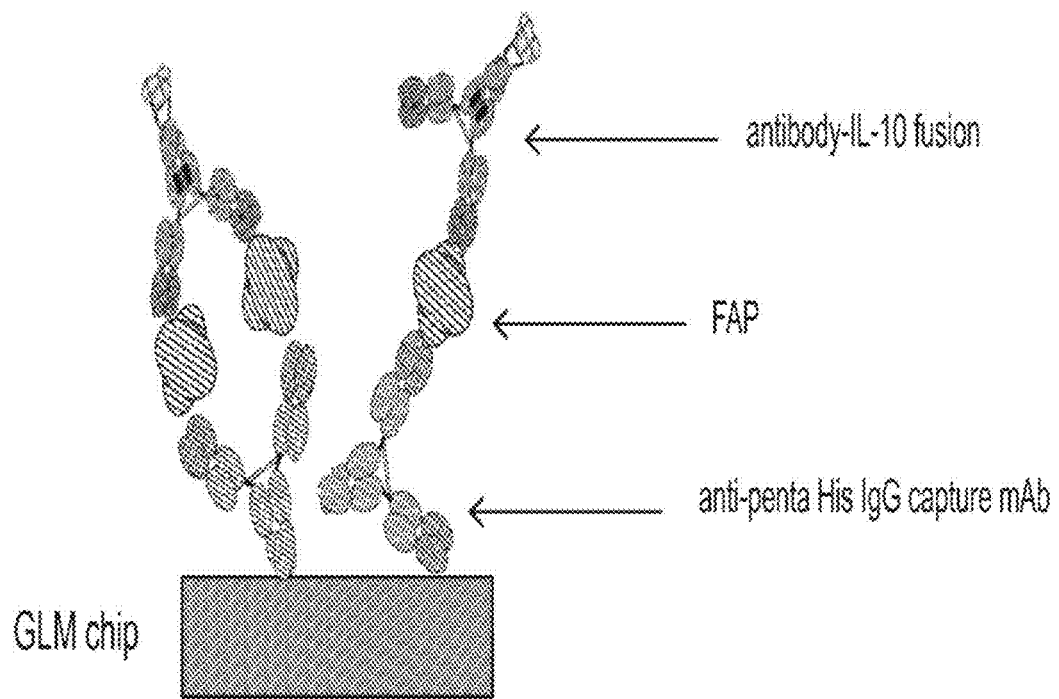
FIGS. 9A-9B SPR assay set-up on ProteOn XPR36.

Kinetic rate constants ($k_{on}$ and $k_{off}$) as well as affinity ($K_D$) of antibody-IL-10 fusion constructs to FAP from three different species (human, murine and cynomolgus) and to human IL-10R1 were measured by surface plasmon resonance (SPR) using a ProteOn XPR36 (BioRad) instrument with PB ST running buffer (10 mM phosphate, 150 mM sodium chloride pH 7.4, 0.005% Tween 20) at 25° C. To determine the affinities to FAP, the target protein was captured via its H6-tag by a covalently immobilized anti-H6 antibody (FIG. 9A). Briefly, anti-penta His IgG (Qiagen #34660, mouse monoclonal antibody) was immobilized at high levels (up to ~5.000 RU) at 30 μl/min onto separate vertical channels of a GLM chip by simultaneously activating all channels for 5 min with a freshly prepared mixture of 1-ethyl-3-(3-dimethylaminopropyl)-carboiimide (EDC) and N-hydroxysuccinimide (sNHS), subsequently injecting 15 μg/ml anti-penta His IgG in 10 mM sodium acetate buffer pH 4.5 for 180 sec. Channels were blocked using a 5-min injection of ethanolamine. H6-tagged FAP from different species (see SEQ ID NOs 81, 83 and 85) was captured from a 5 μg/ml dilution in running buffer along the vertical channels for 60 s at 30 μl/min to achieve ligand densities between ~250 and 600 RU. In a one-shot kinetic assay set-up (OSK), antibody-IL-10 fusion constructs were injected as analytes along the horizontal channels in a five-fold dilution series ranging from 50 to 0.08 nM at 100 μl/min. Association phase was recorded for 180 s, dissociation phase for 600 s. In case of interactions exhibiting very slow off-rates, recording of off-rates was extended up to 1800 s in order to observe the dissociation of the complex. However, in some instances, fitting of these off-rates was still not possible so an estimate of $1 \times 10^{-5}$ l/s was used for calculation of $K_D$. Running buffer (PBST) was injected along the sixth channel to provide an "in-line" blank for referencing. Association rates ($k_{on}$) and dissociation rates ($k_{off}$) were calculated using a simple 1:1 Langmuir binding model (ProteOn Manager software version 2.1) by simultaneously fitting the association and dissociation sensorgrams. The equilibrium dissociation constant ($K_D$) was calculated as the ratio $k_{off}/k_{on}$. Regeneration was performed by two pulses of 10 mM glycine pH 1.5 and 50 mM NaOH for 30 s at 100 μl/min in the horizontal orientation to dissociate the anti-penta His IgG from captured FAP and bound antibody-IL-10 fusion constructs.

Figure 9B:
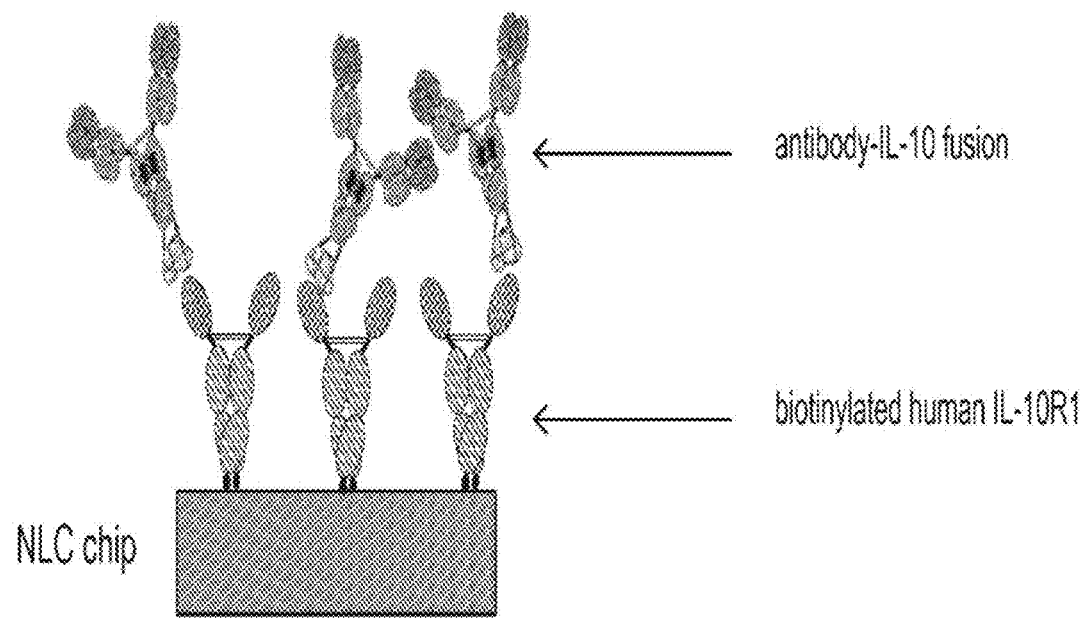

To measure the interaction between the antibody-IL-10 fusion constructs and the human IL-10R1, an NLC chip was used for immobilization of the biotinylated receptor (FIG. 9B). Between 400 and 1600 RU of human IL-10R1 (see SEQ ID NO: 87) were captured on the neutravidin-derivatized chip matrix along vertical channels at a concentration of 10 μg/ml and a flow rate of 30 μl/sec for varying contact times. Binding to biotinylated human IL10R1 was measured at six different analyte concentrations (50, 10, 2, 0.4, 0.08, 0 nM) by injections in horizontal orientation at 100 μl/min, recording the association rate for 180 s, the dissociation rate for 600 s. Running buffer (PBST) was injected along the sixth channel to provide an "in-line" blank for referencing. Association rates ($k_{on}$) and dissociation rates ($k_{off}$) were calculated using a simple 1:1 Langmuir binding model (ProteOn Manager software version 2.1) by simultaneously fitting the association and dissociation sensorgrams. The equilibrium dissociation constant ($K_D$) was calculated as the ratio $k_{off}/k_{on}$. As human IL-10R1 could not be regenerated without a loss of activity, the two subsequent steps of ligand capture and analyte injection were performed channel per channel using a freshly immobilized sensorchip surface for every interaction.

Table 1 and 2 show a summary of kinetic rate and equilibrium constants for antibody-IL-10 fusion constructs based on anti-FAP clone 4G8 or 4B9, respectively, binding to FAP from different species and to human IL-10R1.

TABLE 1

Summary of kinetic rate and equilibrium constants for antibody fusions based on anti-FAP clone 4G8. Binding to FAP from different species and to human IL-10R1.

| 4G8 | hu IL-10R1 ($k_{on}$, $k_{off}$, $K_D$) | hu FAP ($k_{on}$, $k_{off}$, $K_D$) | mu FAP ($k_{on}$, $k_{off}$, $K_D$) | cyno FAP ($k_{on}$, $k_{off}$, $K_D$) |
|---|---|---|---|---|
| IgG-IL-10 | $9.96 \times 10^5$ 1/Ms<br>$2.46 \times 10^{-5}$ 1/s<br>$2.47 \times 10^{-11}$ M | $3.04 \times 10^6$ 1/Ms<br>$1.24 \times 10^{-4}$ 1/s<br>$4.07 \times 10^{-11}$ M | $1.55 \times 10^6$ 1/Ms<br>$1.00 \times 10^{-5}$ 1/s est.<br>$6.45 \times 10^{-12}$ M | $3.66 \times 10^6$ 1/Ms<br>$1.06 \times 10^{-4}$ 1/s<br>$2.90 \times 10^{-11}$ M |
| IgG-scIL-10 | n.d. because of heterogeneity of protein | n.d. because of heterogeneity of protein | n.d. because of heterogeneity of protein | n.d. because of heterogeneity of protein |
| IgG-IL-10M1 | $3.64 \times 10^5$ 1/Ms<br>$2.96 \times 10^{-4}$ 1/s<br>$8.15 \times 10^{-10}$ M | $2.26 \times 10^6$ 1/Ms<br>$7.93 \times 10^{-5}$ 1/s<br>$3.52 \times 10^{-11}$ M | $1.99 \times 10^6$ 1/Ms<br>$1.00 \times 10^{-5}$ 1/s est.<br>$5.03 \times 10^{-12}$ M | $3.75 \times 10^6$ 1/Ms<br>$1.28 \times 10^{-4}$ 1/s<br>$3.41 \times 10^{-11}$ M |
| IgG-(IL-10M1)$_2$ | 1.58E+06 1/Ms<br>$3.79 \times 10^{-5}$ 1/s<br>$2.40 \times 10^{-11}$ M | $3.09 \times 10^6$ 1/Ms<br>$7.76 \times 10^{-5}$ 1/s<br>$2.51 \times 10^{-11}$ M | $1.70 \times 10^6$ 1/Ms<br>$1.12 \times 10^{-5}$ 1/s<br>$6.57 \times 10^{-12}$ M | $3.45 \times 10^6$ 1/Ms<br>$1.80 \times 10^{-4}$ 1/s<br>$5.21 \times 10^{-11}$ M |
| Fab-IL-10 | $1.32 \times 10^6$ 1/Ms<br>$8.23 \times 10^{-5}$ 1/s<br>$6.24 \times 10^{-11}$ M | $3.24 \times 10^6$ 1/Ms<br>$1.69 \times 10^{-4}$ 1/s<br>$5.21 \times 10^{-11}$ M | $1.77 \times 10^6$ 1/Ms<br>$1.00 \times 10^{-5}$ 1/s est.<br>$5.65 \times 10^{-12}$ M | $3.55 \times 10^6$ 1/Ms<br>$1.29 \times 10^{-4}$ 1/s<br>$3.64 \times 10^{-11}$ M |
| Fab-scIL-10-Fab | $1.30 \times 10^6$ 1/Ms<br>$9.55 \times 10^{-5}$ 1/s<br>$7.33 \times 10^{-11}$ M | $4.01 \times 10^6$ 1/Ms<br>$2.18 \times 10^{-4}$ 1/s<br>$5.43 \times 10^{-11}$ M | $1.80 \times 10^6$ 1/Ms<br>$1.00 \times 10^{-5}$ 1/s est.<br>$5.56 \times 10^{-12}$ M | $4.03 \times 10^6$ 1/Ms<br>$2.19 \times 10^{-4}$ 1/s<br>$5.44 \times 10^{-11}$ M |
| Fab-IL-10M1-Fab | $3.7 \times 10^5$ 1/Ms<br>$4.2 \times 10^{-4}$ 1/s<br>$1.1 \times 10^{-9}$ M | $3.66 \times 10^6$ 1/Ms<br>$2.04 \times 10^{-4}$ 1/s<br>$5.57 \times 10^{-11}$ M | $1.52 \times 10^6$ 1/Ms<br>$1.00 \times 10^{-5}$ 1/s est.<br>$5.58 \times 10^{-12}$ M | $3.84 \times 10^6$ 1/Ms<br>$2.42 \times 10^{-4}$ 1/s<br>$6.29 \times 10^{-11}$ M |

TABLE 2

Summary of kinetic rate and equilibrium constants for antibody fusions based on anti-FAP clone 4B9. Binding to FAP from different species and to human IL-10R1.

| 4B9 | hu IL-10R1 ($k_{on}$, $k_{off}$, $K_D$) | hu FAP ($k_{on}$, $k_{off}$, $K_D$) | mu FAP ($k_{on}$, $k_{off}$, $K_D$) | cyno FAP ($k_{on}$, $k_{off}$, $K_D$) |
|---|---|---|---|---|
| IgG-IL-10 | $8.24 \times 10^5$ 1/Ms<br>$3.91 \times 10^{-5}$ 1/s<br>$4.75 \times 10^{-11}$ M | $3.81 \times 10^6$ 1/Ms<br>$4.03 \times 10^{-5}$ 1/s<br>$1.06 \times 10^{-11}$ M | $2.12 \times 10^6$ 1/Ms<br>$1.24 \times 10^{-4}$ 1/s<br>$5.83 \times 10^{-11}$ M | $5.47 \times 10^6$ 1/Ms<br>$2.86 \times 10^{-5}$ 1/s<br>$5.22 \times 10^{-12}$ M |
| IgG-(IL-10M1)$_2$ | $1.80 \times 10^6$ 1/Ms<br>$3.39 \times 10^{-5}$ 1/s<br>$1.88 \times 10^{-11}$ M | $5.80 \times 10^6$ 1/Ms<br>$9.73 \times 10^{-5}$ 1/s<br>$1.68 \times 10^{-11}$ M | $2.97 \times 10^6$ 1/Ms<br>$1.09 \times 10^{-4}$ 1/s<br>$3.69 \times 10^{-11}$ M | $6.40 \times 10^6$ 1/Ms<br>$7.77 \times 10^{-5}$ 1/s<br>$1.21 \times 10^{-11}$ M |
| Fab-IL-10 | $2.15 \times 10^6$ 1/Ms<br>$4.57 \times 10^{-5}$ 1/s<br>$2.12 \times 10^{-11}$ M | $5.47 \times 10^6$ 1/Ms<br>$5.72 \times 10^{-6}$ 1/s<br>$1.05 \times 10^{-12}$ M | $2.68 \times 10^6$ 1/Ms<br>$6.27 \times 10^{-5}$ 1/s<br>$2.34 \times 10^{-11}$ M | $4.16 \times 10^6$ 1/Ms<br>$7.27 \times 10^{-5}$ 1/s<br>$1.75 \times 10^{-11}$ M |
| Fab-scIL-10-Fab | $1.73 \times 10^6$ 1/Ms<br>$9.58 \times 10^{-5}$ 1/s<br>$5.53 \times 10^{-11}$ M | $4.74 \times 10^6$ 1/Ms<br>$3.11 \times 10^{-5}$ 1/s<br>$6.56 \times 10^{-12}$ M | $2.45 \times 10^6$ 1/Ms<br>$7.40 \times 10^{-5}$ 1/s<br>$3.03 \times 10^{-11}$ M | $4.93 \times 10^6$ 1/Ms<br>$3.35 \times 10^{-5}$ 1/s<br>$6.79 \times 10^{-12}$ M |

Wild type (wt) IL-10 cytokine, not fused to an antibody but C-terminally H6-tagged, in our hands showed a $K_D$ of 52 pM for human IL-10R1 ($k_{on}$ $2.5 \times 10^6$ 1/Ms, $k_{off}$ $1.3 \times 10^{-4}$ 1/s). For the antibody-IL-10 fusion constructs based on the dimeric cytokine, the avidities to IL-10R1 were comparable to the unfused cytokine and also two-digit pM (ranging from 18 to 73 pM). This showed that this cytokine tolerates N-terminal fusions to antibodies or fragments thereof without a significant loss of avidity for human IL-10R1. In contrast, the antibody-IL-10 fusion constructs based on the monomeric cytokine did not show the avidity effect of the dimeric IL-10 fusions and thus their affinities to the receptor were in the three-digit pM or one-digit nM range (815 pM and 1.1 nM, respectively). Binding to FAP depends on the respective antibody, with clone 4B9 showing higher affinity/avidity to human and cynomolgus FAP, whereas clone 4G8 exhibits higher affinity/avidity to murine FAP. In fact, the avidity of the 4G8 antibody to murine FAP was so strong that it was impossible to determine the dissociation rate of the complex under the applied conditions.

The interaction between IL-10 and IL-10R1 is of high affinity (avidity) ranging from ~35-200 pM (Moore, K. W. et al., Annu. Rev. Immunol. 19, 683-765 (2001)). For the constructs comprising a dimeric IL-10 portion or two independent monomers, the fusion to the antibody does not seem to alter the affinity significantly (~19-73 pM). However, for the monomeric IL-10 fusion constructs, this strength of binding was dramatically reduced, most likely, because there is no avidity effect as occurs for the dimeric cytokine or two monomers fused to the same IgG. Ideally, the affinity of the antibody-IL-10 fusion constructs to the target FAP should be higher than that for the high affinity cytokine receptor IL-10R1 in order to achieve efficient targeting to tissues where FAP is expressed. Despite the high affinity between IL-10 and IL-10R1, the affinities to the target FAP exhibited by the molecules based on the IgG-IL-10 format are still higher: clone 4B9 IgG-IL-10 (48 pM to IL-10R1 vs. 11 pM to human FAP) and clone 4G8 (25 pM to IL-10R1 vs. 6 pM to murine FAP), respectively. These affinities to IL-10R1 as well as to FAP seem to be suitable for achieving efficient targeting to FAP-overexpressing tissues and IL-10R1 does not seem to represent a sink for these molecules.

Suppression of LPS-Induced Production of Pro-Inflammatory Cytokines by Primary Monocytes For functional characterization and differentiation between IgG or Fab based FAP-targeted IL-10 constructs the potency of these molecules was assessed in different in vitro assays. For example the efficacy to suppress LPS-induced production of pro-inflammatory cytokines by primary monocytes was measured. For this experiment, 200 ml of heparinized peripheral blood (obtained from healthy volunteers, Medical Services department, Roche Diagnostics GmbH, Penzberg, Germany) was separated by Ficoll Hypaque density gradient followed by negative isolation of monocytes (Miltenyi Biotec GmbH, Bergisch Gladbach, Germany, #130-091-153). Purified monocytes were seeded in 96-well F cell culture plates (Costar/Corning Life Sciences, Amsterdam, The Netherlands; #3596) at $5\times10^4$ cells/well in medium (RPMI 1640 [Gibco/Invitrogen, Darmstadt, Germany, cat. no. #10509-24] supplemented with 10% human serum, 2 mM L-glutamine [Gibco, #25030], and Pen/Strep).

All antibody-IL-10 fusion proteins were tested (a) in solution and (b) in an experimental setting, in which recombinant human FAP ($c_{fin}$=1 µg/ml) was coated overnight at 4° C. onto the plate (alternatively, 60-90 min at room temperature) and the antibody-IL-10 fusion proteins immobilized by binding to the coated FAP.

For set-up (a), cells were stimulated directly after seeding with 100 ng/ml LPS (Sigma-Aldrich/Nunc, Taufkirchen, Germany, # L3129) in the presence or absence of titrated amounts (normally, 0-500 nM) of the indicated antibody-fusion constructs or recombinant wild type human IL-10 as positive control. For set-up (b) unbound FAP was removed after coating, and plates were blocked with medium (see above) for 1 h at room temperature, before incubation with IL-10 constructs for an additional hour. Thereafter, plates were washed with medium, before monocytes were added into the culture together with an appropriate stimulus (100 ng/ml LPS).

For all experiments, cells were incubated for 24 h at 37° C. and 5% $CO_2$. Supernatants were collected (optionally stored at −20/−80° C.) and tested for cytokine production using CBA Flex Sets for IL-1β, IL-6, G-CSF, and/or TNFα (BD Biosciences, Heidelberg, Germany, #558279, #558276, #558326 and #558299). Plates were measured with a FACS Array and analyzed using FCAP software (both purchased from BD).

Figures 10A, 10B, 10C:
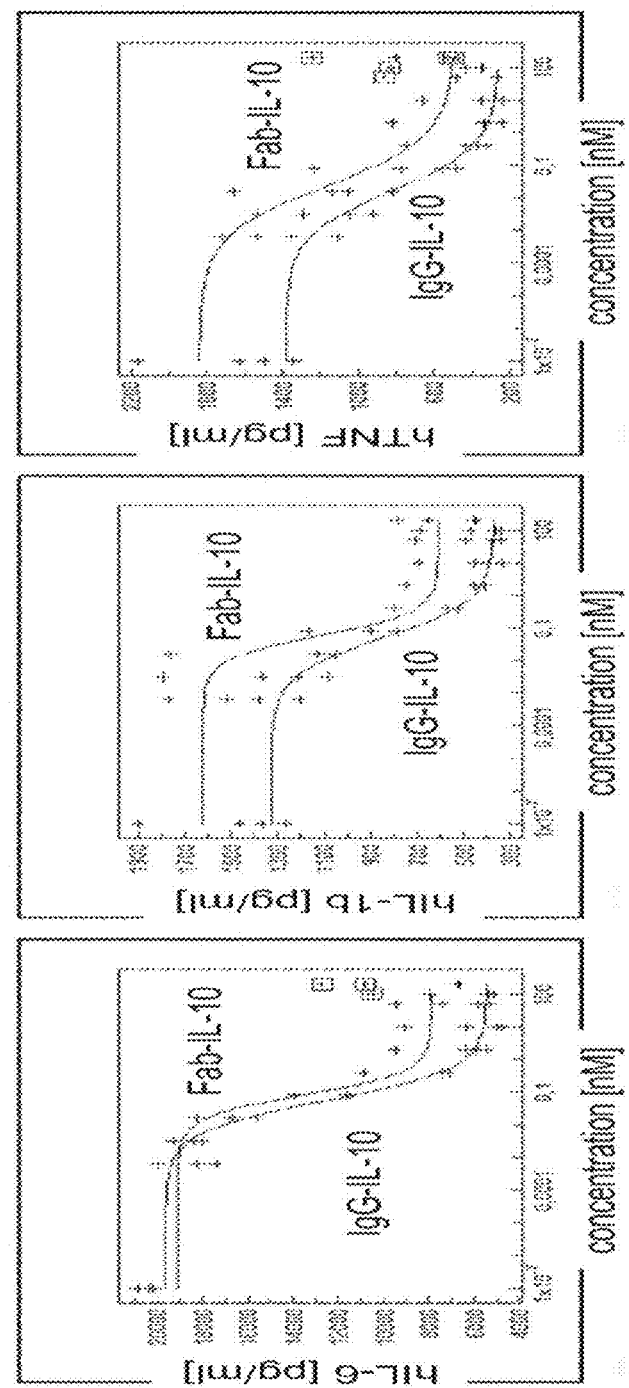
FIGS. 10A-10F Suppression of pro-inflammatory cytokine production by monocytes by different antibody-IL-10 fusion proteins.
Figures 10D, 10E, 10F:
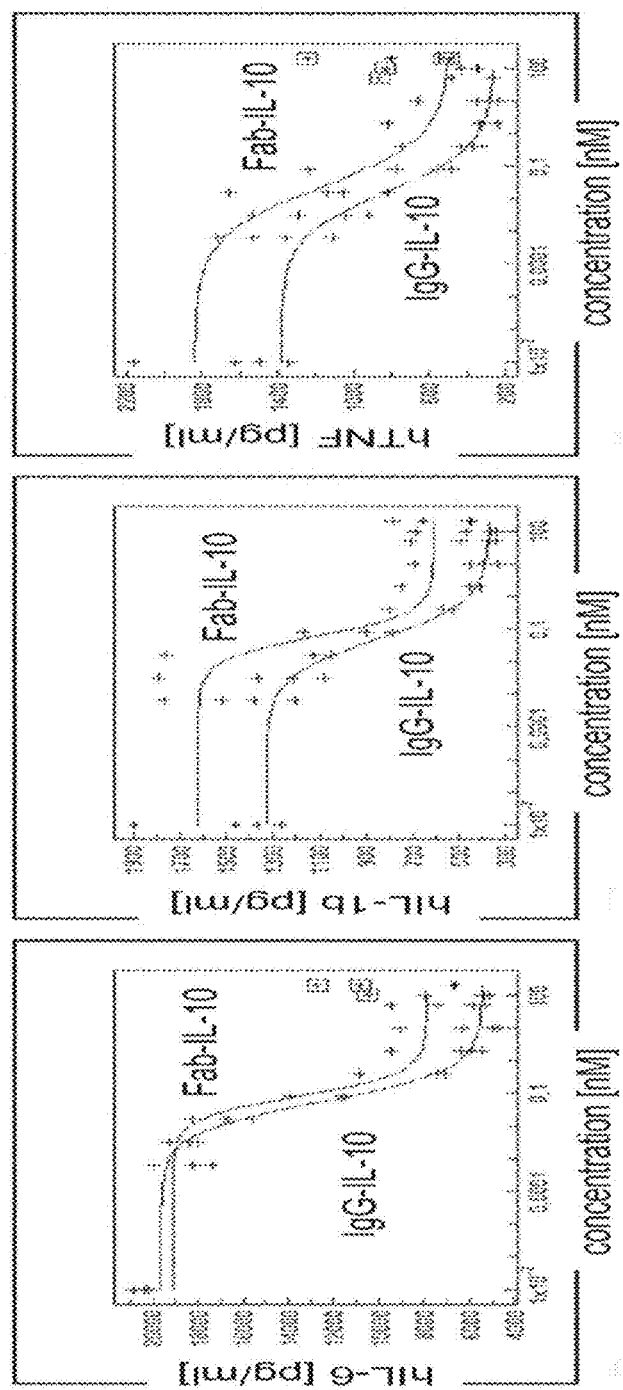
Figure 11G:
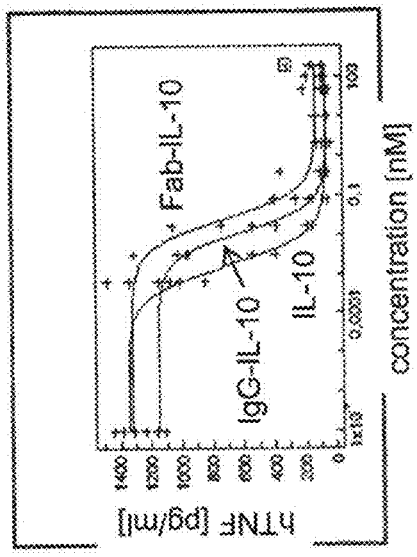
Figure 11J:
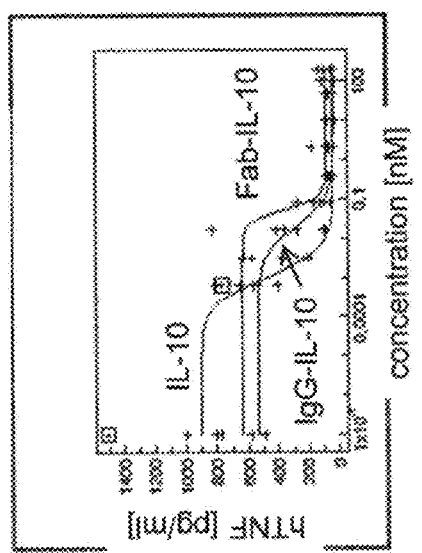
Figure 11H:
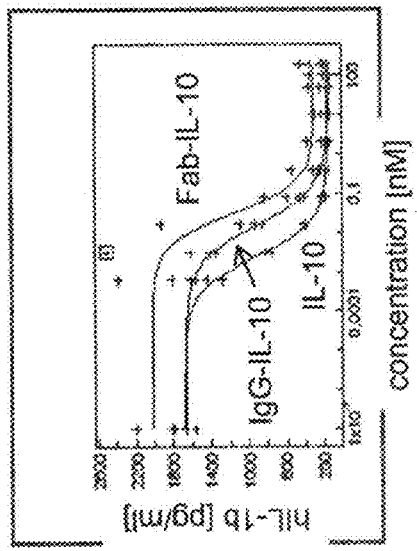
Figure 11K:
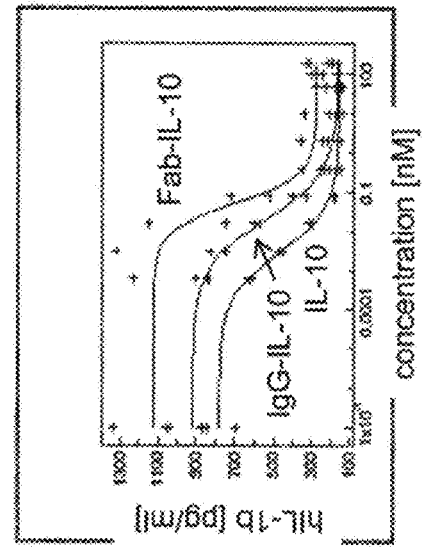
Figure 11I:
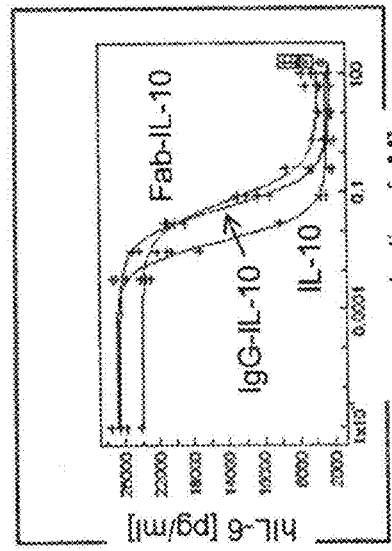
Figure 11L:
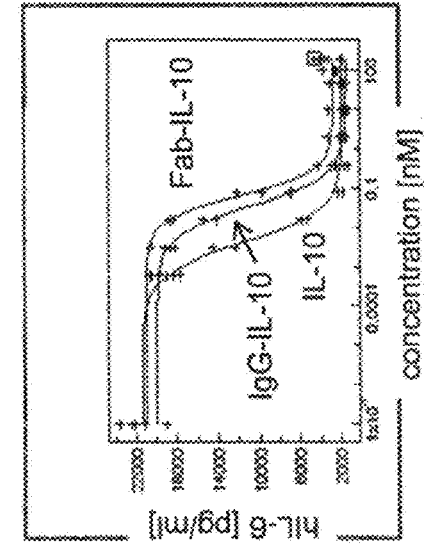
Figures 12A, 12B, 12C:
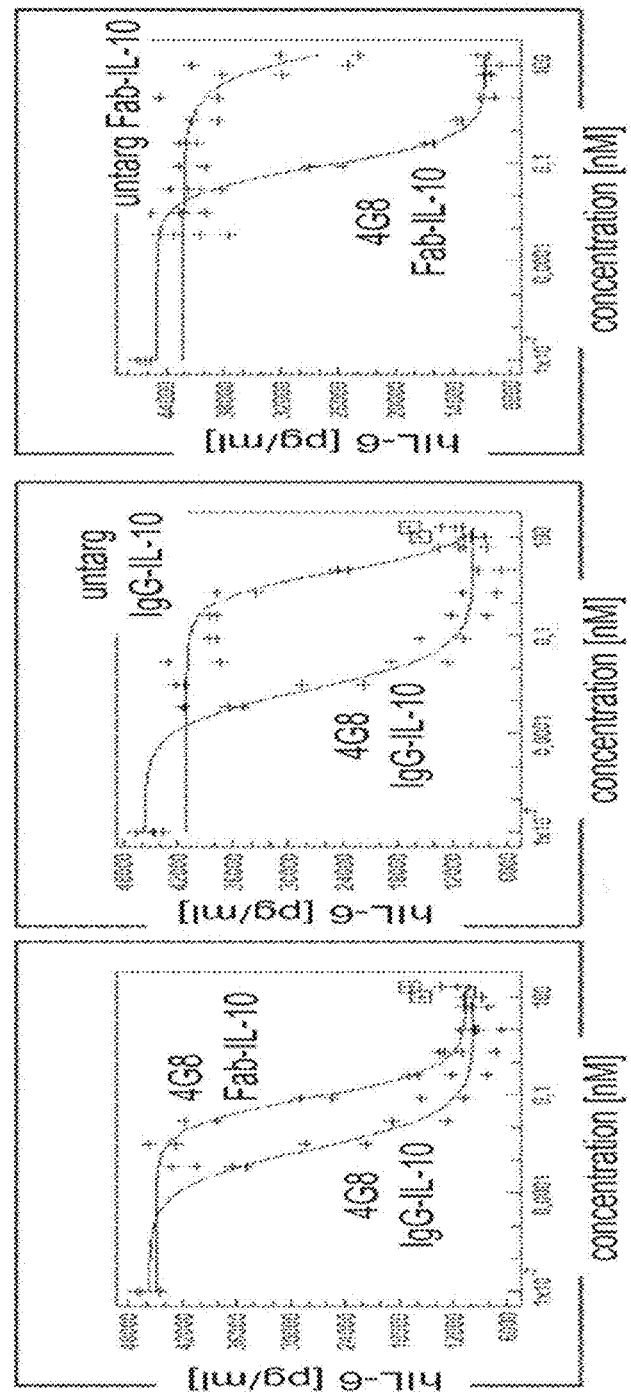
FIGS. 12A-12F Suppression of IL-6 production by monocytes by different antibody-IL-10 fusion proteins.
Figures 12D, 12E, 12F:
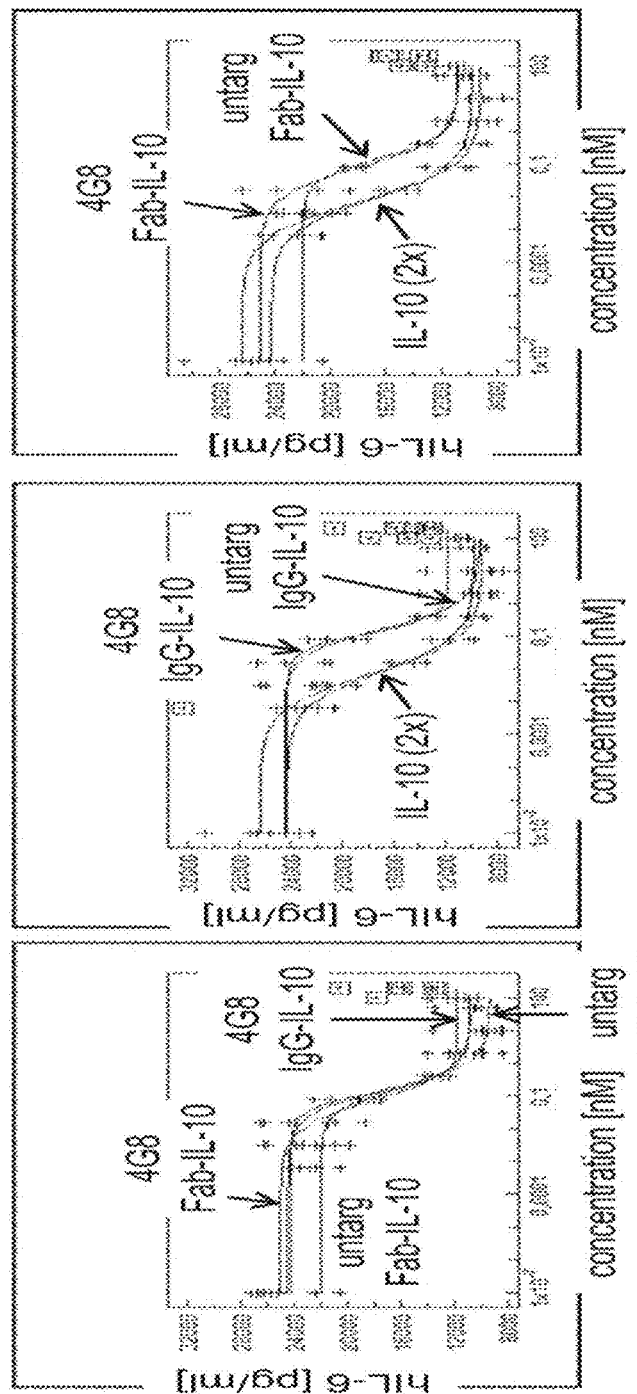

As shown in FIGS. 10A-10F, the in vitro potency of 4G8 Fab-IL-10 and IgG-IL-10 in the suppression of pro-inflammatory cytokines IL-1β, IL-6, and TNFα was comparable in set-up (a) (FIGS. 10D-10F). In contrast, in set-up (b) the IgG-based format demonstrated superior potency compared to Fab-IL-10 (FIGS. 10A-10C). The corresponding EC50 values [nM] are shown in Table 3. The EC50 values of the IgG-IL-10 construct in set-up (b) were similar to the ones of recombinant wt human IL-10 (which could only be tested in set-up (a)).

TABLE 3

EC50 values of 4G8-IgG-IL-10 and 4G8-Fab-IL-10 for suppression of cytokine production by monocytes (donor 1).

| sample | EC50 [nM] set-up (a) (solution) | | | EC50 [nM] set-up (b) (immobilized) | | |
|---|---|---|---|---|---|---|
| | hIL-6 | hIL-1β | hTNFα | hIL-6 | hIL-1β | hTNFα |
| hu wt IL-10 | 0.010 | 0.009 | 0.002 | not applicable/tested | | |
| IgG-IL-10 | 0.054 | 0.049 | 0.017 | 0.002 | 0.001 | 0.001 |
| Fab-IL-10 | 0.083 | 0.059 | 0.023 | 0.103 | 0.085 | 0.017 |

This result was reproduced in an independent experiment, using two different blood donors (FIGS. 11A-11F and 11G-11L, Table 4 and 5). In this experiment again the IgG-based targeted IL-10 construct was significantly superior to the Fab-based molecule in the suppression of all three cytokines tested, as indicated by the EC50 values obtained in set-up (b). In set-up (a), all molecules were comparable.

TABLE 4

EC50 values of 4G8-IgG-IL-10 and 4G8-Fab-IL-10 for suppression of cytokine production by monocytes (donor 2).

| sample | EC50 [nM] set-up (a) (solution) | | | EC50 [nM] set-up (b) (immobilized) | | |
|---|---|---|---|---|---|---|
| | hIL-6 | hIL-1β | hTNFα | hIL-6 | hIL-1β | hTNFα |
| hu wt IL-10 | 0.006 | 0.002 | 0.002 | not applicable/tested | | |
| IgG-IL-10 | 0.039 | 0.015 | 0.011 | 0.001 | 0.0002 | 0.0002 |
| Fab-IL-10 | 0.061 | 0.030 | 0.024 | 0.060 | 0.023 | 0.017 |

TABLE 5

EC50 values of 4G8-IgG-IL-10 and 4G8-Fab-IL-10 for suppression of cytokine production by monocytes (donor 3).

| Sample | EC50 [nM] set-up (a) (solution) | | | EC50 [nM] set-up (b) (immobilized) | | |
|---|---|---|---|---|---|---|
| | hIL-6 | hIL-1β | hTNFα | hIL-6 | hIL-1β | hTNFα |
| hu wt IL-10 | 0.004 | 0.003 | 0.001 | not applicable/tested | | |
| IgG-IL-10 | 0.036 | 0.020 | 0.019 | 0.001 | 0.0002 | 0.0002 |
| Fab-IL-10 | 0.065 | 0.052 | 0.052 | 0.057 | 0.036 | 0.025 |

In a further experiment, the potency of Fab and IgG based IL-10 constructs in the suppression of IL-6 production by monocytes was again assessed, and compared to wt IL-10 as well as untargeted Fab-IL-10 and IgG-IL-10 constructs, which do not bind to FAP (FIGS. 12A-12F and Table 6). Again, 4G8-IgG-IL-10 was found to be more efficient in the suppression of IL-6 production in the experimental set-up (b) compared to 4G8-Fab-IL-10, while untargeted constructs caused suppression only at the highest concentrations. In contrast, in set-up (a), potency of all constructs was comparable.

TABLE 6

EC50 values of 4G8-IgG-IL-10 and 4G8-Fab-IL-10 for suppression of IL-6 production by monocytes (donor 4).

| | EC50 [nM] IL-6 | |
|---|---|---|
| Sample | set-up (a) (solution) | set-up (b) (immobilized) |
| hu wt IL-10 | 0.007 | not tested |
| IgG-IL-10 | 0.123 | 0.002 |
| Fab-IL-10 | 0.078 | 0.081 |
| germline IgG-IL-10 | 0.166 | not calculable |
| germline Fab-IL-10 | 0.152 | not calculable |

As the concentration of recombinant human FAP used for coating in the previous assays might reflect an artificial or non-physiologic condition, the amount of coated FAP was titrated ($c_{fin}$ between 0.25 and 5 µg/ml) and its impact on EC50 values assessed in the experimental set-up (b).

Figure 13:
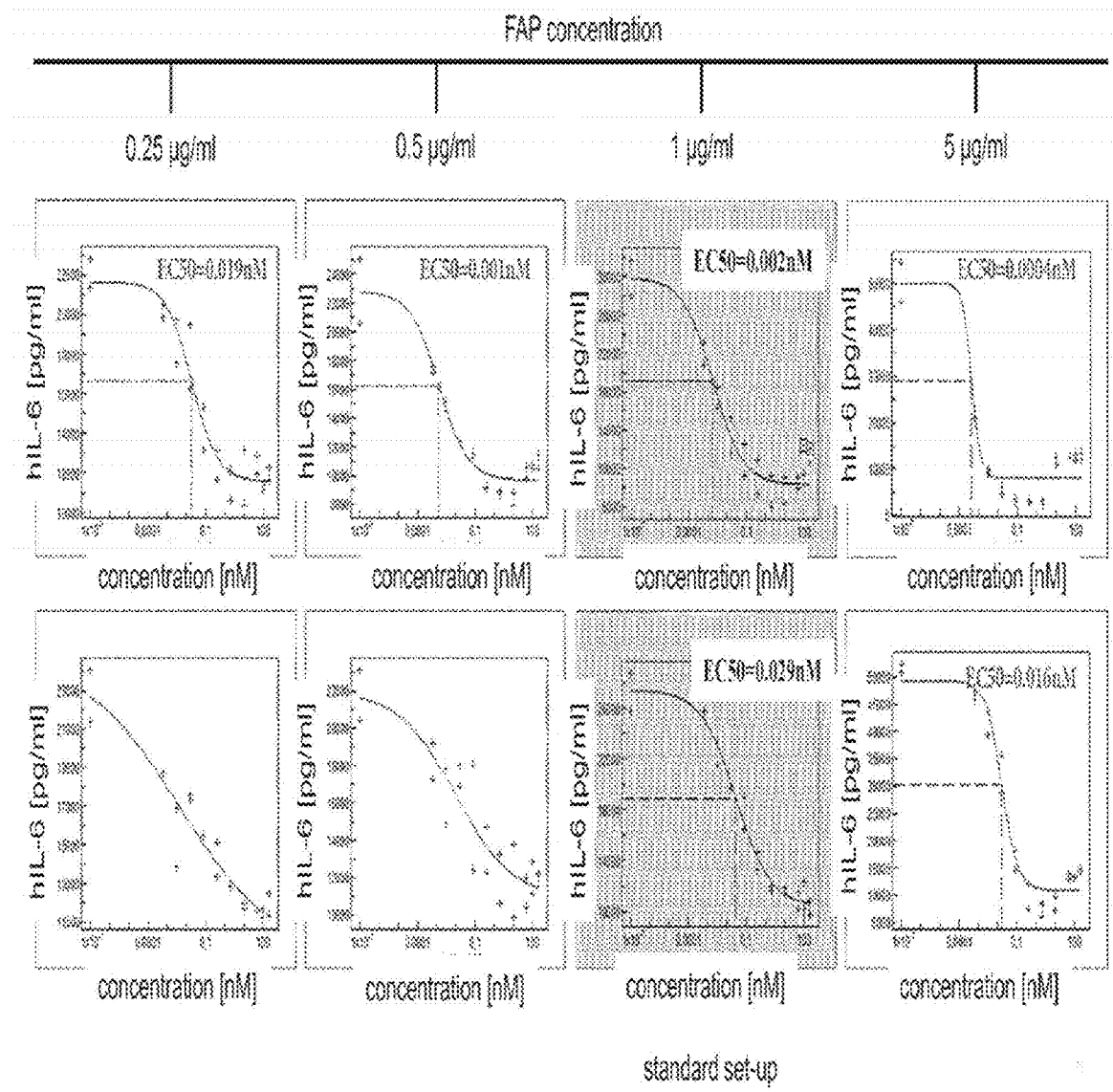
FIG. 13 Suppression of IL-6 production by monocytes by different antibody-IL-10 fusion proteins. 4G8 Fab-IL-10 (lower row) or 4G8 IgG-IL-10 (upper row) were immobilized on cell culture plates coated with different concentrations of recombinant human FAP before monocytes and 100 ng/ml LPS as stimulus were added for 24 h. Concentrations of IL-6 in supernatant were measured subsequently.
Figure 14B:
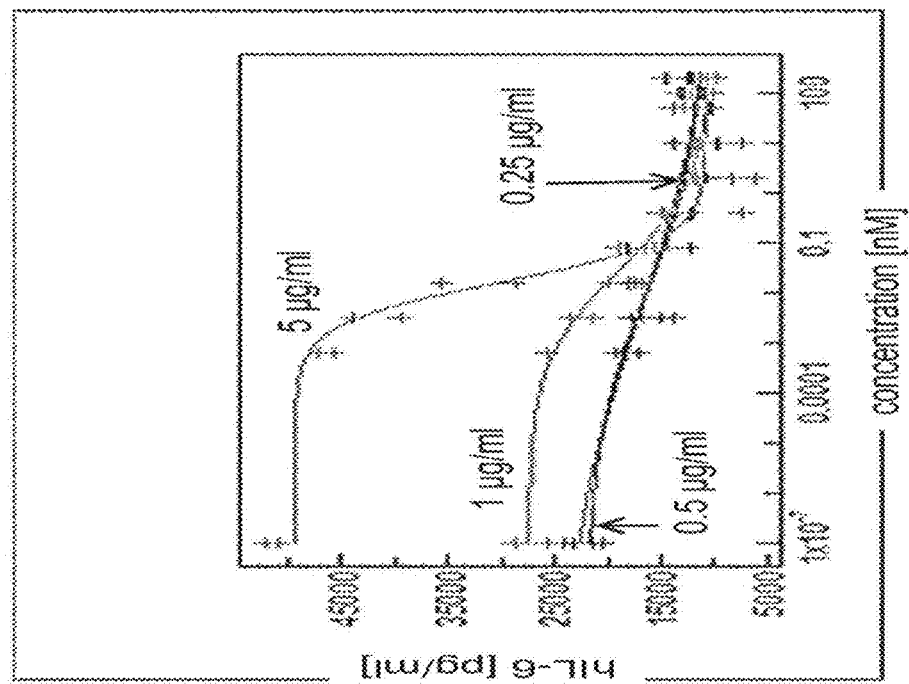
FIGS. 14A-14B Suppression of IL-6 production by monocytes by different antibody-IL-10 fusion proteins. 4G8 Fab-IL-10 (FIG. 14B) or 4G8 IgG-IL-10 (FIG. 14A) were immobilized on cell culture plates coated with different concentrations of recombinant human FAP before monocytes and 100 ng/ml LPS as stimulus were added for 24 h. Concentrations of IL-6 in supernatant were measured subsequently. The same data as in FIG. 13 is plotted, but in different comparison.
Figure 14A:
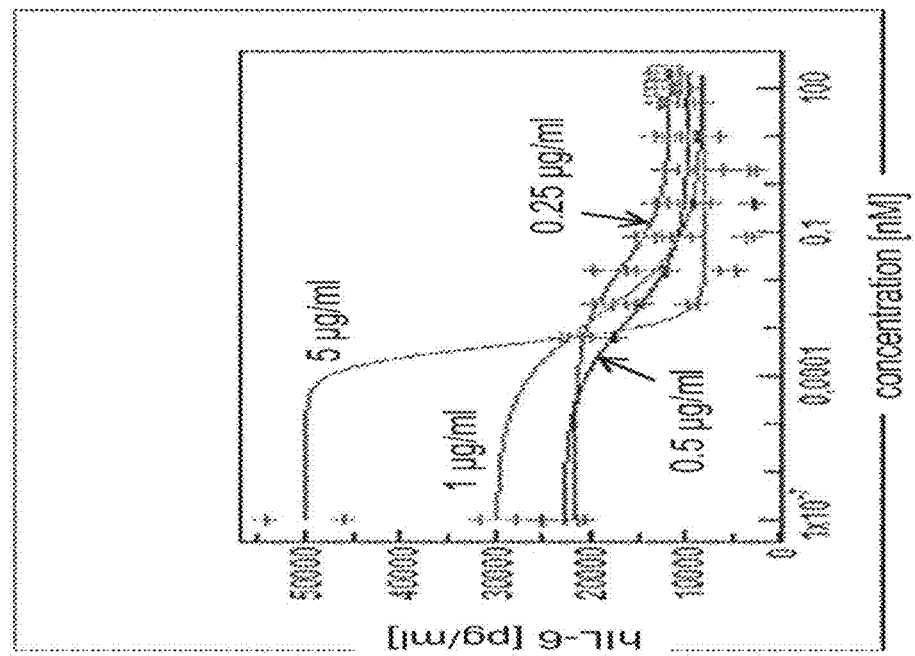

As shown in FIG. 13, overall there is no drastic difference in the ratios of EC50 values for IgG- and Fab-based constructs. At all concentrations, the IgG-IL-10 construct was more potent in the inhibition of IL-6 induction (FIG. 13 and Table 7 and 8). The concentration of coated FAP did, however, influence the outcome of the experiments as with decreasing concentrations the EC50 values generally increased, which might reflect the amount of constructs immobilized on the microtiter plate (Table 8; for the Fab-based construct a cytokine reduction was observed at the lowest FAP concentrations, but an EC50 could not be calculated). Interestingly, at high FAP concentrations (5 µg/ml) an increase in the total amount of secreted IL-6 was detected (FIGS. 14A-14B).

In a further experiment, IL-10 fusion constructs comprising a different FAP targeting domain, affinity-matured anti-FAP antibody variant 4B9, was tested. Again, the in vitro potency of the constructs in suppression of LPS-induced IL-6 production by monocytes was assessed in experimental set-up (a) and (b).

Figure 15B:
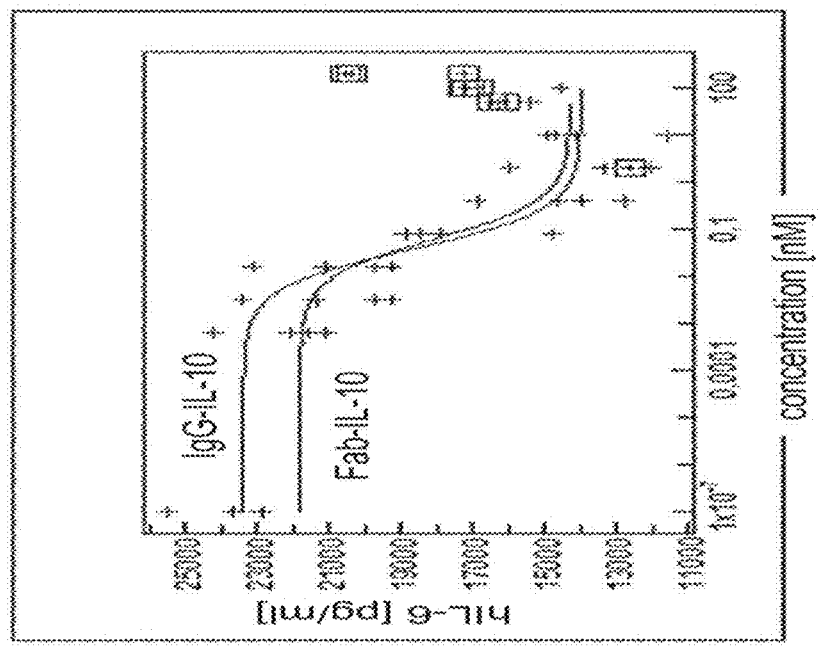
FIGS. 15A-15B Suppression of IL-6 production by monocytes by different antibody-IL-10 fusion proteins.
Figure 15A:
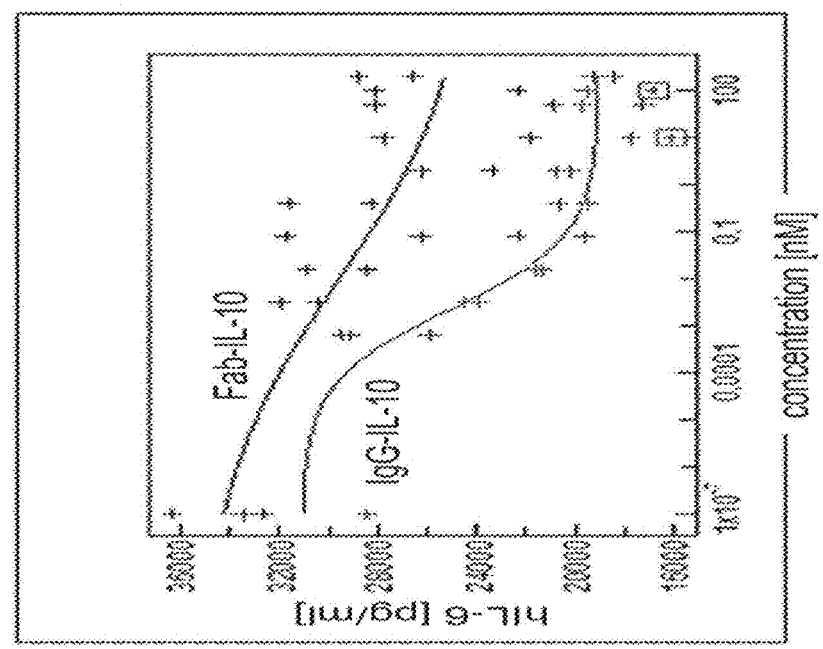

FIGS. 15A-15B shows that for 4B9-based constructs the IgG-IL-10 molecules were superior to the Fab-IL-10 constructs in suppression of IL-6 production in experimental set-up (a) (and comparable in set-up (b)). Corresponding EC50 values are shown in Table 9. In general, 4B9 and 4G8 constructs demonstrated similar potency.

TABLE 7

EC50 values of 4G8-IgG-IL-10 and human wild-type IL-10 (in solution) for suppression of IL-6 production by monocytes (donor 5).

| Sample | hIL-6 EC50 [nM] |
|---|---|
| 4G8-IgG-IL-10 | 0.066 |
| hu wt IL-10 | 0.010 |

TABLE 8

EC50 values of 4G8-IgG-IL-10 and 4G8-Fab-IL-10, immobilized on different concentrations of coated FAP, for suppression of IL-6 production by monocytes (donor 5).

| | hIL-6 EC50 [nM] | |
|---|---|---|
| FAP conc. | 4G8-IgG-IL-10 | 4G8-Fab-IL-10 |
| 0.25 µg/ml | 0.019 | — |
| 0.5 µg/ml | 0.001 | — |
| 1 µg/ml | 0.002 | 0.029 |
| 5 µg/ml | 0.0004 | 0.016 |

TABLE 9

EC50 values of 4G8 and 4B9-based IgG-IL-10 and Fab-IL-10 for suppression of IL-6 production by monocytes (donor 7).

| | EC50 [nM] IL-6 | |
|---|---|---|
| Sample | Set-up (a) | Set-up (b) |
| hu wt IL-10 | 0.008 | not tested |
| 4G8 IgG-IL-10 | not tested | 0.009 |
| 4G8 Fab-IL-10 | not tested | 0.065 |
| 4B9 IgG-IL-10 | 0.038 | 0.002 |
| 4B9 Fab-IL-10 | 0.063 | not calculable |

In a further series of experiments, 4G8-based IgG-IL-10, Fab-IL-10, Fab-IL-10M1-Fab and IgG-IL-10M1 constructs were compared. Suppression of LPS-induced production of pro-inflammatory cytokines IL-6, IL-1β and TNFα by monocytes was assessed in experimental set-up (a) and (b). The results of these experiments are shown in Tables 10-12 (three different donors). As in previous experiments, IgG-IL-10 was the most potent construct, particularly in experimental set-up (b).

TABLE 10

EC50 values of 4G8 IgG-IL-10, 4G8 Fab-IL-10, 4G8 Fab-IL-10M1-Fab and 4G8 IgG-IL-10M1 fusion proteins for suppression of cytokine production by monocytes (donor 1).

| | EC50 [nM] set-up (a) (solution) | | | EC50 [nM] set-up (b) (immobilized) | | |
|---|---|---|---|---|---|---|
| Sample | hIL-6 | hIL-1β | hTNFα | hIL-6 | hIL-1β | hTNF6α |
| hu wt IL-10 | 0.010 | 0.009 | 0.002 | not tested | not tested | not tested |
| IgG-IL-10 | 0.054 | 0.049 | 0.017 | 0.002 | 0.001 | 0.001 |
| Fab-IL-10 | 0.086 | 0.059 | 0.023 | 0.103 | 0.085 | 0.017 |
| Fab-IL-10M1-Fab | not calculable | not calculable | not calculable | not calculable | not calculable | not calculable |
| IgG-IL-10M1 | not calculable | not calculable | not calculable | not calculable | not calculable | not calculable |

TABLE 11

EC50 values of 4G8 IgG-IL-10, 4G8 Fab-IL-10, 4G8 Fab-IL-10M1-Fab and 4G8 IgG-IL-10M1 fusion proteins for suppression of cytokine production by monocytes (donor 2).

| | EC50 [nM] set-up (a) (solution) | | | EC50 [nM] set-up (b) (immobilized) | | |
|---|---|---|---|---|---|---|
| Sample | hIL-6 | hIL-1β | hTNFα | hIL-6 | hIL-1β | hTNFα |
| hu wt IL-10 | 0.006 | 0.002 | 0.002 | not tested | not tested | not tested |
| IgG-IL-10 | 0.039 | 0.015 | 0.011 | 0.001 | 0.0002 | 0.0002 |
| Fab-IL-10 | 0.061 | 0.030 | 0.024 | 0.060 | 0.023 | 0.017 |
| Fab-IL-10M1-Fab | not calculable | not calculable | not calculable | not calculable | 3.339 | 2.847 |
| IgG-IL-10M1 | not calculable | not calculable | not calculable | 0.723 | 0.140 | 0.059 |

TABLE 12

EC50 values of 4G8 IgG-IL-10, 4G8 Fab-IL-10, 4G8 Fab-IL-10M1-Fab and 4G8 IgG-IL-10M1 fusion proteins for suppression of cytokine production by monocytes (donor 3).

| Sample | EC50 [nM] set-up (a) (solution) | | | EC50 [nM] set-up (b) (immobilized) | | |
|---|---|---|---|---|---|---|
| | hIL-6 | hIL-1β | hTNFα | hIL-6 | hIL-1β | hTNFα |
| hu wt IL-10 | 0.004 | 0.003 | 0.001 | not tested | not tested | not tested |
| IgG-IL-10 | 0.036 | 0.020 | 0.019 | 0.001 | 0.0002 | 0.0002 |
| Fab-IL-10 | 0.065 | 0.052 | 0.052 | 0.057 | 0.036 | 0.025 |
| Fab-IL-10M1-Fab | not calculable | not calculable | not calculable | not calculable | 4.713 | not calculable |
| IgG-IL-10M1 | not calculable | 2.890 | not calculable | 0.254 | 0.117 | 0.145 |

In still a further series of experiments, 4G8-based Fab-IL-10, Fab-scIL-10-Fab and Fab-IL-10M1-Fab constructs were compared. Suppression of LPS-induced production of IL-6, IL-1β, TNFα and G-CSF by monocytes was assessed in experimental set-up (a) and (b). The results of these experiments are shown in Tables 13-17 (six different donors). The results show, that the construct comprising a dimeric IL-10 molecule is more potent than the constructs with a scIL-10 or a monomeric IL-10M1 molecule.

TABLE 13

EC50 values of 4G8 Fab-IL-10, 4G8 Fab-scIL-10-Fab and 4G8 Fab-IL-10M1-Fab fusion proteins for suppression of cytokine production by monocytes.

| Sample | EC50 [nM] set-up (a) (solution) | | | EC50 [nM] set-up (b) (immobilized) | | |
|---|---|---|---|---|---|---|
| | hIL-6 | hIL-1β | hTNFα | hIL-6 | hIL-1β | hTNFα |
| hu wt IL-10 | 0.004 | 0.004 | 0.001 | not tested | not tested | not tested |
| Fab-IL-10 | 0.030 | 0.020 | 0.007 | 0.020 | 0.003 | 0.001 |
| Fab-scIL-10-Fab | 0.110 | 0.090 | 0.060 | 0.200 | 0.100 | 0.030 |
| Fab-IL-10M1-Fab | not calculable | not calculable | not calculable | not calculable | not calculable | not calculable |

TABLE 14

EC50 values of 4G8 Fab-IL-10, 4G8 Fab-scIL-10-Fab and 4G8 Fab-IL-10M1-Fab fusion proteins for suppression of IL-6 production by monocytes.

| Sample | EC50 [nM] IL-6 supression (solution) | | | | | | | |
|---|---|---|---|---|---|---|---|---|
| | Donor #1 | Donor #2 | Donor #3 | Donor #4 | Donor #5 | Donor #6 | Mean | Std. dev. |
| hu wt IL-10 | 0.004 | 0.008 | 0.004 | 0.003 | 0.0003 | 0.004 | 0.004 | 0.002 |
| Fab-IL-10 | 0.030 | n.d. | 0.070 | 0.030 | 0.070 | 0.260 | 0.092 | 0.096 |
| Fab-scIL-10-Fab | 0.110 | n.d. | 0.150 | 0.110 | 0.250 | 0.630 | 0.250 | 0.220 |
| Fab-IL-10M1-Fab | not calc. | not calc. | not calc. | not calc. | not calc. | not calc. | — | — |

TABLE 15

EC50 values of 4G8 Fab-IL-10, 4G8 Fab-scIL-10-Fab and 4G8 Fab-IL-10M1-Fab fusion proteins for suppression of IL-1B production by monocytes.

| Sample | EC50 [nM] IL-1B supression (solution) | | | | | | | |
|---|---|---|---|---|---|---|---|---|
| | Donor #1 | Donor #2 | Donor #3 | Donor #4 | Donor #5 | Donor #6 | Mean | Std. dev. |
| hu wt IL-10 | 0.004 | 0.006 | 0.004 | 0.002 | n.d. | 0.006 | 0.004 | 0.002 |
| Fab-IL-10 | 0.020 | n.d. | 0.050 | 0.020 | 0.050 | 0.370 | 0.102 | 0.150 |
| Fab-scIL-10-Fab | 0.090 | n.d. | 0.110 | 0.090 | 0.270 | 1.460 | 0.404 | 0.595 |
| Fab-IL-10M1-Fab | not calc. | not calc. | not calc. | not calc. | not calc. | not calc. | | |

TABLE 16

EC50 values of 4G8 Fab-IL-10, 4G8 Fab-scIL-10-Fab and 4G8 Fab-IL-10M1-Fab fusion proteins for suppression of G-CSF production by monocytes.

| Sample | EC50 [nM] G-CSF supression (solution) | | | | | | | |
|---|---|---|---|---|---|---|---|---|
| | Donor #1 | Donor #2 | Donor #3 | Donor #4 | Donor #5 | Donor #6 | Mean | Std. dev. |
| hu wt IL-10 | 0.003 | 0.006 | 0.003 | 0.003 | 0.0001 | 0.003 | 0.003 | 0.002 |
| Fab-IL-10 | 0.010 | n.d. | 0.050 | 0.010 | 0.050 | 260 | 0.076 | 0.105 |
| Fab-scIL-10-Fab | 0.060 | n.d. | 0.110 | 0.060 | 0.200 | 1.160 | 0.318 | 0.474 |

TABLE 16-continued

EC50 values of 4G8 Fab-IL-10, 4G8 Fab-scIL-10-Fab and 4G8 Fab-IL-10M1-Fab fusion proteins for suppression of G-CSF production by monocytes.

| | EC50 [nM] G-CSF supression (solution) | | | | | | | |
|---|---|---|---|---|---|---|---|---|
| Sample | Donor #1 | Donor #2 | Donor #3 | Donor #4 | Donor #5 | Donor #6 | Mean | Std. dev. |
| Fab-IL-10M1-Fab | not calc. | not calc. | not calc. | not calc. | not calc. | not calc. | — | — |

TABLE 17

EC50 values of 4G8 Fab-IL-10, 4G8 Fab-scIL-10-Fab and 4G8 Fab-IL-10M1-Fab fusion proteins for suppression of TNFa production by monocytes.

| | EC50 [nM] TNFα supression (solution) | | | | | | | |
|---|---|---|---|---|---|---|---|---|
| Sample | Donor #1 | Donor #2 | Donor #3 | Donor #4 | Donor #5 | Donor #6 | Mean | Std. dev. |
| hu wt IL-10 | 0.001 | 0.002 | 0.001 | 0.003 | n.d. | 0.001 | 0.002 | 0.001 |
| Fab-IL-10 | 0.007 | n.d. | 0.040 | 0.007 | 0.040 | 0.018 | 0.055 | 0.072 |
| Fab-scIL-10-Fab | 0.060 | n.d. | 0.190 | 0.060 | 0.080 | 1.660 | 0.410 | 0.701 |
| Fab-IL-10M1-Fab | not calc. | not calc. | not calc. | not calc. | not calc. | not calc. | — | — |

Finally, 4B9 and 4G8-based Fab-IL-10 and IgG-(IL-10M1)₂ constructs were compared. Suppression of LPS-induced production of IL-6 by monocytes was assessed in experimental set-up (a) and (b). The results of this experiment are shown in Table 19. The results show that all constructs, including IgG-(IL-10M1)₂, perform better in set-up (b) than in set-up (a).

TABLE 18

EC50 values of 4B9 IgG-IL-10, 4G8 IgG-IL-10 and 4G8 IgG-(IL-10M1)₂ fusion proteins for suppression of IL-6 production by monocytes.

| Sample | EC50 [nM] set-up (a) (solution) hIL-6 | EC50 [nM] set-up (b) (immobilized) hIL-6 |
|---|---|---|
| hu wt IL-10 | 0.006 | not tested |
| 4B9 IgG-IL-10 | 0.035 | 0.011 |
| 4G8 IgG-IL-10 | 0.028 | 0.004 |
| IgG-(IL-10M1)₂ | not calculable | 0.039 |

Suppression of IFNγ-Induced Upregulation of MHC-II Molecules on Primary Monocytes For functional characterization and differentiation between IgG and Fab based FAP-targeted IL-10 constructs their ability to suppress IFNγ-induced MHC-II expression in monocytes was assessed. Similar to the cytokine suppression assay, this experiment was performed with the constructs either in solution (experimental set-up (a); see above) or immobilized by binding to FAP coated on the cell culture plate (experimental set-up (b); see above). In principle, monocytes were isolated and cultured as described above, but stimulated with 250 U/ml IFNγ (BD, #554616) for 24 h. Before stimulation, cells were optionally treated with recombinant wild-type (wt) IL-10 or the different antibody-IL-10 fusion constructs. After incubation, cells were detached by Accutase treatment (PAA, #L11-007) and stained with an anti-HLA-DR antibody (BD, #559866) in PBS containing 3% human serum (Sigma, #4522) to avoid any unspecific FcγR binding before subjecting to final FACS analysis.

The result of this experiment is shown in Table 19, demonstrating that for 4B9-based constructs the IgG-IL-10 molecules were superior to the Fab-IL-10 constructs in down-regulation of IFN□-induced MHC-II expression on primary monocytes in experimental set-up (b) (and comparable in set-up (a)).

TABLE 19

EC50 values of 4B9 IgG-IL-10 and 4B9 Fab-IL-10 for down-regulation of IFN□-induced MHC-II expression on primary monocytes.

| sample | EC50 [nM] set-up (a) (solution) | EC50 [nM] set-up (b) (immobilized) |
|---|---|---|
| Fab-IL-10 | 0.072 | not calculable |
| IgG-IL-10 | 0.064 | 0.018 |
| hu wt IL-10 | 0.004 | not tested |

IL-10 Induced STAT3 Phosphorylation in Isolated Primary Monocytes

As IL-10R signaling leads to phosphorylation of STAT3 several targeted IL-10 constructs and formats were functionally evaluated in a pSTAT3 assay using freshly isolated blood monocytes (Finbloom & Winestock, J. Immunol. 1995; Moore et al., Annu. Rev. Immunol. 2001; Mosser & Zhang, Immunological Reviews 2008). Briefly, CD14⁺ monocytes were untouched separated from Ficoll-isolated PBMC of healthy donors as described above. Typically, $3-10 \times 10^5$ cells were transferred into FACS tubes in 300 µl medium (RPMI1640/10% FCS/L-glutamine/pen/strep) and usually incubated for 30 min at 37° C., 5% CO₂, with 0-200/500 nM of wt human IL-10 or the indicated antibody-IL-10 fusion proteins. Then, 300 IA pre-warmed Fix buffer I (BD Biosciences, #557870) per tube was added, vortexed and incubated for 10 min at 37° C. before cells were washed once with 2 ml PBS/2% FCS and centrifuged at 250×g for 10 min. Subsequently, 300 µl ice-cooled Perm Buffer III (BD Biosciences, #558050) per tube was added for cell permeabilization and incubated for 30 min on ice before cells were again washed as described above. Finally, cells were resuspended in 100 µl antibody dilution (anti-Stat-3.A647; BD Biosciences, #557815) and incubated for 30 min at 4° C. before cells were washed and processed for FACS analysis.

The EC50 values obtained for the different constructs in this experiment are shown in Tables 20 and 21. The results show that constructs comprising a dimeric IL-10 molecule (Fab- or IgG-based) are more active than constructs comprising a scIL-10 molecule or a monomeric IL-10M1 molecule.

TABLE 20

EC50 values of 4G8-based antibody-IL-10 fusion proteins for IL-10 induced STAT3 phosphorylation in isolated primary monocytes.

| | EC50 [nM] pSTAT3 induction | | |
|---|---|---|---|
| Sample | Donor 1 | Donor 2 | Donor 3 |
| hu wt IL-10 | 0.029 | 0.019 | 0.021 |
| Fab-IL-10 | 0.154 | 0.194 | 0.087 |

TABLE 20-continued

EC50 values of 4G8-based antibody-IL-10 fusion proteins for IL-10 induced STAT3 phosphorylation in isolated primary monocytes.

| | EC50 [nM] pSTAT3 induction | | |
|---|---|---|---|
| Sample | Donor 1 | Donor 2 | Donor 3 |
| Fab-scIL-10-Fab | 0.557 | 0.430 | 0.116 |
| Fab-IL-10M1-Fab | 8.201 | 9.012 | 6.809 |

TABLE 21

EC50 values of 4B9-based antibody-IL-10 fusion proteins for IL-10 induced STAT3 phosphorylation in isolated primary monocytes.

| Sample | EC50 [nM] pSTAT3 induction |
|---|---|
| hu wt IL-10 | 0.017 |
| IgG-IL-10 | 0.130 |
| IgG-(IL-10M1)2 | 0.435 |

Biodistribution of FAP-Targeted and Untargeted Antibody-IL-10 Fusion Proteins

The tissue biodistribution of FAP-targeted In-111-labeled 4B9 IgG-IL-10, 4G8 IgG-IL-10 and untargeted DP47GS IgG-IL 10 was determined at 50 μg per mouse in DBA/1J mice with collagen-induced arthritis reaching a pre-determined arthritis score >3 (28 days after the first immunization). Biodistribution was performed at 72 h after i.v. injection of radiolabeled conjugates in five mice per group.

Results of this experiment are shown in Table 22. Uptake of the untargeted antibody-IL-10 fusion protein DP47GS IgG-IL-10 in the inflamed joints was significantly lower ($p<0.0001$) than uptake of the targeted IgG-IL-10 fusion proteins, indicating that the uptake of 4B9 IgG-IL-10 and 4G8 IgG-IL-10 is FAP-mediated. Splenic uptake most likely is IL-10-mediated, because all three constucts showed similar levels of splenic accumulation.

TABLE 22

Uptake of antibody constructs (% injected dose/gram of tissue).

| Tissue | 4B9 IgG-IL-10 | 4G8 IgG-IL-10 | DP47GS IgG-IL-10 |
|---|---|---|---|
| inflamed joints | 20.7 ± 1.1 | 19.6 ± 1.0 | 8.6 ± 1.0 |
| spleen | 6.3 ± 0.4 | 7.3 ± 0.3 | 6.7 ± 0.5 |
| blood | 4.2 ± 0.5 | 1.1 ± 0.1 | 7.3 ± 1.0 |

To study the effect of the IL-10 on the biodistribution of IgG-IL-10, in a second experiment the biodistribution of In-111-labeled 4G8 IgG-IL-10 was compared to that of In-111-labeled 4G8 IgG.

Results of this experiment are shown in Table 23. There was no significant difference in accumulation in the inflamed joints between 4G8 IgG and 4G8 IgG-IL-10, indicating that IL-10 did not significantly affect the targeting of 4G8 IgG to the inflamed sites. Splenic uptake of 4G8 IgGI-IL-10 is significantly higher than that of 4G8 IgG ($p<0.0001$), indicating that uptake in the spleen is partly IL-10 mediated.

TABLE 23

Uptake of antibody constructs (% injected dose/gram of tissue).

| Tissue | 4G8 IgG | 4G8 IgG-IL-10 |
|---|---|---|
| inflamed joints | 18.1 ± 1.0 | 19.6 ± 1.0 |
| spleen | 2.9 ± 0.2 | 7.3 ± 0.3 |
| blood | 3.9 ± 0.8 | 1.1 ± 0.1 |

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

---

The invention claimed is:

1. A fusion protein comprising an antibody and an IL-10 molecule, wherein the antibody comprises the heavy chain variable region of SEQ ID NO: 63 and the light chain variable region of SEQ ID NO: 65, and the IL-10 molecule comprises SEQ ID NO: 1.

2. The fusion protein of claim 1, wherein the fusion protein comprises two identical heavy chain polypeptides and two identical light chain polypeptides.

3. The fusion protein of claim 2, wherein each of the heavy chain polypeptides comprises an IgG-class antibody heavy chain and a monomeric IL-10 molecule.

4. The fusion protein of claim 3, wherein the monomeric IL-10 molecule is fused at its N-terminus to the C-terminus of the IgG-class antibody heavy chain.

5. The fusion protein of claim 4 additionally comprising a peptide linker to fuse the N-terminus of the monomeric IL-10 molecule to the C-terminus of the IgG-class antibody heavy chain.

6. The fusion protein of claim 3, wherein each of the heavy chain polypeptides further comprises a peptide linker.

7. The fusion protein of claim 3, wherein the monomeric IL-10 molecules comprised in the heavy chain polypeptides form a functional homodimeric IL-10 molecule.

8. The fusion protein of claim 1, wherein the antibody is an IgG-class antibody and comprises a modification, which modification reduces binding affinity of the antibody to an Fc receptor, as compared to a corresponding IgG-class antibody without the modification, wherein the IgG-class antibody comprises an amino acid substitution at a position according to EU numbering selected from the group consisting of 228, 233, 234, 235, 297, 329 and 331 of an antibody heavy chain.

9. The fusion protein of claim 8, wherein the Fc receptor is an Fcγ receptor.

10. The fusion protein of claim 8, wherein the Fc receptor is an activating Fc receptor.

11. The fusion protein of claim 8, wherein the Fc receptor is selected from the group of FcγRIIIa (CD16a), FcγRI (CD64), FcγRIIa (CD32) and FcαRI (CD89).

12. The fusion protein of claim 8, wherein the Fc receptor is FcγIIIa.

13. The fusion protein of claim 8, wherein the IgG-class antibody comprises a heavy chain comprising an amino acid substitution at position 329 according to EU numbering.

14. The fusion protein of claim 13, wherein the amino acid substitution is P329G.

15. The fusion protein claim 8, wherein the IgG-class antibody comprises a heavy chain comprising amino acid substitutions at positions 234 and 235 according to EU numbering.

16. The fusion protein of claim 15, wherein the amino acid substitutions are L234A and L235A (LALA).

17. The fusion protein of claim 8, wherein the IgG-class antibody comprises a heavy chain comprising amino acid substitutions L234A, L235A and P329G according to EU numbering.

18. The fusion protein of claim 1, wherein the antibody is an IgG-class antibody.

19. The fusion protein of claim 1, wherein the antibody is $IgG_1$-subclass antibody.

20. The fusion protein of claim 1, wherein the antibody is a full-length antibody.

21. The fusion protein of claim 1, wherein the antibody is a human antibody.

22. A pharmaceutical composition comprising the fusion protein of claim 1 and a pharmaceutically acceptable carrier.

* * * * *

SEQUENCE LISTING

<160> NUMBER OF SEQ ID NOS: 89

<210> SEQ ID NO 1
<211> LENGTH: 160
<212> TYPE: PRT
<213> ORGANISM: Homo sapiens

<400> SEQUENCE: 1

```
Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
                20                  25                  30

Val Lys Thr Phe Phe Gln Met Lys Asp Gln Leu Asp Asn Leu Leu Leu
            35                  40                  45

Lys Glu Ser Leu Leu Glu Asp Phe Lys Gly Tyr Leu Gly Cys Gln Ala
        50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
                100                 105                 110
```

Pro Cys Glu Asn Lys Ser Lys Ala Val Glu Gln Val Lys Asn Ala Phe
            115                 120                 125

Asn Lys Leu Gln Glu Lys Gly Ile Tyr Lys Ala Met Ser Glu Phe Asp
        130                 135                 140

Ile Phe Ile Asn Tyr Ile Glu Ala Tyr Met Thr Met Lys Ile Arg Asn
145                 150                 155                 160

<210> SEQ ID NO 2
<211> LENGTH: 480
<212> TYPE: DNA
<213> ORGANISM: Homo sapiens

<400> SEQUENCE: 2
agcccgggcc agggcaccca gagcgagaac agctgcaccc acttccccgg caacctgccc    60
aacatgctgc gggacctgag ggacgccttc agcagagtga aaaccttctt ccagatgaag   120
gaccagctgg acaacctgct gctgaaagag agcctgctgg aagatttcaa gggctacctg   180
ggctgtcagg ccctgagcga gatgatccag ttctacctgg aagaagtgat gccccaggcc   240
gagaaccagg accccgacat caaggcccac gtgaacagcc tgggcgagaa cctgaaaacc   300
ctgcggctga ctgcggcg tgccacaga tttctgccct gcgagaacaa gagcaaggcc   360
gtggaacagg tgaagaacgc cttcaacaag ctgcaggaaa agggcatcta caaggccatg   420
tccgagttcg acatcttcat caactacatc gaggcctaca tgacaatgaa aatccgcaat   480

<210> SEQ ID NO 3
<211> LENGTH: 340
<212> TYPE: PRT
<213> ORGANISM: Artificial Sequence
<220> FEATURE:
<223> OTHER INFORMATION: scIL-10

<400> SEQUENCE: 3

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

Gly Gly Gly Gly Ser Gly Gly Gly Ser Gly Gly Gly Ser Gly
                165                 170                 175

Gly Gly Gly Ser Ser Pro Gly Gln Gly Thr Gln Ser Glu Asn Ser Cys
            180                 185                 190

Thr His Phe Pro Gly Asn Leu Pro Asn Met Leu Arg Asp Leu Arg Asp
        195                 200                 205

Ala Phe Ser Arg Val Lys Thr Phe Phe Gln Met Lys Asp Gln Leu Asp
    210                 215                 220

Asn Leu Leu Leu Lys Glu Ser Leu Leu Glu Asp Phe Lys Gly Tyr Leu
225                 230                 235                 240

Gly Cys Gln Ala Leu Ser Glu Met Ile Gln Phe Tyr Leu Glu Glu Val
                245                 250                 255

Met Pro Gln Ala Glu Asn Gln Asp Pro Asp Ile Lys Ala His Val Asn
            260                 265                 270

Ser Leu Gly Glu Asn Leu Lys Thr Leu Arg Leu Arg Leu Arg Arg Cys
        275                 280                 285

His Arg Phe Leu Pro Cys Glu Asn Lys Ser Lys Ala Val Glu Gln Val
    290                 295                 300

Lys Asn Ala Phe Asn Lys Leu Gln Glu Lys Gly Ile Tyr Lys Ala Met
305                 310                 315                 320

Ser Glu Phe Asp Ile Phe Ile Asn Tyr Ile Glu Ala Tyr Met Thr Met
                325                 330                 335

Lys Ile Arg Asn
        340

<210> SEQ ID NO 4
<211> LENGTH: 1020
<212> TYPE: DNA
<213> ORGANISM: Artificial Sequence
<220> FEATURE:
<223> OTHER INFORMATION: scIL-10

<400> SEQUENCE: 4
agcccgggcc agggcaccca gagcgagaac agctgcaccc acttccccgg caacctgccc       60
aacatgctgc gggacctgag ggacgccttc agcagagtga aaaccttctt ccagatgaag      120
gaccagctgg acaacctgct gctgaaagag agcctgctgg aagatttcaa gggctacctg      180
ggctgtcagg ccctgagcga gatgatccag ttctacctgg aagaagtgat gccccaggcc      240
gagaaccagg accccgacat caaggcccac gtgaacagcc tgggcgagaa cctgaaaacc      300
ctgcggctga actgcggcg gtgccacaga tttctgccct gcgagaacaa gagcaaggcc      360
gtggaacagg tgaagaacgc cttcaacaag ctgcaggaaa agggcatcta caaggccatg      420
tccgagttcg acatcttcat caactacatc gaagcttaca tgaccatgaa gatcagaaac      480
ggcggaggcg gatctggcgg cggtggaagt ggaggcggag gatctggggg aggcggaagt      540
agcccgggcc agggcaccca gagcgagaac agctgcaccc acttccccgg caacctgccc      600
aacatgctgc gggacctgag ggacgccttc agcagagtga aaaccttctt ccagatgaag      660
gaccagctgg acaacctgct gctgaaagag agcctgctgg aagatttcaa gggctacctg      720
ggctgtcagg ccctgagcga gatgatccag ttctacctgg aagaagtgat gccccaggcc      780
gagaaccagg accccgacat caaggcccac gtgaacagcc tgggcgagaa cctgaaaacc      840
ctgcggctga actgcggcg gtgccacaga tttctgccct gcgagaacaa gagcaaggcc      900
gtggaacagg tgaagaacgc cttcaacaag ctgcaggaaa agggcatcta caaggccatg      960
tccgagttcg acatcttcat caactacatc gaggcctaca tgacaatgaa aatccgcaat     1020

<210> SEQ ID NO 5
<211> LENGTH: 166
<212> TYPE: PRT

<213> ORGANISM: Artificial Sequence
<220> FEATURE:
<223> OTHER INFORMATION: IL-10 monomer (IL-10M1)

<400> SEQUENCE: 5

```
Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Gly Gly Gly Ser Gly Gly Lys Ser Lys Ala Val Glu
        115                 120                 125

Gln Val Lys Asn Ala Phe Asn Lys Leu Gln Glu Lys Gly Ile Tyr Lys
130                 135                 140

Ala Met Ser Glu Phe Asp Ile Phe Ile Asn Tyr Ile Glu Ala Tyr Met
145                 150                 155                 160

Thr Met Lys Ile Arg Asn
                165
```

<210> SEQ ID NO 6
<211> LENGTH: 498
<212> TYPE: DNA
<213> ORGANISM: Artificial Sequence
<220> FEATURE:
<223> OTHER INFORMATION: IL-10 monomer (IL-10M1)

<400> SEQUENCE: 6

```
tctccaggcc agggcaccca gagcgagaac agctgcaccc acttccccgg caacctgccc        60
aacatgctgc gggacctgag ggacgccttc agcagagtga aaaccttctt ccagatgaag       120
gaccagctgg acaacctgct gctgaaagag agcctgctgg aagatttcaa gggctacctg       180
ggctgtcagg ccctgagcga gatgatccag ttctacctgg aagaagtgat gccccaggcc       240
gagaaccaga cccccgacat caaggcccac gtgaacagcc tgggcgagaa cctgaaaacc       300
ctgcggctga actgcggcg tgccacaga tttctgccct gcgagaacgg cggaggctct        360
ggcggaaagt ccaaggccgt gaacaggtg aagaacgcct tcaacaagct gcaggaaaag       420
ggcatctaca aggccatgag cgagttcgac atcttcatca actacatcga agcttacatg       480
acaatgaaga tacgaaac                                                    498
```

<210> SEQ ID NO 7
<211> LENGTH: 215
<212> TYPE: PRT
<213> ORGANISM: Artificial Sequence
<220> FEATURE:
<223> OTHER INFORMATION: 4G8 IgG - IL-10 (LC)

<400> SEQUENCE: 7

```
Glu Ile Val Leu Thr Gln Ser Pro Gly Thr Leu Ser Leu Ser Pro Gly
1               5                   10                  15
```

Glu Arg Ala Thr Leu Ser Cys Arg Ala Ser Gln Ser Val Ser Arg Ser
            20                  25                  30

Tyr Leu Ala Trp Tyr Gln Gln Lys Pro Gly Gln Ala Pro Arg Leu Leu
        35                  40                  45

Ile Ile Gly Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Val Ile Pro
                85                  90                  95

Pro Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 8
<211> LENGTH: 645
<212> TYPE: DNA
<213> ORGANISM: Artificial Sequence
<220> FEATURE:
<223> OTHER INFORMATION: 4G8 IgG - IL-10 (LC)

<400> SEQUENCE: 8
gagatcgtgc tgacccagtc ccccggcacc ctgtctctga gccctggcga gagagccacc    60
ctgtcctgca gagcctccca gtccgtgtcc cggtcctacc tcgcctggta tcagcagaag   120
cccggccagg cccctcggct gctgatcatc ggcgcctcta ccagagccac cggcatccct   180
gaccggttct ccggctctgg ctccggcacc gacttcaccc tgaccatctc ccggctggaa   240
cccgaggact tcgccgtgta ctactgccag cagggccagg tcatccctcc cacctttggc   300
cagggcacca agtggaaat caagcgtacg gtggccgctc cctccgtgtt catcttccca   360
ccctccgacg agcagctgaa gtccggcacc gcctccgtcg tgtgcctgct gaacaacttc   420
taccccgcg aggccaaggt gcagtggaag gtggacaacg ccctgcagtc cggcaactcc   480
caggaatccg tcaccgagca ggactccaag gacagcacct actccctgtc ctccaccctg   540
accctgtcca aggccgacta cgagaagcac aaggtgtacg cctgcgaagt gacccaccag   600
ggcctgtcca gccccgtgac caagtccttc aaccggggcg agtgc               645

<210> SEQ ID NO 9
<211> LENGTH: 626
<212> TYPE: PRT
<213> ORGANISM: Artificial Sequence
<220> FEATURE:
<223> OTHER INFORMATION: 4G8 IgG - IL-10 (HC P329G LALA + IL-10)

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Leu Gly Asn Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Gly Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg

```
                405                 410                 415
Trp Gln Gly Asn Val Phe Ser Cys Ser Val Met His Glu Ala Leu
            420                 425                 430

His Asn His Tyr Thr Gln Lys Ser Leu Ser Leu Ser Pro Gly Gly Gly
        435                 440                 445

Gly Gly Ser Gly Gly Gly Ser Gly Gly Gly Ser Gly Gly Gly
        450                 455                 460

Gly Ser Pro Gly Gln Gly Thr Gln Ser Glu Asn Ser Cys Thr His
465                 470                 475                 480

Phe Pro Gly Asn Leu Pro Asn Met Leu Arg Asp Leu Arg Asp Ala Phe
                485                 490                 495

Ser Arg Val Lys Thr Phe Phe Gln Met Lys Asp Gln Leu Asp Asn Leu
            500                 505                 510

Leu Leu Lys Glu Ser Leu Leu Glu Asp Phe Lys Gly Tyr Leu Gly Cys
            515                 520                 525

Gln Ala Leu Ser Glu Met Ile Gln Phe Tyr Leu Glu Glu Val Met Pro
        530                 535                 540

Gln Ala Glu Asn Gln Asp Pro Asp Ile Lys Ala His Val Asn Ser Leu
545                 550                 555                 560

Gly Glu Asn Leu Lys Thr Leu Arg Leu Arg Leu Arg Arg Cys His Arg
                565                 570                 575

Phe Leu Pro Cys Glu Asn Lys Ser Lys Ala Val Glu Gln Val Lys Asn
            580                 585                 590

Ala Phe Asn Lys Leu Gln Glu Lys Gly Ile Tyr Lys Ala Met Ser Glu
            595                 600                 605

Phe Asp Ile Phe Ile Asn Tyr Ile Glu Ala Tyr Met Thr Met Lys Ile
        610                 615                 620

Arg Asn
625

<210> SEQ ID NO 10
<211> LENGTH: 1878
<212> TYPE: DNA
<213> ORGANISM: Artificial Sequence
<220> FEATURE:
<223> OTHER INFORMATION: 4G8 IgG - IL-10 (HC P329G LALA + IL-10)

<400> SEQUENCE: 10
gaggtgcaat tgttggagtc tgggggaggc ttggtacagc ctggggggtc cctgagactc      60
tcctgtgcag cctccggatt caccttagc agttatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcagatga acagcctgag agccgaggac acggccgtat attactgtgc gaaagggtgg     300
ctgggtaatt ttgactactg gggccaagga accctggtca ccgtctcgag tgctagcacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga agttgagcc caaatcttgt     660 gacaaaactc acacatgccc accgtgccca gcacctgaag ctgcaggggg accgtcagtc     720
ttcctcttcc cccaaaaacc caaggacacc ctcatgatct cccggacccc tgaggtcaca     780
```

```
tgcgtggtgg tggacgtgag ccacgaagac cctgaggtca agttcaactg gtacgtggac      840
ggcgtggagg tgcataatgc caagacaaag ccgcgggagg agcagtacaa cagcacgtac      900
cgtgtggtca gcgtcctcac cgtcctgcac caggactggc tgaatggcaa ggagtacaag      960
tgcaaggtct ccaacaaagc cctcggcgcc cccatcgaga aaaccatctc caaagccaaa     1020
gggcagcccc gagaaccaca ggtgtacacc ctgcccccat cccgggatga gctgaccaag     1080
aaccaggtca gcctgacctg cctggtcaaa ggcttctatc ccagcgacat cgccgtggag     1140
tgggagagca atgggcagcc ggagaacaac tacaagacca cgcctcccgt gctggactcc     1200
gacggctcct tcttcctcta cagcaagctc accgtggaca agagcaggtg gcagcagggg     1260
aacgtcttct catgctccgt gatgcatgag gctctgcaca accactacac gcagaagagc     1320
ctctccctgt ctccgggtgg cggagggggt tctggaggtg cggctccgg aggcggagga     1380 tctgggggag gcggaagtag cccgggccag ggcacccaga gcgagaacag ctgcacccac     1440
ttccccggca acctgcccaa catgctgcgg gacctgaggg acgccttcag cagagtgaaa     1500
accttcttcc agatgaagga ccagctggac aacctgctgc tgaaagagag cctgctggaa     1560
gatttcaagg gctacctggg ctgtcaggcc ctgagcgaga tgatccagtt ctacctggaa     1620
gaagtgatgc cccaggccga gaaccaggac cccgacatca aggcccacgt gaacagcctg     1680
ggcgagaacc tgaaaaccct gcggctgaga ctgcggcggt gccacagatt tctgccctgc     1740
gagaacaaga gcaaggccgt ggaacaggtg aagaacgcct tcaacaagct gcaggaaaag     1800
ggcatctaca aggccatgtc cgagttcgac atcttcatca actacatcga agcttacatg     1860
acaatgaaaa tccgcaat                                                   1878

<210> SEQ ID NO 11
<211> LENGTH: 801
<212> TYPE: PRT
<213> ORGANISM: Artificial Sequence
<220> FEATURE:
<223> OTHER INFORMATION: 4G8 IgG - scIL-10 (HC hole P329G LALA + scIL-
      10)

<400> SEQUENCE: 11

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Leu Gly Asn Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160
```

```
Gly Ala Leu Thr Ser Val His Thr Phe Pro Ala Val Leu Gln Ser
            165                 170                 175

Ser Gly Leu Tyr Ser Leu Ser Ser Val Val Thr Val Pro Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
        210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Gly Ala Pro Ile Glu Lys Thr Ile
            325                 330                 335

Ser Lys Ala Lys Gly Gln Pro Arg Glu Pro Gln Val Cys Thr Leu Pro
            340                 345                 350

Pro Ser Arg Asp Glu Leu Thr Lys Asn Gln Val Ser Leu Ser Cys Ala
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Val Ser Lys Leu Thr Val Asp Lys Ser Arg
            405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Gly Gly
            435                 440                 445

Gly Gly Ser Gly Gly Gly Ser Gly Gly Gly Ser Ser Pro Gly
            450                 455                 460

Gln Gly Thr Gln Ser Glu Asn Ser Cys Thr His Phe Pro Gly Asn Leu
465                 470                 475                 480

Pro Asn Met Leu Arg Asp Leu Arg Asp Ala Phe Ser Arg Val Lys Thr
            485                 490                 495

Phe Phe Gln Met Lys Asp Gln Leu Asp Asn Leu Leu Leu Lys Glu Ser
            500                 505                 510

Leu Leu Glu Asp Phe Lys Gly Tyr Leu Gly Cys Gln Ala Leu Ser Glu
            515                 520                 525

Met Ile Gln Phe Tyr Leu Glu Glu Val Met Pro Gln Ala Glu Asn Gln
            530                 535                 540

Asp Pro Asp Ile Lys Ala His Val Asn Ser Leu Gly Glu Asn Leu Lys
545                 550                 555                 560

Thr Leu Arg Leu Arg Leu Arg Arg Cys His Arg Phe Leu Pro Cys Glu
            565                 570                 575
```

Asn Lys Ser Lys Ala Val Glu Gln Val Lys Asn Ala Phe Asn Lys Leu
            580                 585                 590

Gln Glu Lys Gly Ile Tyr Lys Ala Met Ser Glu Phe Asp Ile Phe Ile
        595                 600                 605

Asn Tyr Ile Glu Ala Tyr Met Thr Met Lys Ile Arg Asn Gly Gly Gly
    610                 615                 620

Gly Ser Gly Gly Gly Ser Gly Gly Gly Ser Gly Gly Gly Gly
625                 630                 635                 640

Ser Ser Pro Gly Gln Gly Thr Gln Ser Glu Asn Ser Cys Thr His Phe
                645                 650                 655

Pro Gly Asn Leu Pro Asn Met Leu Arg Asp Leu Arg Asp Ala Phe Ser
            660                 665                 670

Arg Val Lys Thr Phe Phe Gln Met Lys Asp Gln Leu Asp Asn Leu Leu
        675                 680                 685

Leu Lys Glu Ser Leu Leu Glu Asp Phe Lys Gly Tyr Leu Gly Cys Gln
    690                 695                 700

Ala Leu Ser Glu Met Ile Gln Phe Tyr Leu Glu Glu Val Met Pro Gln
705                 710                 715                 720

Ala Glu Asn Gln Asp Pro Asp Ile Lys Ala His Val Asn Ser Leu Gly
                725                 730                 735

Glu Asn Leu Lys Thr Leu Arg Leu Arg Leu Arg Arg Cys His Arg Phe
            740                 745                 750

Leu Pro Cys Glu Asn Lys Ser Lys Ala Val Glu Gln Val Lys Asn Ala
        755                 760                 765

Phe Asn Lys Leu Gln Glu Lys Gly Ile Tyr Lys Ala Met Ser Glu Phe
    770                 775                 780

Asp Ile Phe Ile Asn Tyr Ile Glu Ala Tyr Met Thr Met Lys Ile Arg
785                 790                 795                 800

Asn

<210> SEQ ID NO 12
<211> LENGTH: 2403
<212> TYPE: DNA
<213> ORGANISM: Artificial Sequence
<220> FEATURE:
<223> OTHER INFORMATION: 4G8 IgG - scIL-10 (HC hole P329G LALA + scIL-
      10)

<400> SEQUENCE: 12
gaggtgcaat tgttggagtc tggggggaggc ttggtacagc ctgggggggtc cctgagactc      60 tcctgtgcag cctccggatt cacctttagc agttatgcca tgagctgggt ccgccaggct     120
ccagggaagg ggctggagtg gtctcagct attagtggta gtggtggtag cacatactac     180
gcagactccg tgaagggccg gttcaccatc tccagagaca attccaagaa cacgctgtat     240
ctgcagatga acagcctgag agccgaggac acggccgtat attactgtgc gaaagggtgg     300
ctgggtaatt ttgactactg gggccaagga accctggtca ccgtctcgag tgctagcacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga agttgagcc caaatcttgt     660 gacaaaactc acacatgccc accgtgccca gcacctgaag ctgcaggggg accgtcagtc     720

-continued

| | |
|---|---|
| ttcctcttcc ccccaaaacc caaggacacc ctcatgatct cccggacccc tgaggtcaca | 780 |
| tgcgtggtgg tggacgtgag ccacgaagac cctgaggtca agttcaactg gtacgtggac | 840 |
| ggcgtggagg tgcataatgc caagacaaag ccgcgggagg agcagtacaa cagcacgtac | 900 |
| cgtgtggtca gcgtcctcac cgtcctgcac caggactggc tgaatggcaa ggagtacaag | 960 |
| tgcaaggtct ccaacaaagc cctcggcgcc cccatcgaga aaaccatctc caaagccaaa | 1020 |
| gggcagcccc gagaaccaca ggtgtgcacc ctgcccccat cccgggatga gctgaccaag | 1080 |
| aaccaggtca gcctctcgtg cgcagtcaaa ggcttctatc cagcgacat cgccgtggag | 1140 |
| tgggagagca atgggcagcc ggagaacaac tacaagacca cgcctcccgt gctggactcc | 1200 |
| gacggctcct tcttcctcgt gagcaagctc accgtggaca agagcaggtg gcagcagggg | 1260 |
| aacgtcttct catgctccgt gatgcatgag gctctgcaca accactacac gcagaagagc | 1320 |
| ctctccctgt ctccgggtgg cggcggaggc tccggaggcg aggatctggg ggaggcgga | 1380 |
| agtagcccgg gccagggcac ccagagcgag aacagctgca cccacttccc cggcaacctg | 1440 |
| cccaacatgc tgcgggacct gagggacgcc ttcagcagag tgaaaacctt cttccagatg | 1500 |
| aaggaccagc tggacaacct gctgctgaaa gagagcctgc tggaagattt caagggctac | 1560 |
| ctgggctgtc aggccctgag cgagatgatc cagttctacc tggaagaagt gatgccccag | 1620 |
| gccgagaacc aggaccccga catcaaggcc cacgtgaaca gcctgggcga gaacctgaaa | 1680 |
| accctgcggc tgagactgcg gcggtgccac agatttctgc cctgcgagaa caagagcaag | 1740 |
| gccgtggaac aggtgaagaa cgccttcaac aagctgcagg aaaagggcat ctacaaggcc | 1800 |
| atgtccgagt cgacatctt catcaactac atcgaagctt acatgaccat gaagatcaga | 1860 |
| aacggcggag gcggatctgg cggcggtgga agtggaggcg gaggatctgg gggaggcgga | 1920 |
| agtagcccgg gccagggcac ccagagcgag aacagctgca cccacttccc cggcaacctg | 1980 |
| cccaacatgc tgcgggacct gagggacgcc ttcagcagag tgaaaacctt cttccagatg | 2040 |
| aaggaccagc tggacaacct gctgctgaaa gagagcctgc tggaagattt caagggctac | 2100 |
| ctgggctgtc aggccctgag cgagatgatc cagttctacc tggaagaagt gatgccccag | 2160 |
| gccgagaacc aggaccccga catcaaggcc cacgtgaaca gcctgggcga gaacctgaaa | 2220 |
| accctgcggc tgagactgcg gcggtgccac agatttctgc cctgcgagaa caagagcaag | 2280 |
| gccgtggaac aggtgaagaa cgccttcaac aagctgcagg aaaagggcat ctacaaggcc | 2340 |
| atgtccgagt cgacatctt catcaactac atcgaggcct acatgacaat gaaaatccgc | 2400 |
| aat | 2403 |

<210> SEQ ID NO 13
<211> LENGTH: 447
<212> TYPE: PRT
<213> ORGANISM: Artificial Sequence
<220> FEATURE:
<223> OTHER INFORMATION: 4G8 IgG - scIL-10 (HC knob P329G LALA)

<400> SEQUENCE: 13

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Gly Trp Leu Gly Asn Phe Asp Tyr Trp Gly Gln Gly Thr Leu
        100                 105                 110

Val Thr Val Ser Ser Ala Ser Thr Lys Gly Pro Ser Val Phe Pro Leu
    115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Gly Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Cys Arg Asp Glu Leu Thr Lys Asn Gln Val Ser Leu Trp Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 14
<211> LENGTH: 1341
<212> TYPE: DNA
<213> ORGANISM: Artificial Sequence
<220> FEATURE:

<223> OTHER INFORMATION: 4G8 IgG - scIL-10 (HC knob P329G LALA)

<400> SEQUENCE: 14

```
gaggtgcaat tgttggagtc tgggggaggc ttggtacagc ctggggggtc cctgagactc      60
tcctgtgcag cctccggatt cacctttagc agttatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcagatga acagcctgag agccgaggac acggccgtat attactgtgc aaagggtgg      300
ctgggtaatt ttgactactg gggccaagga accctggtca ccgtctcgag tgctagcacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga agttgagcc caaatcttgt      660
gacaaaactc acacatgccc accgtgccca gcacctgaag ctgcagggg accgtcagtc      720
ttcctcttcc cccaaaaccc aaggacaccc tcatgatctc ccggacccc tgaggtcaca      780
tgcgtggtgg tggacgtgag ccacgaagac cctgaggtca agttcaactg gtacgtggac     840
ggcgtggagg tgcataatgc caagacaaag ccgcgggagg agcagtacaa cagcacgtac     900
cgtgtggtca gcgtcctcac cgtcctgcac caggactggc tgaatggcaa ggagtacaag     960
tgcaaggtct ccaacaaagc cctcggcgcc cccatcgaga aaaccatctc caaagccaaa    1020
gggcagcccc gagaaccaca ggtgtacacc ctgcccccat gccgggatga gctgaccaag    1080
aaccaggtca gcctgtggtg cctggtcaaa ggcttctatc ccagcgacat cgccgtggag    1140
tgggagagca atgggcagcc ggagaacaac tacaagacca cgcctcccgt gctggactcc    1200
gacggctcct tcttcctcta cagcaagctc accgtggaca gagcaggtg gcagcagggg     1260
aacgtcttct catgctccgt gatgcatgag gctctgcaca accactacac gcagaagagc    1320
ctctccctgt ctccgggtaa a                                              1341
```

<210> SEQ ID NO 15
<211> LENGTH: 627
<212> TYPE: PRT
<213> ORGANISM: Artificial Sequence
<220> FEATURE:
<223> OTHER INFORMATION: 4G8 IgG -IL-10M1 (HC hole P329G LALA + IL-10M1)

<400> SEQUENCE: 15

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Trp Leu Gly Asn Phe Asp Tyr Trp Gly Gln Gly Thr Leu
```

```
            100             105             110
Val Thr Val Ser Ser Ala Ser Thr Lys Gly Pro Ser Val Phe Pro Leu
            115             120             125
Ala Pro Ser Ser Lys Ser Thr Ser Gly Gly Thr Ala Ala Leu Gly Cys
            130             135             140
Leu Val Lys Asp Tyr Phe Pro Glu Pro Val Thr Val Ser Trp Asn Ser
145             150             155             160
Gly Ala Leu Thr Ser Gly Val His Thr Phe Pro Ala Val Leu Gln Ser
            165             170             175
Ser Gly Leu Tyr Ser Leu Ser Ser Val Val Thr Val Pro Ser Ser Ser
            180             185             190
Leu Gly Thr Gln Thr Tyr Ile Cys Asn Val Asn His Lys Pro Ser Asn
            195             200             205
Thr Lys Val Asp Lys Lys Val Glu Pro Lys Ser Cys Asp Lys Thr His
            210             215             220
Thr Cys Pro Pro Cys Pro Ala Pro Glu Ala Ala Gly Gly Pro Ser Val
225             230             235             240
Phe Leu Phe Pro Pro Lys Pro Lys Asp Thr Leu Met Ile Ser Arg Thr
            245             250             255
Pro Glu Val Thr Cys Val Val Val Asp Val Ser His Glu Asp Pro Glu
            260             265             270
Val Lys Phe Asn Trp Tyr Val Asp Gly Val Glu Val His Asn Ala Lys
            275             280             285
Thr Lys Pro Arg Glu Glu Gln Tyr Asn Ser Thr Tyr Arg Val Val Ser
            290             295             300
Val Leu Thr Val Leu His Gln Asp Trp Leu Asn Gly Lys Glu Tyr Lys
305             310             315             320
Cys Lys Val Ser Asn Lys Ala Leu Gly Ala Pro Ile Glu Lys Thr Ile
            325             330             335
Ser Lys Ala Lys Gly Gln Pro Arg Glu Pro Gln Val Cys Thr Leu Pro
            340             345             350
Pro Ser Arg Asp Glu Leu Thr Lys Asn Gln Val Ser Leu Ser Cys Ala
            355             360             365
Val Lys Gly Phe Tyr Pro Ser Asp Ile Ala Val Glu Trp Glu Ser Asn
            370             375             380
Gly Gln Pro Glu Asn Asn Tyr Lys Thr Thr Pro Pro Val Leu Asp Ser
385             390             395             400
Asp Gly Ser Phe Phe Leu Val Ser Lys Leu Thr Val Asp Lys Ser Arg
            405             410             415
Trp Gln Gln Gly Asn Val Phe Ser Cys Ser Val Met His Glu Ala Leu
            420             425             430
His Asn His Tyr Thr Gln Lys Ser Leu Ser Leu Ser Pro Gly Gly Gly
            435             440             445
Gly Gly Ser Gly Gly Gly Ser Gly Gly Gly Gly Ser Ser Pro Gly
            450             455             460
Gln Gly Thr Gln Ser Glu Asn Ser Cys Thr His Phe Pro Gly Asn Leu
465             470             475             480
Pro Asn Met Leu Arg Asp Leu Arg Asp Ala Phe Ser Arg Val Lys Thr
            485             490             495
Phe Phe Gln Met Lys Asp Gln Leu Asp Asn Leu Leu Leu Lys Glu Ser
            500             505             510
Leu Leu Glu Asp Phe Lys Gly Tyr Leu Gly Cys Gln Ala Leu Ser Glu
            515             520             525
```

```
Met Ile Gln Phe Tyr Leu Glu Glu Val Met Pro Gln Ala Glu Asn Gln
    530                 535                 540

Asp Pro Asp Ile Lys Ala His Val Asn Ser Leu Gly Glu Asn Leu Lys
545                 550                 555                 560

Thr Leu Arg Leu Arg Leu Arg Arg Cys His Arg Phe Leu Pro Cys Glu
                565                 570                 575

Asn Gly Gly Gly Ser Gly Gly Lys Ser Lys Ala Val Glu Gln Val Lys
            580                 585                 590

Asn Ala Phe Asn Lys Leu Gln Glu Lys Gly Ile Tyr Lys Ala Met Ser
        595                 600                 605

Glu Phe Asp Ile Phe Ile Asn Tyr Ile Glu Ala Tyr Met Thr Met Lys
610                 615                 620

Ile Arg Asn
625
```

<210> SEQ ID NO 16
<211> LENGTH: 1881
<212> TYPE: DNA
<213> ORGANISM: Artificial Sequence
<220> FEATURE:
<223> OTHER INFORMATION: 4G8 IgG -IL-10M1 (HC hole P329G LALA + IL-10M1)

<400> SEQUENCE: 16

```
gaggtgcaat tgttggagtc tgggggaggc ttggtacagc ctggggggtc cctgagactc     60
tcctgtgcag cctccggatt cacctttagc agttatgcca tgagctgggt ccgccaggct    120
ccagggaagg gctggagtg gtctcagct attagtggta gtggtggtag cacatactac      180
gcagactccg tgaagggccg gttcaccatc tccagagaca attccaagaa cacgctgtat    240
ctgcagatga acagcctgag agccgaggac acggccgtat attactgtgc gaaagggtgg   300
ctgggtaatt ttgactactg gggccaagga accctggtca ccgtctcgag tgctagcacc   360
aagggcccat cggtcttccc cctggcaccc tcctccaaga gcacctctgg gggcacagcg   420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga agttgagcc caaatcttgt     660
gacaaaactc acacatgccc accgtgccca gcacctgaag ctgcaggggg accgtcagtc    720
ttcctcttcc cccccaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgtgtggtca gcgtcctcac cgtcctgcac caggactggc tgaatggcaa ggagtacaag    960
tgcaaggtct ccaacaaagc cctcggcgcc cccatcgaga aaaccatctc caaagccaaa   1020
gggcagcccc gagaaccaca ggtgtgcacc ctgcccccat cccgggatga gctgaccaag   1080
aaccaggtca gcctctcgtg cgcagtcaaa ggcttctatc ccagcgacat cgccgtggag   1140
tgggagagca atgggcagcc ggagaacaac tacaagacca cgcctcccgt gctggactcc   1200
gacggctcct tcttcctcgt gagcaagctc accgtggaca agagcaggtg gcagcagggg   1260
aacgtcttct catgctccgt gatgcatgag gctctgcaca accactacac gcagaagagc   1320
ctctcccctgt ctccgggtgg cggcggaggc tccggaggcg aggaagtgg cggcggtggc   1380
agctctccag gccagggcac ccagagcgag aacagctgca cccacttccc cggcaacctg   1440
```

```
cccaacatgc tgcgggacct gagggacgcc ttcagcagag tgaaaacctt cttccagatg   1500
aaggaccagc tggacaacct gctgctgaaa gagagcctgc tggaagattt caagggctac   1560
ctgggctgtc aggccctgag cgagatgatc cagttctacc tggaagaagt gatgccccag   1620
gccgagaacc aggaccccga catcaaggcc acgtgaaca gcctgggcga aaacctgaaa    1680
accctgcggc tgagactgcg gcggtgccac agatttctgc cctgcgagaa cggcggaggc   1740
tctggcggaa agtccaaggc cgtggaacag gtgaagaacg ccttcaacaa gctgcaggaa   1800
aagggcatct acaaggccat gagcgagttc gacatcttca tcaactacat cgaagcttac   1860
atgacaatga agatacgaaa c                                             1881
```

<210> SEQ ID NO 17
<211> LENGTH: 627
<212> TYPE: PRT
<213> ORGANISM: Artificial Sequence
<220> FEATURE:
<223> OTHER INFORMATION: 4G8 IgG -(IL-10M1)2 (HC P329G LALA + IL-10M1)

<400> SEQUENCE: 17

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Leu Gly Asn Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
```

-continued

```
                    275                 280                 285
Thr Lys Pro Arg Glu Glu Gln Tyr Asn Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Ala Leu Gly Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Gly Gly
        435                 440                 445

Gly Gly Ser Gly Gly Gly Ser Gly Gly Gly Ser Ser Pro Gly
450                 455                 460

Gln Gly Thr Gln Ser Glu Asn Ser Cys Thr His Phe Pro Gly Asn Leu
465                 470                 475                 480

Pro Asn Met Leu Arg Asp Leu Arg Asp Ala Phe Ser Arg Val Lys Thr
                485                 490                 495

Phe Phe Gln Met Lys Asp Gln Leu Asp Asn Leu Leu Leu Lys Glu Ser
            500                 505                 510

Leu Leu Glu Asp Phe Lys Gly Tyr Leu Gly Cys Gln Ala Leu Ser Glu
        515                 520                 525

Met Ile Gln Phe Tyr Leu Glu Glu Val Met Pro Gln Ala Glu Asn Gln
530                 535                 540

Asp Pro Asp Ile Lys Ala His Val Asn Ser Leu Gly Glu Asn Leu Lys
545                 550                 555                 560

Thr Leu Arg Leu Arg Leu Arg Arg Cys His Arg Phe Leu Pro Cys Glu
                565                 570                 575

Asn Gly Gly Gly Ser Gly Gly Lys Ser Lys Ala Val Glu Gln Val Lys
            580                 585                 590

Asn Ala Phe Asn Lys Leu Gln Glu Lys Gly Ile Tyr Lys Ala Met Ser
        595                 600                 605

Glu Phe Asp Ile Phe Ile Asn Tyr Ile Glu Ala Tyr Met Thr Met Lys
    610                 615                 620

Ile Arg Asn
625

<210> SEQ ID NO 18
<211> LENGTH: 1881
<212> TYPE: DNA
<213> ORGANISM: Artificial Sequence
<220> FEATURE:
<223> OTHER INFORMATION: 4G8 IgG -(IL-10M1)2 (HC P329G LALA + IL-10M1)

<400> SEQUENCE: 18
gaggtgcaat tgttggagtc tgggggaggc ttggtacagc ctggggggtc cctgagactc    60
```

-continued

```
tcctgtgcag cctccggatt cacctttagc agttatgcca tgagctgggt ccgccaggct      120
ccagggaagg ggctggagtg ggtctcagct attagtggta gtggtggtag cacatactac      180
gcagactccg tgaagggccg gttcaccatc tccagagaca attccaagaa cacgctgtat      240
ctgcagatga acagcctgag agccgaggac acggccgtat attactgtgc gaaaggtgg       300 ctgggtaatt ttgactactg gggccaagga accctggtca ccgtctcgag tgctagcacc      360
aagggcccat cggtcttccc cctggcaccc tcctccaaga gcacctctgg gggcacagcg      420
gccctgggct gcctggtcaa ggactacttc cccgaaccgg tgacggtgtc gtggaactca      480
ggcgccctga ccagcggcgt gcacaccttc ccggctgtcc tacagtcctc aggactctac      540
tccctcagca gcgtggtgac cgtgccctcc agcagcttgg gcacccagac ctacatctgc      600
aacgtgaatc acaagcccag caacaccaag gtggacaaga agttgagcc caaatcttgt      660 gacaaaactc acacatgccc accgtgccca gcacctgaag ctgcaggggg accgtcagtc      720
ttcctcttcc cccaaaaccc aaggacaccc tcatgatctc ccggacccc tgaggtcaca      780 tgcgtggtgg tggacgtgag ccacgaagac cctgaggtca agttcaactg gtacgtggac      840
ggcgtggagg tgcataatgc caagacaaag ccgcgggagg agcagtacaa cagcacgtac      900
cgtgtggtca gcgtcctcac cgtcctgcac caggactggc tgaatggcaa ggagtacaag      960
tgcaaggtct ccaacaaagc cctcggcgcc cccatcgaga aaaccatctc caaagccaaa     1020
gggcagcccc gagaaccaca ggtgtacacc ctgcccccat cccgggatga gctgaccaag     1080
aaccaggtca gcctgacctg cctggtcaaa ggcttctatc ccagcgacat cgccgtggag     1140
tgggagagca atgggcagcc ggagaacaac tacaagacca cgcctcccgt gctggactcc     1200
gacggctcct tcttcctcta cagcaagctc accgtggaca agagcaggtg gcagcagggg     1260
aacgtcttct catgctccgt gatgcatgag gctctgcaca accactacac gcagaagagc     1320
ctctccctgt ctccgggtgg cggcggaggc tccggaggcg gaggaagtgg cggcggtggc     1380
agctctccag gccagggcac ccagagcgag aacagctgca cccacttccc cggcaacctg     1440
cccaacatgc tgcgggacct gagggacgcc ttcagcagag tgaaaacctt cttccagatg     1500
aaggaccagc tggacaacct gctgctgaaa gagagcctgc tggaagattt caagggctac     1560
ctgggctgtc aggccctgag cgagatgatc cagttctacc tggaagaagt gatgccccag     1620
gccgagaacc aggaccccga catcaaggcc acgtgaaca gctgggcga gaacctgaaa     1680 accctgcggc tgagactgcg gcggtgccac agatttctgc cctgcgagaa cggcggaggc     1740
tctggcggaa agtccaaggc cgtggaacag gtgaagaacg ccttcaacaa gctgcaggaa     1800
aagggcatct acaaggccat gagcgagttc gacatcttca tcaactacat cgaagcttac     1860
atgacaatga agatacgaaa c                                                1881
```

<210> SEQ ID NO 19
<211> LENGTH: 396
<212> TYPE: PRT
<213> ORGANISM: Artificial Sequence
<220> FEATURE:
<223> OTHER INFORMATION: 4G8 Fab - IL-10 (HC + IL-10)

<400> SEQUENCE: 19

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30
```

```
Ala Met Ser Trp Val Arg Gln Ala Pro Gly Lys Gly Leu Glu Trp Val
            35                  40                  45
Ser Ala Ile Ser Gly Ser Gly Gly Ser Thr Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                85                  90                  95
Ala Lys Gly Trp Leu Gly Asn Phe Asp Tyr Trp Gly Gln Gly Thr Leu
            100                 105                 110
Val Thr Val Ser Ser Ala Ser Thr Lys Gly Pro Ser Val Phe Pro Leu
            115                 120                 125
Ala Pro Ser Ser Lys Ser Thr Ser Gly Gly Thr Ala Ala Leu Gly Cys
            130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
            195                 200                 205
Thr Lys Val Asp Lys Lys Val Glu Pro Lys Ser Cys Asp Gly Gly Gly
            210                 215                 220
Gly Ser Gly Gly Gly Gly Ser Gly Gly Gly Gly Ser Ser Pro Gly Gln
225                 230                 235                 240
Gly Thr Gln Ser Glu Asn Ser Cys Thr His Phe Pro Gly Asn Leu Pro
                245                 250                 255
Asn Met Leu Arg Asp Leu Arg Asp Ala Phe Ser Arg Val Lys Thr Phe
            260                 265                 270
Phe Gln Met Lys Asp Gln Leu Asp Asn Leu Leu Leu Lys Glu Ser Leu
            275                 280                 285
Leu Glu Asp Phe Lys Gly Tyr Leu Gly Cys Gln Ala Leu Ser Glu Met
            290                 295                 300
Ile Gln Phe Tyr Leu Glu Glu Val Met Pro Gln Ala Glu Asn Gln Asp
305                 310                 315                 320
Pro Asp Ile Lys Ala His Val Asn Ser Leu Gly Glu Asn Leu Lys Thr
                325                 330                 335
Leu Arg Leu Arg Leu Arg Arg Cys His Arg Phe Leu Pro Cys Glu Asn
            340                 345                 350
Lys Ser Lys Ala Val Glu Gln Val Lys Asn Ala Phe Asn Lys Leu Gln
            355                 360                 365
Glu Lys Gly Ile Tyr Lys Ala Met Ser Glu Phe Asp Ile Phe Ile Asn
            370                 375                 380
Tyr Ile Glu Ala Tyr Met Thr Met Lys Ile Arg Asn
385                 390                 395

<210> SEQ ID NO 20
<211> LENGTH: 1188
<212> TYPE: DNA
<213> ORGANISM: Artificial Sequence
<220> FEATURE:
<223> OTHER INFORMATION: 4G8 Fab - IL-10 (HC + IL-10)

<400> SEQUENCE: 20
```

-continued

```
gaggtgcaat tgttggagtc tgggggaggc ttggtacagc ctggggggtc cctgagactc        60
tcctgtgcag cctccggatt cacctttagc agttatgcca tgagctgggt ccgccaggct       120
ccagggaagg ggctggagtg ggtctcagct attagtggta gtggtggtag cacatactac       180
gcagactccg tgaagggccg gttcaccatc tccagagaca attccaagaa cacgctgtat       240
ctgcagatga acagcctgag agccgaggac acggccgtat attactgtgc gaaaggtgg        300
ctgggtaatt ttgactactg gggccaagga accctggtca ccgtctcgag tgctagcacc       360
aagggcccca gcgtgtttcc tctggccccc agcagcaaga gcacaagcgg cggaacagcc       420
gccctgggct gcctggtgaa ggactacttc cccgagcccg tgaccgtgtc ttggaacagc       480
ggagccctga ccagcggcgt gcacaccttt ccagccgtgc tgcagagcag cggcctgtac       540
agcctgagca gcgtggtgac cgtgcctagc agcagcctgg gcacccagac ctacatctgc       600
aacgtgaacc acaagcccag caacaccaag gtggacaaga aggtggagcc caagagctgt       660
gatggcggcg gaggctccgg aggcggagga tctgggggag gcggaagtag cccgggccag       720
ggcacccaga gcgagaacag ctgcacccac ttccccggca acctgcccaa catgctgcgg       780
gacctgaggg acgccttcag cagagtgaaa accttcttcc agatgaagga ccagctggac       840
aacctgctgc tgaaagagag cctgctggaa gatttcaagg gctacctggg ctgtcaggcc       900
ctgagcgaga tgatccagtt ctacctggaa gaagtgatgc cccaggccga gaaccaggac       960
cccgacatca aggcccacgt gaacagcctg ggcgagaacc tgaaaaccct gcggctgaga      1020
ctgcggcggt gccacagatt tctgccctgc gagaacaaga gcaaggccgt ggaacaggtg      1080
aagaacgcct tcaacaagct gcaggaaaag ggcatctaca aggccatgtc cgagttcgac      1140
atcttcatca actacatcga agcttacatg acaatgaaaa tccgcaat                   1188
```

<210> SEQ ID NO 21
<211> LENGTH: 812
<212> TYPE: PRT
<213> ORGANISM: Artificial Sequence
<220> FEATURE:
<223> OTHER INFORMATION: 4G8 Fab - scIL-10 - Fab (HC + scIL-10 + HC)

<400> SEQUENCE: 21

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Leu Gly Asn Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160
```

```
Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Gly Gly Gly
        210                 215                 220

Gly Ser Gly Gly Gly Gly Ser Gly Gly Gly Gly Ser Ser Pro Gly Gln
225                 230                 235                 240

Gly Thr Gln Ser Glu Asn Ser Cys Thr His Phe Pro Gly Asn Leu Pro
            245                 250                 255

Asn Met Leu Arg Asp Leu Arg Asp Ala Phe Ser Arg Val Lys Thr Phe
            260                 265                 270

Phe Gln Met Lys Asp Gln Leu Asp Asn Leu Leu Leu Lys Glu Ser Leu
        275                 280                 285

Leu Glu Asp Phe Lys Gly Tyr Leu Gly Cys Gln Ala Leu Ser Glu Met
        290                 295                 300

Ile Gln Phe Tyr Leu Glu Glu Val Met Pro Gln Ala Glu Asn Gln Asp
305                 310                 315                 320

Pro Asp Ile Lys Ala His Val Asn Ser Leu Gly Glu Asn Leu Lys Thr
            325                 330                 335

Leu Arg Leu Arg Leu Arg Arg Cys His Arg Phe Leu Pro Cys Glu Asn
            340                 345                 350

Lys Ser Lys Ala Val Glu Gln Val Lys Asn Ala Phe Asn Lys Leu Gln
            355                 360                 365

Glu Lys Gly Ile Tyr Lys Ala Met Ser Glu Phe Asp Ile Phe Ile Asn
        370                 375                 380

Tyr Ile Glu Ala Tyr Met Thr Met Lys Ile Arg Asn Gly Gly Gly Gly
385                 390                 395                 400

Ser Gly Gly Gly Gly Ser Gly Gly Gly Gly Ser Gly Gly Gly Gly Ser
            405                 410                 415

Ser Pro Gly Gln Gly Thr Gln Ser Glu Asn Ser Cys Thr His Phe Pro
            420                 425                 430

Gly Asn Leu Pro Asn Met Leu Arg Asp Leu Arg Asp Ala Phe Ser Arg
            435                 440                 445

Val Lys Thr Phe Phe Gln Met Lys Asp Gln Leu Asp Asn Leu Leu Leu
        450                 455                 460

Lys Glu Ser Leu Leu Glu Asp Phe Lys Gly Tyr Leu Gly Cys Gln Ala
465                 470                 475                 480

Leu Ser Glu Met Ile Gln Phe Tyr Leu Glu Glu Val Met Pro Gln Ala
            485                 490                 495

Glu Asn Gln Asp Pro Asp Ile Lys Ala His Val Asn Ser Leu Gly Glu
            500                 505                 510

Asn Leu Lys Thr Leu Arg Leu Arg Leu Arg Arg Cys His Arg Phe Leu
            515                 520                 525

Pro Cys Glu Asn Lys Ser Lys Ala Val Glu Gln Val Lys Asn Ala Phe
        530                 535                 540

Asn Lys Leu Gln Glu Lys Gly Ile Tyr Lys Ala Met Ser Glu Phe Asp
545                 550                 555                 560

Ile Phe Ile Asn Tyr Ile Glu Ala Tyr Met Thr Met Lys Ile Arg Asn
            565                 570                 575
```

```
Gly Gly Gly Gly Ser Gly Gly Gly Ser Gly Gly Gly Ser Glu
            580                 585                 590

Val Gln Leu Leu Glu Ser Gly Gly Gly Leu Val Gln Pro Gly Gly Ser
        595                 600                 605

Leu Arg Leu Ser Cys Ala Ala Ser Gly Phe Thr Phe Ser Ser Tyr Ala
    610                 615                 620

Met Ser Trp Val Arg Gln Ala Pro Gly Lys Gly Leu Glu Trp Val Ser
625                 630                 635                 640

Ala Ile Ser Gly Ser Gly Gly Ser Thr Tyr Tyr Ala Asp Ser Val Lys
                645                 650                 655

Gly Arg Phe Thr Ile Ser Arg Asp Asn Ser Lys Asn Thr Leu Tyr Leu
            660                 665                 670

Gln Met Asn Ser Leu Arg Ala Glu Asp Thr Ala Val Tyr Tyr Cys Ala
        675                 680                 685

Lys Gly Trp Leu Gly Asn Phe Asp Tyr Trp Gly Gln Gly Thr Leu Val
    690                 695                 700

Thr Val Ser Ser Ala Ser Thr Lys Gly Pro Ser Val Phe Pro Leu Ala
705                 710                 715                 720

Pro Ser Ser Lys Ser Thr Ser Gly Gly Thr Ala Ala Leu Gly Cys Leu
                725                 730                 735

Val Lys Asp Tyr Phe Pro Glu Pro Val Thr Val Ser Trp Asn Ser Gly
            740                 745                 750

Ala Leu Thr Ser Gly Val His Thr Phe Pro Ala Val Leu Gln Ser Ser
        755                 760                 765

Gly Leu Tyr Ser Leu Ser Ser Val Val Thr Val Pro Ser Ser Ser Leu
    770                 775                 780

Gly Thr Gln Thr Tyr Ile Cys Asn Val Asn His Lys Pro Ser Asn Thr
785                 790                 795                 800

Lys Val Asp Lys Lys Val Glu Pro Lys Ser Cys Asp
                805                 810

<210> SEQ ID NO 22
<211> LENGTH: 2436
<212> TYPE: DNA
<213> ORGANISM: Artificial Sequence
<220> FEATURE:
<223> OTHER INFORMATION: 4G8 Fab - scIL-10 - Fab (HC + scIL-10 + HC)

<400> SEQUENCE: 22
gaggtgcaat tgttggagtc tgggggaggc ttggtacagc ctgggggtc cctgagactc      60 tcctgtgcag cctccggatt caccttagc agttatgcca tgagctgggt ccgccaggct     120
ccagggaagg ggctggagtg ggtctcagct attagtggta gtggtggtag cacatactac    180
gcagactccg tgaagggccg gttcaccatc tccagagaca attccaagaa cacgctgtat    240
ctgcagatga acagcctgag agccgaggac acggccgtat attactgtgc gaaagggtgg    300
ctgggtaatt ttgactactg gggccaagga accctggtca ccgtctcgag tgctagcacc    360
aagggcccca gcgtgtttcc tctggccccc agcagcaaga gcacaagcgg cggaacagcc    420
gccctgggct gcctggtgaa ggactacttc cccgagcccg tgaccgtgtc ttggaacagc    480
ggagccctga ccagcggcgt gcacaccttt ccagccgtgc tgcagagcag cggcctgtac    540
agcctgagca gcgtggtgac cgtgcctagc agcagcctgg gcacccagac ctacatctgc    600
aacgtgaacc acaagcccag caacaccaag gtggacaaga aggtggagcc caagagctgt    660
gatggcggcg gaggctccgg aggcggagga tctgggggag gcggaagtag cccgggccag    720
```

```
ggcacccaga gcgagaacag ctgcacccac ttccccggca acctgcccaa catgctgcgg   780
gacctgaggg acgccttcag cagagtgaaa accttcttcc agatgaagga ccagctggac   840
aacctgctgc tgaaagagag cctgctggaa gatttcaagg gctacctggg ctgtcaggcc   900
ctgagcgaga tgatccagtt ctacctggaa gaagtgatgc cccaggccga aaccaggac    960
cccgacatca aggcccacgt gaacagcctg ggcgagaacc tgaaaaccct gcggctgaga  1020
ctgcggcggt gccacagatt tctgccctgc gagaacaaga gcaaggccgt ggaacaggtg  1080
aagaacgcct tcaacaagct gcaggaaaag ggcatctaca aggccatgtc cgagttcgac  1140
atcttcatca actacatcga agcttacatg accatgaaga tcagaaacgg cggaggcgga  1200
tctggcggcg gtggaagtgg aggcggagga tctgggggag gcggaagtag cccgggccag  1260
ggcacccaga gcgagaacag ctgcacccac ttccccggca acctgcccaa catgctgcgg  1320
gacctgaggg acgccttcag cagagtgaaa accttcttcc agatgaagga ccagctggac  1380
aacctgctgc tgaaagagag cctgctggaa gatttcaagg gctacctggg ctgtcaggcc  1440
ctgagcgaga tgatccagtt ctacctggaa gaagtgatgc cccaggccga aaccaggac   1500
cccgacatca aggcccacgt gaacagcctg ggcgagaacc tgaaaaccct gcggctgaga  1560
ctgcggcggt gccacagatt tctgccctgc gagaacaaga gcaaggccgt ggaacaggtg  1620
aagaacgcct tcaacaagct gcaggaaaag ggcatctaca aggccatgtc cgagttcgac  1680
atcttcatca actacatcga ggcctacatg acaatgaaaa tccgcaatgg cggggaggga  1740
tcaggtggag ggggcagcgg tggtggagga tccgaggtgc aattgttgga gtctggggga  1800
ggcttggtac agcctggggg gtccctgaga ctctcctgtg cagcctccgg attcaccttt  1860
agcagttatg ccatgagctg ggtccgccag gctccaggga aggggctgga gtgggtctca  1920
gctattagtg gtagtggtgg tagcacatac tacgcagact ccgtgaaggg ccggttcacc  1980
atctccagag acaattccaa gaacacgctg tatctgcaga tgaacagcct gagagccgag  2040
gacacggccg tatattactg tgcgaaaggg tggctgggta attttgacta ctggggccaa  2100
ggaaccctgg tcaccgtctc gagtgctagc accaagggcc catcggtctt ccccctggca  2160
ccctcctcca agagcacctc tgggggcaca gcggccctgg gctgcctggt caaggactac  2220
ttccccgaac cggtgacggt gtcgtggaac tcaggcgccc tgaccagcgg cgtgcacacc  2280
ttcccggctg tcctacagtc ctcaggactc tactccctca gcagcgtggt gaccgtgccc  2340
tccagcagct gggcaccca gacctacatc tgcaacgtga atcacaagcc cagcaacacc  2400
aaggtggata gaaagttga gcccaaatct tgtgac                             2436
```

<210> SEQ ID NO 23
<211> LENGTH: 638
<212> TYPE: PRT
<213> ORGANISM: Artificial Sequence
<220> FEATURE:
<223> OTHER INFORMATION: 4G8 Fab -IL-10M1 - Fab (HC + IL-10M1 + HC)

<400> SEQUENCE: 23

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Trp Leu Gly Asn Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Gly Gly Gly
    210                 215                 220

Gly Ser Gly Gly Gly Ser Gly Gly Gly Ser Ser Pro Gly Gln
225                 230                 235                 240

Gly Thr Gln Ser Glu Asn Ser Cys Thr His Phe Pro Gly Asn Leu Pro
                245                 250                 255

Asn Met Leu Arg Asp Leu Arg Asp Ala Phe Ser Arg Val Lys Thr Phe
            260                 265                 270

Phe Gln Met Lys Asp Gln Leu Asp Asn Leu Leu Leu Lys Glu Ser Leu
        275                 280                 285

Leu Glu Asp Phe Lys Gly Tyr Leu Gly Cys Gln Ala Leu Ser Glu Met
    290                 295                 300

Ile Gln Phe Tyr Leu Glu Glu Val Met Pro Gln Ala Glu Asn Gln Asp
305                 310                 315                 320

Pro Asp Ile Lys Ala His Val Asn Ser Leu Gly Glu Asn Leu Lys Thr
                325                 330                 335

Leu Arg Leu Arg Leu Arg Arg Cys His Arg Phe Leu Pro Cys Glu Asn
            340                 345                 350

Gly Gly Gly Ser Gly Gly Lys Ser Lys Ala Val Glu Gln Val Lys Asn
        355                 360                 365

Ala Phe Asn Lys Leu Gln Glu Lys Gly Ile Tyr Lys Ala Met Ser Glu
    370                 375                 380

Phe Asp Ile Phe Ile Asn Tyr Ile Glu Ala Tyr Met Thr Met Lys Ile
385                 390                 395                 400

Arg Asn Gly Gly Gly Gly Ser Gly Gly Gly Ser Gly Gly Gly Gly
                405                 410                 415

Ser Glu Val Gln Leu Leu Glu Ser Gly Gly Leu Val Gln Pro Gly
            420                 425                 430

Gly Ser Leu Arg Leu Ser Cys Ala Ala Ser Gly Phe Thr Phe Ser Ser
        435                 440                 445

Tyr Ala Met Ser Trp Val Arg Gln Ala Pro Gly Lys Gly Leu Glu Trp
    450                 455                 460

Val Ser Ala Ile Ser Gly Ser Gly Gly Ser Thr Tyr Tyr Ala Asp Ser
465                 470                 475                 480
```

| | | | | | | | | | | | |
|---|---|---|---|---|---|---|---|---|---|---|---|
|Val|Lys|Gly|Arg|Phe|Thr|Ile|Ser|Arg|Asp|Asn|Ser|Lys|Asn|Thr|Leu|
| | | | |485| | | |490| | | |495| | | |

Tyr Leu Gln Met Asn Ser Leu Arg Ala Glu Asp Thr Ala Val Tyr Tyr
            500                 505                 510

Cys Ala Lys Gly Trp Leu Gly Asn Phe Asp Tyr Trp Gly Gln Gly Thr
            515                 520                 525

Leu Val Thr Val Ser Ser Ala Ser Thr Lys Gly Pro Ser Val Phe Pro
        530                 535                 540

Leu Ala Pro Ser Ser Lys Ser Thr Ser Gly Gly Thr Ala Ala Leu Gly
545                 550                 555                 560

Cys Leu Val Lys Asp Tyr Phe Pro Glu Pro Val Thr Val Ser Trp Asn
                565                 570                 575

Ser Gly Ala Leu Thr Ser Gly Val His Thr Phe Pro Ala Val Leu Gln
            580                 585                 590

Ser Ser Gly Leu Tyr Ser Leu Ser Ser Val Val Thr Val Pro Ser Ser
        595                 600                 605

Ser Leu Gly Thr Gln Thr Tyr Ile Cys Asn Val Asn His Lys Pro Ser
    610                 615                 620

Asn Thr Lys Val Asp Lys Lys Val Glu Pro Lys Ser Cys Asp
625                 630                 635

<210> SEQ ID NO 24
<211> LENGTH: 1914
<212> TYPE: DNA
<213> ORGANISM: Artificial Sequence
<220> FEATURE:
<223> OTHER INFORMATION: 4G8 Fab -IL-10M1 - Fab (HC + IL-10M1 + HC)

<400> SEQUENCE: 24

```
gaggtgcaat gttggagtc tgggggaggc ttggtacagc ctgggggtc cctgagactc      60
tcctgtgcag cctccggatt cacctttagc agttatgcca tgagctgggt ccgccaggct    120
ccagggaagg gctggagtg gtctcagct attagtggta gtggtggtag cacatactac     180
gcagactccg tgaagggccg gttcaccatc tccagagaca attccaagaa cacgctgtat    240
ctgcagatga acagcctgag agccgaggac acggccgtat attactgtgc gaaagggtgg    300
ctgggtaatt ttgactactg gggccaagga accctggtca ccgtctcgag tgctagcacc    360
aagggcccca gcgtgtttcc tctggccccc agcagcaaga gcacaagcgg cggaacagcc    420
gccctgggct gcctggtgaa ggactacttc cccgagcccg tgaccgtgtc ttggaacagc    480
ggagccctga ccagcggcgt gcacaccttt cagccgtgc tgcagagcag cggcctgtac    540
agcctgagca gcgtggtgac cgtgcctagc agcagcctgg gcacccagac ctacatctgc    600
aacgtgaacc acaagcccag caacaccaag gtggacaaga aggtggagcc caagagctgt    660
gatggcggcg gaggctccgg aggcggagga agtggcggag cggcagcag cccaggccag    720
ggcacccagt ctgagaacag ctgcacccac ttcccaggca acctgcctaa catgcttcga    780
gatctccgag atgccttcag cagagtgaag actttctttc aaatgaagga tcagctggac    840
aacttgttgt taaaggagtc cttgctggag gactttaagg gttacctggg ttgccaagcc    900
ttgtctgaga tgatccagtt ttacctggag gaggtgatgc ccaagctga aaccaagac     960
ccagacatca aggcgcatgt gaactccctg ggggagaacc tgaagaccct caggctgagg    1020
ctacggcgct gtcatcgatt tcttcccctgt gaaaacggcg gaggctctgg aggcaagagc    1080
aaggccgtgg agcaggtgaa gaacgccttt aataagctcc aagagaaagg catctacaaa    1140
gccatgagtg agtttgacat cttcatcaac tacatagaag cttacatgac aatgaagata    1200
```
cgaaacggcg gcggaggctc cggtggcgga ggaagtggcg gaggaggatc cgaggtgcaa   1260
ttgttggagt ctgggggagg cttggtacag cctgggggt ccctgagact ctcctgtgca   1320
gcctccggat tcacctttag cagttatgcc atgagctggg tccgccaggc tccagggaag   1380
gggctggagt gggtctcagc tattagtggt agtggtggta gcacatacta cgcagactcc   1440
gtgaagggcc ggttcaccat ctccagagac aattccaaga acacgctgta tctgcagatg   1500
aacagcctga gagccgagga cacggccgta tattactgtg cgaaagggtg gctgggtaat   1560
tttgactact ggggccaagg aaccctggtc accgtctcga gtgctagcac caagggccca   1620
tcggtcttcc ccctggcacc ctcctccaag agcacctctg gggcacagc ggccctgggc   1680 tgcctggtca aggactactt ccccgaaccg gtgacggtgt cgtggaactc aggcgccctg   1740
accagcggcg tgcacacctt cccggctgtc ctacagtcct caggactcta ctccctcagc   1800
agcgtggtga ccgtgccctc agcagcttg ggcacccaga cctacatctg caacgtgaat   1860
cacaagccca gcaacaccaa ggtggataag aaagttgagc ccaaatcttg tgac         1914

<210> SEQ ID NO 25
<211> LENGTH: 215
<212> TYPE: PRT
<213> ORGANISM: Artificial Sequence
<220> FEATURE:
<223> OTHER INFORMATION: 4B9 IgG - IL-10 (LC)

<400> SEQUENCE: 25

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 26

<211> LENGTH: 645
<212> TYPE: DNA
<213> ORGANISM: Artificial Sequence
<220> FEATURE:
<223> OTHER INFORMATION: 4B9 IgG - IL-10 (LC)

<400> SEQUENCE: 26

```
gagatcgtgc tgacccagtc ccccggcacc ctgtctctga gccctggcga gagagccacc        60
ctgtcctgca gagcctccca gtccgtgacc tcctcctacc tcgcctggta tcagcagaag       120
cccggccagg cccctcggct gctgatcaac gtgggcagtc ggagagccac cggcatccct       180
gaccggttct ccggctctgg ctccggcacc gacttcaccc tgaccatctc ccggctggaa       240
cccgaggact tcgccgtgta ctactgccag cagggcatca tgctgccccc cacctttggc       300
cagggcacca aggtggaaat caagcgtacg gtggccgctc cctccgtgtt catcttccca       360
ccctccgacg agcagctgaa gtccggcacc gcctccgtcg tgtgcctgct gaacaacttc       420
taccccccgcg aggccaaggt gcagtggaag gtggacaacg ccctgcagtc cggcaactcc       480
caggaatccg tcaccgagca ggactccaag gacagcacct actccctgtc ctccaccctg       540
accctgtcca aggccgacta cgagaagcac aaggtgtacg cctgcgaagt gacccaccag       600
ggcctgtcca gccccgtgac caagtccttc aaccggggcg agtgc                       645
```

<210> SEQ ID NO 27
<211> LENGTH: 626
<212> TYPE: PRT
<213> ORGANISM: Artificial Sequence
<220> FEATURE:
<223> OTHER INFORMATION: 4B9 IgG - IL-10 (HC P329G LALA + IL-10)

<400> SEQUENCE: 27

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Gly Ser Gly Ala Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205
```

```
Thr Lys Val Asp Lys Lys Val Glu Pro Lys Ser Cys Asp Lys Thr His
    210             215                 220
Thr Cys Pro Pro Cys Pro Ala Pro Glu Ala Ala Gly Gly Pro Ser Val
225             230                 235                 240
Phe Leu Phe Pro Pro Lys Pro Lys Asp Thr Leu Met Ile Ser Arg Thr
            245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
        275                 280                 285
Thr Lys Pro Arg Glu Glu Gln Tyr Asn Ser Thr Tyr Arg Val Val Ser
290                 295                 300
Val Leu Thr Val Leu His Gln Asp Trp Leu Asn Gly Lys Glu Tyr Lys
305             310                 315                 320
Cys Lys Val Ser Asn Lys Ala Leu Gly Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Asp Glu Leu Thr Lys Asn Gln Val Ser Leu Thr Cys Leu
        355                 360                 365
Val Lys Gly Phe Tyr Pro Ser Asp Ile Ala Val Glu Trp Glu Ser Asn
370             375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Gly Gly
        435                 440                 445
Gly Gly Ser Gly Gly Gly Ser Gly Gly Gly Ser Gly Gly Gly
450                 455                 460
Gly Ser Ser Pro Gly Gln Gly Thr Gln Ser Glu Asn Ser Cys Thr His
465                 470                 475                 480
Phe Pro Gly Asn Leu Pro Asn Met Leu Arg Asp Leu Arg Asp Ala Phe
                485                 490                 495
Ser Arg Val Lys Thr Phe Phe Gln Met Lys Asp Gln Leu Asp Asn Leu
            500                 505                 510
Leu Leu Lys Glu Ser Leu Leu Glu Asp Phe Lys Gly Tyr Leu Gly Cys
        515                 520                 525
Gln Ala Leu Ser Glu Met Ile Gln Phe Tyr Leu Glu Glu Val Met Pro
530             535                 540
Gln Ala Glu Asn Gln Asp Pro Asp Ile Lys Ala His Val Asn Ser Leu
545                 550                 555                 560
Gly Glu Asn Leu Lys Thr Leu Arg Leu Arg Leu Arg Arg Cys His Arg
                565                 570                 575
Phe Leu Pro Cys Glu Asn Lys Ser Lys Ala Val Glu Gln Val Lys Asn
            580                 585                 590
Ala Phe Asn Lys Leu Gln Glu Lys Gly Ile Tyr Lys Ala Met Ser Glu
        595                 600                 605
Phe Asp Ile Phe Ile Asn Tyr Ile Glu Ala Tyr Met Thr Met Lys Ile
610             615                 620

Arg Asn
```

<210> SEQ ID NO 28
<211> LENGTH: 1878
<212> TYPE: DNA
<213> ORGANISM: Artificial Sequence
<220> FEATURE:
<223> OTHER INFORMATION: 4B9 IgG - IL-10 (HC P329G LALA + IL-10)

<400> SEQUENCE: 28

```
gaggtgcagc tgctcgaaag cggcggagga ctggtgcagc ctggcggcag cctgagactg      60
tcttgcgccg ccagcggctt caccttcagc agctacgcca tgagctgggt ccgccaggcc     120
cctggcaagg gactggaatg ggtgtccgcc atcatcggct ctggcgccag cacctactac     180
gccgacagcg tgaagggccg gttcaccatc agccgggaca acagcaagaa caccctgtac     240
ctgcagatga acagcctgcg ggccgaggac accgccgtgt actactgcgc aagggatgg     300
ttcggcggct tcaactactg gggacagggc accctggtca cagtgtccag cgctagcacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga agttgagcc caaatcttgt     660
gacaaaactc acacatgccc accgtgccca gcacctgaag ctgcagggg accgtcagtc     720
ttcctcttcc cccaaaaccc aaggacaccc ctcatgatct cccggacccc tgaggtcaca     780
tgcgtggtgg tggacgtgag ccacgaagac cctgaggtca agttcaactg gtacgtggac     840
ggcgtggagg tgcataatgc caagacaaag ccgcgggagg agcagtacaa cagcacgtac     900
cgtgtggtca gcgtcctcac cgtcctgcac caggactggc tgaatggcaa ggagtacaag     960
tgcaaggtct ccaacaaagc cctcggcgcc cccatcgaga aaaccatctc caaagccaaa    1020
gggcagcccc gagaaccaca ggtgtacacc ctgcccccat cccgggatga gctgaccaag    1080
aaccaggtca gcctgacctg cctggtcaaa ggcttctatc ccagcgacat cgccgtggag    1140
tgggagagca atgggcagcc ggagaacaac tacaagacca cgcctcccgt gctggactcc    1200
gacggctcct tcttcctcta cagcaagctc accgtggaca agagcaggtg gcagcagggg    1260
aacgtcttct catgctccgt gatgcatgag gctctgcaca accactacac gcagaagagc    1320
ctctccctgt ctccgggtgg cggaggggga tctggaggtg cggctccgg aggcggagga    1380
tctgggggag gcggaagtag cccgggccag ggcacccaga gcgagaacag ctgcacccac    1440
ttccccggca acctgcccaa catgctgcgg gacctgaggg acgccttcag cagagtgaaa    1500
accttcttcc agatgaagga ccagctggac aacctgctgc tgaaagagag cctgctggaa    1560
gatttcaagg gctacctggg ctgtcaggcc ctgagcgaga tgatccagtt ctacctggaa    1620
gaagtgatgc cccaggccga gaaccaggac cccgacatca aggcccacgt gaacagcctg    1680
ggcgagaacc tgaaaaccct gcggctgaga ctgcggcggt gccacagatt tctgccctgc    1740
gagaacaaga gcaaggccgt ggaacaggtg aagaacgcct tcaacaagct gcaggaaaag    1800
ggcatctaca aggccatgtc cgagttcgac atcttcatca actacatcga agcttacatg    1860
acaatgaaaa tccgcaat                                                 1878
```

<210> SEQ ID NO 29
<211> LENGTH: 627

<212> TYPE: PRT
<213> ORGANISM: Artificial Sequence
<220> FEATURE:
<223> OTHER INFORMATION: 4B9 IgG-(IL-10M1)2 (HC P329G LALA + IL-10M1)

<400> SEQUENCE: 29

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Gly Ser Gly Ala Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Gly Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380
```

Gly Gln Pro Glu Asn Asn Tyr Lys Thr Thr Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Gly Gly
        435                 440                 445

Gly Gly Ser Gly Gly Gly Ser Gly Gly Gly Ser Ser Pro Gly
    450                 455                 460

Gln Gly Thr Gln Ser Glu Asn Ser Cys Thr His Phe Pro Gly Asn Leu
465                 470                 475                 480

Pro Asn Met Leu Arg Asp Leu Arg Asp Ala Phe Ser Arg Val Lys Thr
            485                 490                 495

Phe Phe Gln Met Lys Asp Gln Leu Asp Asn Leu Leu Leu Lys Glu Ser
            500                 505                 510

Leu Leu Glu Asp Phe Lys Gly Tyr Leu Gly Cys Gln Ala Leu Ser Glu
        515                 520                 525

Met Ile Gln Phe Tyr Leu Glu Glu Val Met Pro Gln Ala Glu Asn Gln
530                 535                 540

Asp Pro Asp Ile Lys Ala His Val Asn Ser Leu Gly Glu Asn Leu Lys
545                 550                 555                 560

Thr Leu Arg Leu Arg Leu Arg Arg Cys His Arg Phe Leu Pro Cys Glu
            565                 570                 575

Asn Gly Gly Gly Ser Gly Gly Lys Ser Lys Ala Val Glu Gln Val Lys
            580                 585                 590

Asn Ala Phe Asn Lys Leu Gln Glu Lys Gly Ile Tyr Lys Ala Met Ser
        595                 600                 605

Glu Phe Asp Ile Phe Ile Asn Tyr Ile Glu Ala Tyr Met Thr Met Lys
    610                 615                 620

Ile Arg Asn
625

<210> SEQ ID NO 30
<211> LENGTH: 1881
<212> TYPE: DNA
<213> ORGANISM: Artificial Sequence
<220> FEATURE:
<223> OTHER INFORMATION: 4B9 IgG -(IL-10M1)2 (HC P329G LALA + IL-10M1)

<400> SEQUENCE: 30
gaggtgcagc tgctcgaaag cggcggagga ctggtgcagc ctggcggcag cctgagactg      60
tcttgcgccg ccagcggctt caccttcagc agctacgcca tgagctgggt ccgccaggcc     120
cctggcaagg gactggaatg ggtgtccgcc atcatcggct ctggcgccag cacctactac     180
gccgacagcg tgaagggccg gttcaccatc agcagggaca acagcaagaa caccctgtac     240
ctgcagatga acagcctgcg ggccgaggac accgccgtgt actactgcgc aagggatgg     300 ttcggcggct tcaactactg gggacagggc accctggtca cagtgtccag cgctagcacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga agttgagcc caaatcttgt     660

```
gacaaaactc acacatgccc accgtgccca gcacctgaag ctgcaggggg accgtcagtc    720
ttcctcttcc ccccaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgtgtggtca gcgtcctcac cgtcctgcac caggactggc tgaatggcaa ggagtacaag    960
tgcaaggtct ccaacaaagc cctcggcgcc cccatcgaga aaaccatctc caaagccaaa   1020
gggcagcccc gagaaccaca ggtgtacacc ctgcccccat cccgggatga gctgaccaag   1080
aaccaggtca gcctgacctg cctggtcaaa ggcttctatc ccagcgacat cgccgtggag   1140
tgggagagca atgggcagcc ggagaacaac tacaagacca cgcctcccgt gctggactcc   1200
gacggctcct tcttcctcta cagcaagctc accgtggaca agagcaggtg gcagcagggg   1260
aacgtcttct catgctccgt gatgcatgag gctctgcaca accactacac gcagaagagc   1320
ctctccctgt ctccgggtgg cggcggaggc tccggaggcg gaggaagtgg cggcggtggc   1380
agctctccag gccagggcac ccagagcgag aacagctgca cccacttccc cggcaacctg   1440
cccaacatgc tgcgggacct gagggacgcc ttcagcagag tgaaaacctt cttccagatg   1500
aaggaccagc tggacaacct gctgctgaaa gagagcctgc tggaagattt caagggctac   1560
ctgggctgtc aggccctgag cgagatgatc cagttctacc tggaagaagt gatgccccag   1620
gccgagaacc aggaccccga catcaaggcc cacgtgaaca gcctgggcga aacctgaaa    1680 accctgcggc tgagactgcg gcggtgccac agatttctgc cctgcgagaa cggcggaggc   1740
tctggcggaa agtccaaggc cgtggaacag gtgaagaacg ccttcaacaa gctgcaggaa   1800
aagggcatct acaaggccat gagcgagttc gacatcttca tcaactacat cgaagcttac   1860
atgacaatga agatacgaaa c                                              1881
```

<210> SEQ ID NO 31
<211> LENGTH: 396
<212> TYPE: PRT
<213> ORGANISM: Artificial Sequence
<220> FEATURE:
<223> OTHER INFORMATION: 4B9 Fab - IL-10 (HC + IL-10)

<400> SEQUENCE: 31

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Gly Ser Gly Ala Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140
```

```
Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Gly Gly Gly
    210                 215                 220

Gly Ser Gly Gly Gly Ser Gly Gly Gly Ser Ser Pro Gly Gln
225                 230                 235                 240

Gly Thr Gln Ser Glu Asn Ser Cys Thr His Phe Pro Gly Asn Leu Pro
                245                 250                 255

Asn Met Leu Arg Asp Leu Arg Asp Ala Phe Ser Arg Val Lys Thr Phe
            260                 265                 270

Phe Gln Met Lys Asp Gln Leu Asp Asn Leu Leu Leu Lys Glu Ser Leu
        275                 280                 285

Leu Glu Asp Phe Lys Gly Tyr Leu Gly Cys Gln Ala Leu Ser Glu Met
    290                 295                 300

Ile Gln Phe Tyr Leu Glu Glu Val Met Pro Gln Ala Glu Asn Gln Asp
305                 310                 315                 320

Pro Asp Ile Lys Ala His Val Asn Ser Leu Gly Glu Asn Leu Lys Thr
                325                 330                 335

Leu Arg Leu Arg Leu Arg Arg Cys His Arg Phe Leu Pro Cys Glu Asn
            340                 345                 350

Lys Ser Lys Ala Val Glu Gln Val Lys Asn Ala Phe Asn Lys Leu Gln
        355                 360                 365

Glu Lys Gly Ile Tyr Lys Ala Met Ser Glu Phe Asp Ile Phe Ile Asn
    370                 375                 380

Tyr Ile Glu Ala Tyr Met Thr Met Lys Ile Arg Asn
385                 390                 395

<210> SEQ ID NO 32
<211> LENGTH: 1188
<212> TYPE: DNA
<213> ORGANISM: Artificial Sequence
<220> FEATURE:
<223> OTHER INFORMATION: 4B9 Fab - IL-10 (HC + IL-10)

<400> SEQUENCE: 32
gaggtgcagc tgctcgaaag cggcggagga ctggtgcagc ctggcggcag cctgagactg      60
tcttgcgccg ccagcggctt caccttcagc agctacgcca tgagctgggt ccgccaggcc     120
cctggcaagg gactggaatg ggtgtccgcc atcatcggct ctggcgccag cacctactac     180
gccgacagcg tgaagggccg gttcaccatc agcagggaca acagcaagaa caccctgtac     240
ctgcagatga acagcctgcg cgccgaggac accgccgtgt actactgcgc caagggatgg     300
ttcggcggct tcaactactg gggacagggc accctggtca cagtgtccag cgctagcacc     360
aagggcccca gcgtgtttcc tctggccccc agcagcaaga gcacaagcgg cggaacagcc     420
gccctgggct gcctggtgaa ggactacttc cccgagcccg tgaccgtgtc ttggaacagc     480
ggagccctga ccagcggcgt gcacaccttt ccagccgtgc tgcagagcag cggcctgtac     540
agcctgagca gcgtggtgac cgtgcctagc agcagcctgg gcacccagac ctacatctgc     600
```

```
aacgtgaacc acaagcccag caacaccaag gtggacaaga aggtggagcc caagagctgt    660
gatggcggcg gaggctccgg aggcggagga tctgggggag gcggaagtag cccgggccag    720
ggcacccaga gcgagaacag ctgcacccac ttccccggca acctgcccaa catgctgcgg    780
gacctgaggg acgccttcag cagagtgaaa accttcttcc agatgaagga ccagctggac    840
aacctgctgc tgaaagagag cctgctggaa gatttcaagg gctacctggg ctgtcaggcc    900
ctgagcgaga tgatccagtt ctacctggaa gaagtgatgc cccaggccga gaaccaggac    960
cccgacatca aggcccacgt gaacagcctg ggcgagaacc tgaaaaccct gcggctgaga   1020
ctgcggcggt gccacagatt tctgcccctgc gagaacaaga gcaaggccgt ggaacaggtg   1080
aagaacgcct tcaacaagct gcaggaaaag ggcatctaca aggccatgtc cgagttcgac   1140
atcttcatca actacatcga agcttacatg acaatgaaaa tccgcaat              1188
```

<210> SEQ ID NO 33
<211> LENGTH: 812
<212> TYPE: PRT
<213> ORGANISM: Artificial Sequence
<220> FEATURE:
<223> OTHER INFORMATION: 4B9 Fab - scIL-10 - Fab (HC + IL-10 + HC)

<400> SEQUENCE: 33

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Gly Ser Gly Ala Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Gly Gly Gly
    210                 215                 220

Gly Ser Gly Gly Gly Gly Ser Gly Gly Gly Ser Ser Pro Gly Gln
225                 230                 235                 240

Gly Thr Gln Ser Glu Asn Ser Cys Thr His Phe Pro Gly Asn Leu Pro
                245                 250                 255

Asn Met Leu Arg Asp Leu Arg Asp Ala Phe Ser Arg Val Lys Thr Phe
```

```
              260                 265                 270
Phe Gln Met Lys Asp Gln Leu Asp Asn Leu Leu Lys Glu Ser Leu
            275                 280                 285
Leu Glu Asp Phe Lys Gly Tyr Leu Gly Cys Gln Ala Leu Ser Glu Met
        290                 295                 300
Ile Gln Phe Tyr Leu Glu Glu Val Met Pro Gln Ala Glu Asn Gln Asp
305                 310                 315                 320
Pro Asp Ile Lys Ala His Val Asn Ser Leu Gly Glu Asn Leu Lys Thr
                325                 330                 335
Leu Arg Leu Arg Leu Arg Arg Cys His Arg Phe Leu Pro Cys Glu Asn
            340                 345                 350
Lys Ser Lys Ala Val Glu Gln Val Lys Asn Ala Phe Asn Lys Leu Gln
        355                 360                 365
Glu Lys Gly Ile Tyr Lys Ala Met Ser Glu Phe Asp Ile Phe Ile Asn
        370                 375                 380
Tyr Ile Glu Ala Tyr Met Thr Met Lys Ile Arg Asn Gly Gly Gly
385                 390                 395                 400
Ser Gly Gly Gly Gly Ser Gly Gly Gly Gly Ser Gly Gly Gly Ser
                405                 410                 415
Ser Pro Gly Gln Gly Thr Gln Ser Glu Asn Ser Cys Thr His Phe Pro
            420                 425                 430
Gly Asn Leu Pro Asn Met Leu Arg Asp Leu Arg Asp Ala Phe Ser Arg
        435                 440                 445
Val Lys Thr Phe Phe Gln Met Lys Asp Gln Leu Asp Asn Leu Leu Leu
    450                 455                 460
Lys Glu Ser Leu Leu Glu Asp Phe Lys Gly Tyr Leu Gly Cys Gln Ala
465                 470                 475                 480
Leu Ser Glu Met Ile Gln Phe Tyr Leu Glu Glu Val Met Pro Gln Ala
                485                 490                 495
Glu Asn Gln Asp Pro Asp Ile Lys Ala His Val Asn Ser Leu Gly Glu
            500                 505                 510
Asn Leu Lys Thr Leu Arg Leu Arg Leu Arg Arg Cys His Arg Phe Leu
        515                 520                 525
Pro Cys Glu Asn Lys Ser Lys Ala Val Glu Gln Val Lys Asn Ala Phe
    530                 535                 540
Asn Lys Leu Gln Glu Lys Gly Ile Tyr Lys Ala Met Ser Glu Phe Asp
545                 550                 555                 560
Ile Phe Ile Asn Tyr Ile Glu Ala Tyr Met Thr Met Lys Ile Arg Asn
                565                 570                 575
Gly Gly Gly Gly Ser Gly Gly Gly Ser Gly Gly Gly Gly Ser Glu
            580                 585                 590
Val Gln Leu Leu Glu Ser Gly Gly Gly Leu Val Gln Pro Gly Gly Ser
        595                 600                 605
Leu Arg Leu Ser Cys Ala Ala Ser Gly Phe Thr Phe Ser Ser Tyr Ala
    610                 615                 620
Met Ser Trp Val Arg Gln Ala Pro Gly Lys Gly Leu Glu Trp Val Ser
625                 630                 635                 640
Ala Ile Ile Gly Ser Gly Ala Ser Thr Tyr Tyr Ala Asp Ser Val Lys
                645                 650                 655
Gly Arg Phe Thr Ile Ser Arg Asp Asn Ser Lys Asn Thr Leu Tyr Leu
            660                 665                 670
Gln Met Asn Ser Leu Arg Ala Glu Asp Thr Ala Val Tyr Tyr Cys Ala
        675                 680                 685
```

```
Lys Gly Trp Phe Gly Gly Phe Asn Tyr Trp Gly Gln Gly Thr Leu Val
            690                 695                 700

Thr Val Ser Ser Ala Ser Thr Lys Gly Pro Ser Val Phe Pro Leu Ala
705                 710                 715                 720

Pro Ser Ser Lys Ser Thr Ser Gly Gly Thr Ala Ala Leu Gly Cys Leu
                725                 730                 735

Val Lys Asp Tyr Phe Pro Glu Pro Val Thr Val Ser Trp Asn Ser Gly
            740                 745                 750

Ala Leu Thr Ser Gly Val His Thr Phe Pro Ala Val Leu Gln Ser Ser
        755                 760                 765

Gly Leu Tyr Ser Leu Ser Ser Val Val Thr Val Pro Ser Ser Ser Leu
770                 775                 780

Gly Thr Gln Thr Tyr Ile Cys Asn Val Asn His Lys Pro Ser Asn Thr
785                 790                 795                 800

Lys Val Asp Lys Lys Val Glu Pro Lys Ser Cys Asp
            805                 810
```

<210> SEQ ID NO 34
<211> LENGTH: 2436
<212> TYPE: DNA
<213> ORGANISM: Artificial Sequence
<220> FEATURE:
<223> OTHER INFORMATION: 4B9 Fab - scIL-10 - Fab (HC + IL-10 + HC)

<400> SEQUENCE: 34

```
gaggtgcagc tgctcgaaag cggcggagga ctggtgcagc ctggcggcag cctgagactg      60
tcttgcgccg ccagcggctt caccttcagc agctacgcca tgagctgggt ccgccaggcc     120
cctggcaagg gactggaatg ggtgtccgcc atcatcggct ctggcgccag cacctactac     180
gccgacagcg tgaagggccg gttcaccatc agccgggaca cagcaagaa caccctgtac     240 ctgcagatga acagcctgcg ggccgaggac accgccgtgt actactgcgc caagggatgg     300
ttcggcggct tcaactactg gggacagggc accctggtca cagtgtccag cgctagcacc     360
aagggcccca gcgtgtttcc tctggccccc agcagcaaga gcacaagcgg cggaacagcc     420
gccctgggct gcctggtgaa ggactactte cccgagcccg tgaccgtgtc ttggaacagc     480
ggagccctga ccagcggcgt gcacaccttt ccagccgtgc tgcagagcag cggcctgtac     540
agcctgagca gcgtggtgac cgtgcctagc agcagcctgg gcacccagac ctacatctgc     600
aacgtgaacc acaagcccag caacaccaag gtggacaaga aggtggagcc caagagctgt     660
gatggcggcg aggctcccgg aggcggagga tctggggag gcggaagtag cccgggccag     720
ggcacccaga gcgagaacag ctgcacccac ttccccggca acctgcccaa catgctgcgg     780
gacctgaggg acgccttcag cagagtgaaa accttcttcc agatgaagga ccagctggac     840
aacctgctgc tgaaagagag cctgctggaa gatttcaagg gctacctggg ctgtcaggcc     900
ctgagcgaga tgatccagtt ctacctggaa gaagtgatgc cccaggccga gaaccaggac     960
cccgacatca aggcccacgt gaacagcctg ggcgagaacc tgaaaacccc tgcggctgaga    1020 ctgcggcggt gccacagatt tctgccctgc gagaacaaga gcaaggccgt ggaacaggtg    1080
aagaacgcct tcaacaagct gcaggaaaag ggcatctaca aggccatgtc cgagttcgac    1140
atcttcatca actacatcga agcttacatg accatgaaga tcagaaacgg cggaggcgga    1200
tctggcggcg gtgaagtgg aggcggagga tctgggggag gcggaagtag cccgggccag    1260
ggcacccaga gcgagaacag ctgcacccac ttccccggca acctgcccaa catgctgcgg    1320
```

```
gacctgaggg acgccttcag cagagtgaaa accttcttcc agatgaagga ccagctggac    1380
aacctgctgc tgaaagagag cctgctggaa gatttcaagg ctacctgggc ctgtcaggcc    1440
ctgagcgaga tgatccagtt ctacctggaa gaagtgatgc cccaggccga gaaccaggac    1500
cccgacatca aggcccacgt gaacagcctg ggcgagaacc tgaaaaccct gcggctgaga    1560
ctgcggcggt gccacagatt tctgccctgc gagaacaaga gcaaggccgt ggaacaggtg    1620
aagaacgcct tcaacaagct gcaggaaaag ggcatctaca aggccatgtc cgagttcgac    1680
atcttcatca actacatcga ggcctacatg acaatgaaaa tccgcaatgg cggggaggga    1740
tcaggtggag ggggcagcgg tggtggagga tccgaggtgc aattgctcga agcggcgga    1800 ggactggtgc agcctggcgg cagcctgaga ctgtcttgcg ccgccagcgg tttcaccttc    1860
agcagctacg ccatgagctg gtccgccag gcccctggca agggactgga atgggtgtcc    1920
gccatcatcg gctctggcgc cagcacctac tacgccgaca gcgtgaaggg ccggttcacc    1980
atcagccggg acaacagcaa gaacaccctg tacctgcaga tgaacagcct gcgggccgag    2040
gacaccgccg tgtactactg cgccaaggga tggttcggcg gcttcaacta ctggggacag    2100
ggcaccctgg tcacagtgtc cagcgctagc accaagggcc catcggtctt ccccctggca    2160
ccctcctcca agagcacctc tggggggcaca gcggccctgg gctgcctggt caaggactac    2220
ttccccgaac cggtgacggt gtcgtggaac tcaggcgccc tgaccagcgg cgtgcacacc    2280
ttcccggctg tcctacagtc ctcaggactc tactccctca gcagcgtggt gaccgtgccc    2340
tccagcagct gggcacccca gacctacatc tgcaacgtga atcacaagcc cagcaacacc    2400
aaggtggata gaaagttga gcccaaatct tgtgac                               2436
```

<210> SEQ ID NO 35
<211> LENGTH: 19
<212> TYPE: PRT
<213> ORGANISM: Artificial Sequence
<220> FEATURE:
<223> OTHER INFORMATION: Leader peptide

<400> SEQUENCE: 35

Met Gly Trp Ser Cys Ile Ile Leu Phe Leu Val Ala Thr Ala Thr Gly
1               5                   10                  15

Val His Ser

<210> SEQ ID NO 36
<211> LENGTH: 57
<212> TYPE: DNA
<213> ORGANISM: Artificial Sequence
<220> FEATURE:
<223> OTHER INFORMATION: Leader peptide

<400> SEQUENCE: 36
atgggctggt cctgcatcat cctgtttctg gtcgccacag ccaccggcgt gcactct        57

<210> SEQ ID NO 37
<211> LENGTH: 5
<212> TYPE: PRT
<213> ORGANISM: Artificial Sequence
<220> FEATURE:
<223> OTHER INFORMATION: HCDR1 (1)

<400> SEQUENCE: 37

Ser Tyr Ala Met Ser
1               5

```
<210> SEQ ID NO 38
<211> LENGTH: 15
<212> TYPE: DNA
<213> ORGANISM: Artificial Sequence
<220> FEATURE:
<223> OTHER INFORMATION: HCDR1 (1)

<400> SEQUENCE: 38
agttatgcca tgagc                                                      15

<210> SEQ ID NO 39
<211> LENGTH: 5
<212> TYPE: PRT
<213> ORGANISM: Artificial Sequence
<220> FEATURE:
<223> OTHER INFORMATION: HCDR1 (2)

<400> SEQUENCE: 39

Ser His Ala Met Ser
1               5

<210> SEQ ID NO 40
<211> LENGTH: 15
<212> TYPE: DNA
<213> ORGANISM: Artificial Sequence
<220> FEATURE:
<223> OTHER INFORMATION: HCDR1 (2)

<400> SEQUENCE: 40
agtcatgcta tgagc                                                      15

<210> SEQ ID NO 41
<211> LENGTH: 16
<212> TYPE: PRT
<213> ORGANISM: Artificial Sequence
<220> FEATURE:
<223> OTHER INFORMATION: HCDR2 (1)

<400> SEQUENCE: 41

Ala Ile Ser Gly Ser Gly Gly Ser Thr Tyr Tyr Ala Asp Ser Val Lys
1               5                   10                  15

<210> SEQ ID NO 42
<211> LENGTH: 48
<212> TYPE: DNA
<213> ORGANISM: Artificial Sequence
<220> FEATURE:
<223> OTHER INFORMATION: HCDR2 (1)

<400> SEQUENCE: 42
gctattagtg gtagtggtgg tagcacatac tacgcagact ccgtgaag                  48

<210> SEQ ID NO 43
<211> LENGTH: 16
<212> TYPE: PRT
<213> ORGANISM: Artificial Sequence
<220> FEATURE:
<223> OTHER INFORMATION: HCDR2 (2)

<400> SEQUENCE: 43

Ala Ile Ile Gly Ser Gly Ala Ser Thr Tyr Tyr Ala Asp Ser Val Lys
1               5                   10                  15

<210> SEQ ID NO 44
<211> LENGTH: 48
<212> TYPE: DNA
<213> ORGANISM: Artificial Sequence
```

<220> FEATURE:
<223> OTHER INFORMATION: HCDR2 (2)

<400> SEQUENCE: 44
gccatcatcg gctctggcgc cagcacctac tacgccgaca gcgtgaag                48

<210> SEQ ID NO 45
<211> LENGTH: 15
<212> TYPE: PRT
<213> ORGANISM: Artificial Sequence
<220> FEATURE:
<223> OTHER INFORMATION: HCDR2 (3)

<400> SEQUENCE: 45

Ala Ile Trp Ala Ser Gly Glu Gln Tyr Tyr Ala Asp Ser Val Lys
1               5                   10                  15

<210> SEQ ID NO 46
<211> LENGTH: 45
<212> TYPE: DNA
<213> ORGANISM: Artificial Sequence
<220> FEATURE:
<223> OTHER INFORMATION: HCDR2 (3)

<400> SEQUENCE: 46
gctatttggg ctagtgggga gcaatactac gcagactccg tgaag                45

<210> SEQ ID NO 47
<211> LENGTH: 8
<212> TYPE: PRT
<213> ORGANISM: Artificial Sequence
<220> FEATURE:
<223> OTHER INFORMATION: HCDR3 (1)

<400> SEQUENCE: 47

Tyr Cys Ala Lys Gly Trp Phe Gly
1               5

<210> SEQ ID NO 48
<211> LENGTH: 24
<212> TYPE: DNA
<213> ORGANISM: Artificial Sequence
<220> FEATURE:
<223> OTHER INFORMATION: HCDR3 (1)

<400> SEQUENCE: 48
tactgcgcca agggatggtt cggc                24

<210> SEQ ID NO 49
<211> LENGTH: 8
<212> TYPE: PRT
<213> ORGANISM: Artificial Sequence
<220> FEATURE:
<223> OTHER INFORMATION: HCDR3 (2)

<400> SEQUENCE: 49

Tyr Cys Ala Lys Gly Trp Leu Gly
1               5

<210> SEQ ID NO 50
<211> LENGTH: 24
<212> TYPE: DNA
<213> ORGANISM: Artificial Sequence
<220> FEATURE:
<223> OTHER INFORMATION: HCDR3 (2)

<400> SEQUENCE: 50

```
tactgtgcga aagggtggct gggt                                          24
```

<210> SEQ ID NO 51
<211> LENGTH: 11
<212> TYPE: PRT
<213> ORGANISM: Artificial Sequence
<220> FEATURE:
<223> OTHER INFORMATION: LCDR1 (1)

<400> SEQUENCE: 51

Arg Ala Ser Gln Ser Val Thr Ser Ser Tyr Leu
1               5                   10

<210> SEQ ID NO 52
<211> LENGTH: 33
<212> TYPE: DNA
<213> ORGANISM: Artificial Sequence
<220> FEATURE:
<223> OTHER INFORMATION: LCDR1 (1)

<400> SEQUENCE: 52

```
agagcctccc agtccgtgac ctcctcctac ctc                                33
```

<210> SEQ ID NO 53
<211> LENGTH: 11
<212> TYPE: PRT
<213> ORGANISM: Artificial Sequence
<220> FEATURE:
<223> OTHER INFORMATION: LCDR1 (2)

<400> SEQUENCE: 53

Arg Ala Ser Gln Ser Val Ser Arg Ser Tyr Leu
1               5                   10

<210> SEQ ID NO 54
<211> LENGTH: 33
<212> TYPE: DNA
<213> ORGANISM: Artificial Sequence
<220> FEATURE:
<223> OTHER INFORMATION: LCDR1 (2)

<400> SEQUENCE: 54

```
agagcctccc agtccgtgtc ccggtcctac ctc                                33
```

<210> SEQ ID NO 55
<211> LENGTH: 7
<212> TYPE: PRT
<213> ORGANISM: Artificial Sequence
<220> FEATURE:
<223> OTHER INFORMATION: LCDR2 (1)

<400> SEQUENCE: 55

Asn Val Gly Ser Arg Arg Ala
1               5

<210> SEQ ID NO 56
<211> LENGTH: 21
<212> TYPE: DNA
<213> ORGANISM: Artificial Sequence
<220> FEATURE:
<223> OTHER INFORMATION: LCDR2 (1)

<400> SEQUENCE: 56

```
aacgtgggca gtcggagagc c                                             21
```

```
<210> SEQ ID NO 57
<211> LENGTH: 7
<212> TYPE: PRT
<213> ORGANISM: Artificial Sequence
<220> FEATURE:
<223> OTHER INFORMATION: LCDR2 (2)

<400> SEQUENCE: 57

Ile Gly Ala Ser Thr Arg Ala
1               5

<210> SEQ ID NO 58
<211> LENGTH: 21
<212> TYPE: DNA
<213> ORGANISM: Artificial Sequence
<220> FEATURE:
<223> OTHER INFORMATION: LCDR2 (2)

<400> SEQUENCE: 58
atcggcgcct ctaccagagc c                                              21

<210> SEQ ID NO 59
<211> LENGTH: 9
<212> TYPE: PRT
<213> ORGANISM: Artificial Sequence
<220> FEATURE:
<223> OTHER INFORMATION: LCDR3 (1)

<400> SEQUENCE: 59

Cys Gln Gln Gly Ile Met Leu Pro Pro
1               5

<210> SEQ ID NO 60
<211> LENGTH: 27
<212> TYPE: DNA
<213> ORGANISM: Artificial Sequence
<220> FEATURE:
<223> OTHER INFORMATION: LCDR3 (1)

<400> SEQUENCE: 60
tgccagcagg gcatcatgct gcccccc                                        27

<210> SEQ ID NO 61
<211> LENGTH: 9
<212> TYPE: PRT
<213> ORGANISM: Artificial Sequence
<220> FEATURE:
<223> OTHER INFORMATION: LCDR3 (2)

<400> SEQUENCE: 61

Cys Gln Gln Gly Gln Val Ile Pro Pro
1               5

<210> SEQ ID NO 62
<211> LENGTH: 27
<212> TYPE: DNA
<213> ORGANISM: Artificial Sequence
<220> FEATURE:
<223> OTHER INFORMATION: LCDR3 (2)

<400> SEQUENCE: 62
tgccagcagg gccaggtcat ccctccc                                        27

<210> SEQ ID NO 63
<211> LENGTH: 117
<212> TYPE: PRT
<213> ORGANISM: Artificial Sequence
```

<220> FEATURE:
<223> OTHER INFORMATION: 4G8; VH

<400> SEQUENCE: 63

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Leu Gly Asn Phe Asp Tyr Trp Gly Gln Gly Thr Leu
            100                 105                 110

Val Thr Val Ser Ser
        115

<210> SEQ ID NO 64
<211> LENGTH: 351
<212> TYPE: DNA
<213> ORGANISM: Artificial Sequence
<220> FEATURE:
<223> OTHER INFORMATION: 4G8; VH

<400> SEQUENCE: 64
gaggtgcaat tgttggagtc tgggggaggc ttggtacagc ctgggggtc cctgagactc      60 tcctgtgcag cctccggatt cacctttagc agttatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcagatga acagcctgag agccgaggac acggccgtat attactgtgc gaaagggtgg     300
ctgggtaatt ttgactactg gggccaagga accctggtca ccgtctcgag t             351

<210> SEQ ID NO 65
<211> LENGTH: 108
<212> TYPE: PRT
<213> ORGANISM: Artificial Sequence
<220> FEATURE:
<223> OTHER INFORMATION: 4G8; VL

<400> SEQUENCE: 65

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Ser
            20                  25                  30

Tyr Leu Ala Trp Tyr Gln Gln Lys Pro Gly Gln Ala Pro Arg Leu Leu
        35                  40                  45

Ile Ile Gly Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Val Ile Pro
                85                  90                  95

Pro Thr Phe Gly Gln Gly Thr Lys Val Glu Ile Lys
            100                 105

<210> SEQ ID NO 66
<211> LENGTH: 324
<212> TYPE: DNA
<213> ORGANISM: Artificial Sequence
<220> FEATURE:
<223> OTHER INFORMATION: 4G8; VL

<400> SEQUENCE: 66
gagatcgtgc tgacccagtc ccccggcacc ctgtctctga gccctggcga gagagccacc    60
ctgtcctgca gagcctccca gtccgtgtcc cggtcctacc tcgcctggta tcagcagaag   120
cccggccagg cccctcggct gctgatcatc ggcgcctcta ccagagccac cggcatccct   180
gaccggttct ccggctctgg ctccggcacc gacttcaccc tgaccatctc ccggctggaa   240
cccgaggact tcgccgtgta ctactgccag cagggccagg tcatccctcc cacctttggc   300
cagggcacca aggtggaaat caag                                          324

<210> SEQ ID NO 67
<211> LENGTH: 117
<212> TYPE: PRT
<213> ORGANISM: Artificial Sequence
<220> FEATURE:
<223> OTHER INFORMATION: 4B9; VH

<400> SEQUENCE: 67

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Gly Ser Gly Ala Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
        115

<210> SEQ ID NO 68
<211> LENGTH: 351
<212> TYPE: DNA
<213> ORGANISM: Artificial Sequence
<220> FEATURE:
<223> OTHER INFORMATION: 4B9; VH

<400> SEQUENCE: 68
gaggtgcagc tgctcgaaag cggcggagga ctggtgcagc ctggcggcag cctgagactg    60
tcttgcgccg ccagcggctt caccttcagc agctacgcca tgagctgggt ccgccaggcc   120
cctggcaagg gactggaatg ggtgtccgcc atcatcggct ctggcgccag cacctactac   180
gccgacagcg tgaagggccg gttcaccatc agccgggaca acagcaagaa cacccctgtac   240 ctgcagatga acagcctgcg ggccgaggac accgccgtgt actactgcgc caagggatgg   300
ttcggcggct tcaactactg gggacagggc accctggtca cagtgtccag c          351

<210> SEQ ID NO 69
<211> LENGTH: 108
<212> TYPE: PRT
<213> ORGANISM: Artificial Sequence
<220> FEATURE:
<223> OTHER INFORMATION: 4B9; VL

<400> SEQUENCE: 69

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys
            100                 105

<210> SEQ ID NO 70
<211> LENGTH: 324
<212> TYPE: DNA
<213> ORGANISM: Artificial Sequence
<220> FEATURE:
<223> OTHER INFORMATION: 4B9; VL

<400> SEQUENCE: 70
gagatcgtgc tgacccagtc ccccggcacc ctgtctctga gccctggcga gagagccacc      60
ctgtcctgca gagcctccca gtccgtgacc tcctcctacc tcgcctggta tcagcagaag     120
cccggccagg cccctcggct gctgatcaac gtgggcagtc ggagagccac cggcatccct     180
gaccggttct ccggctctgg ctccggcacc gacttcaccc tgaccatctc ccggctggaa     240
cccgaggact tcgccgtgta ctactgccag cagggcatca tgctgccccc cacctttggc     300
cagggcacca aggtggaaat caag                                             324

<210> SEQ ID NO 71
<211> LENGTH: 116
<212> TYPE: PRT
<213> ORGANISM: Artificial Sequence
<220> FEATURE:
<223> OTHER INFORMATION: 28H1; VH

<400> SEQUENCE: 71

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Ala Met Ser Trp Val Arg Gln Ala Pro Gly Lys Gly Leu Glu Trp Val
        35                  40                  45

Ser Ala Ile Trp Ala Ser Gly Glu Gln Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

```
Gln Met Asn Ser Leu Arg Ala Glu Asp Thr Ala Val Tyr Tyr Cys Ala
                85                  90                  95

Lys Gly Trp Leu Gly Asn Phe Asp Tyr Trp Gly Gln Gly Thr Leu Val
            100                 105                 110

Thr Val Ser Ser
        115

<210> SEQ ID NO 72
<211> LENGTH: 348
<212> TYPE: DNA
<213> ORGANISM: Artificial Sequence
<220> FEATURE:
<223> OTHER INFORMATION: 28H1; VH

<400> SEQUENCE: 72
gaggtgcaat tgttggagtc tgggggaggc ttggtacagc ctggggggtc cctgagactc      60
tcctgtgcag cctccggatt cacctttagc agtcatgcta tgagctgggt ccgccaggct     120
ccagggaagg ggctggagtg ggtctcagct atttggggcta gtgggagca atactacgca     180 gactccgtga agggccggtt caccatctcc agagacaatt ccaagaacac gctgtatctg     240
cagatgaaca gcctgagagc cgaggacacg gccgtatatt actgtgcgaa agggtggctg     300
ggtaattttg actactgggg ccaaggaacc ctggtcaccg tctcgagt                  348

<210> SEQ ID NO 73
<211> LENGTH: 108
<212> TYPE: PRT
<213> ORGANISM: Artificial Sequence
<220> FEATURE:
<223> OTHER INFORMATION: 28H1; VL

<400> SEQUENCE: 73

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Ser
            20                  25                  30

Tyr Leu Ala Trp Tyr Gln Gln Lys Pro Gly Gln Ala Pro Arg Leu Leu
        35                  40                  45

Ile Ile Gly Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Val Ile Pro
                85                  90                  95

Pro Thr Phe Gly Gln Gly Thr Lys Val Glu Ile Lys
            100                 105

<210> SEQ ID NO 74
<211> LENGTH: 324
<212> TYPE: DNA
<213> ORGANISM: Artificial Sequence
<220> FEATURE:
<223> OTHER INFORMATION: 28H1; VL

<400> SEQUENCE: 74
gaaatcgtgt taacgcagtc tccaggcacc ctgtctttgt ctccagggga aagagccacc      60
ctctcttgca gggccagtca gagtgttagc cgcagctact tagcctggta ccagcagaaa     120
cctggccagg ctcccaggct cctcatcatt ggggcctcca ccagggccac tggcatccca     180
```

```
gacaggttca gtggcagtgg atccgggaca gacttcactc tcaccatcag cagactggag    240
cctgaagatt tgcagtgta ttactgtcag cagggtcagg ttattccccc tacgttcggc    300
caggggacca aagtggaaat caaa                                           324
```

<210> SEQ ID NO 75
<211> LENGTH: 117
<212> TYPE: PRT
<213> ORGANISM: Artificial Sequence
<220> FEATURE:
<223> OTHER INFORMATION: 3F2; VH

<400> SEQUENCE: 75

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
        115
```

<210> SEQ ID NO 76
<211> LENGTH: 351
<212> TYPE: DNA
<213> ORGANISM: Artificial Sequence
<220> FEATURE:
<223> OTHER INFORMATION: 3F2; VH

<400> SEQUENCE: 76

```
gaggtgcaat tgttggagtc tgggggaggc ttggtacagc ctggggggtc cctgagactc    60
tcctgtgcag cctccggatt caccttagc agttatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcagatga acagcctgag agccgaggac acggccgtat attactgtgc gaaaggtgg    300 tttggtggtt ttaactactg gggccaagga accctggtca ccgtctcgag t             351
```

<210> SEQ ID NO 77
<211> LENGTH: 108
<212> TYPE: PRT
<213> ORGANISM: Artificial Sequence
<220> FEATURE:
<223> OTHER INFORMATION: 3F2(YS); VL

<400> SEQUENCE: 77

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
```

```
                35                  40                  45
Ile Asn Val Gly Ser Arg Arg Ala Thr Gly Ile Pro Asp Arg Phe Ser
         50                  55                  60
Gly Ser Gly Ser Gly Thr Asp Phe Thr Leu Thr Ile Ser Arg Leu Glu
 65                  70                  75                  80
Pro Glu Asp Phe Ala Val Tyr Tyr Cys Gln Gln Gly Ile Met Leu Pro
                 85                  90                  95
Pro Thr Phe Gly Gln Gly Thr Lys Val Glu Ile Lys
             100                 105
```

<210> SEQ ID NO 78
<211> LENGTH: 324
<212> TYPE: DNA
<213> ORGANISM: Artificial Sequence
<220> FEATURE:
<223> OTHER INFORMATION: 3F2(YS); VL

<400> SEQUENCE: 78

```
gaaatcgtgt taacgcagtc tccaggcacc ctgtctttgt ctccagggga aagagccacc    60
ctctcttgca gggccagtca gagtgttacc agtagctact tagcctggta ccagcagaaa   120
cctggccagg ctcccaggct cctcatcaat gtgggctccc gtagggccac tggcatccca   180
gacaggttca gtggcagtgg atccgggaca gacttcactc tcaccatcag cagactggag   240
cctgaagatt ttgcagtgta ttactgtcag cagggtatta tgcttccccc gacgttcggc   300
caggggacca agtggaaat caaa                                           324
```

<210> SEQ ID NO 79
<211> LENGTH: 330
<212> TYPE: PRT
<213> ORGANISM: Homo sapiens

<400> SEQUENCE: 79

```
Ala Ser Thr Lys Gly Pro Ser Val Phe Pro Leu Ala Pro Ser Ser Lys
 1               5                  10                  15
Ser Thr Ser Gly Gly Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
             35                  40                  45
Gly Val His Thr Phe Pro Ala Val Leu Gln Ser Ser Gly Leu Tyr Ser
         50                  55                  60
Leu Ser Ser Val Val Thr Val Pro Ser Ser Leu Gly Thr Gln Thr
 65                  70                  75                  80
Tyr Ile Cys Asn Val Asn His Lys Pro Ser Asn Thr Lys Val Asp Lys
                 85                  90                  95
Lys Val Glu Pro Lys Ser Cys Asp Lys Thr His Thr Cys Pro Pro Cys
             100                 105                 110
Pro Ala Pro Glu Leu Leu Gly Gly Pro Ser Val Phe Leu Phe Pro Pro
         115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
             180                 185                 190
```

```
His Gln Asp Trp Leu Asn Gly Lys Glu Tyr Lys Cys Lys Val Ser Asn
            195                 200                 205
Lys Ala Leu Pro Ala Pro Ile Glu Lys Thr Ile Ser Lys Ala Lys Gly
        210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
            245                 250                 255
Pro Ser Asp Ile Ala Val Glu Trp Glu Ser Asn Gly Gln Pro Glu Asn
        260                 265                 270
Asn Tyr Lys Thr Thr Pro Pro Val Leu Asp Ser Asp Gly Ser Phe Phe
            275                 280                 285
Leu Tyr Ser Lys Leu Thr Val Asp Lys Ser Arg Trp Gln Gln Gly Asn
        290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
            325                 330

<210> SEQ ID NO 80
<211> LENGTH: 107
<212> TYPE: PRT
<213> ORGANISM: Homo sapiens

<400> SEQUENCE: 80

Arg Thr Val Ala Ala Pro Ser Val Phe Ile Phe Pro Pro Ser Asp Glu
1               5                   10                  15
Gln Leu Lys Ser Gly Thr Ala Ser Val Val Cys Leu Leu Asn Asn Phe
            20                  25                  30
Tyr Pro Arg Glu Ala Lys Val Gln Trp Lys Val Asp Asn Ala Leu Gln
        35                  40                  45
Ser Gly Asn Ser Gln Glu Ser Val Thr Glu Gln Asp Ser Lys Asp Ser
    50                  55                  60
Thr Tyr Ser Leu Ser Ser Thr Leu Thr Leu Ser Lys Ala Asp Tyr Glu
65                  70                  75                  80
Lys His Lys Val Tyr Ala Cys Glu Val Thr His Gln Gly Leu Ser Ser
                85                  90                  95
Pro Val Thr Lys Ser Phe Asn Arg Gly Glu Cys
            100                 105

<210> SEQ ID NO 81
<211> LENGTH: 748
<212> TYPE: PRT
<213> ORGANISM: Artificial Sequence
<220> FEATURE:
<223> OTHER INFORMATION: Human FAP ectodomain+poly-lys-tag+his6-tag

<400> SEQUENCE: 81

Arg Pro Ser Arg Val His Asn Ser Glu Glu Asn Thr Met Arg Ala Leu
1               5                   10                  15
Thr Leu Lys Asp Ile Leu Asn Gly Thr Phe Ser Tyr Lys Thr Phe Phe
            20                  25                  30
Pro Asn Trp Ile Ser Gly Gln Glu Tyr Leu His Gln Ser Ala Asp Asn
        35                  40                  45
Asn Ile Val Leu Tyr Asn Ile Glu Thr Gly Gln Ser Tyr Thr Ile Leu
    50                  55                  60
```

```
Ser Asn Arg Thr Met Lys Ser Val Asn Ala Ser Asn Tyr Gly Leu Ser
 65                  70                  75                  80

Pro Asp Arg Gln Phe Val Tyr Leu Glu Ser Asp Tyr Ser Lys Leu Trp
                 85                  90                  95

Arg Tyr Ser Tyr Thr Ala Thr Tyr Tyr Ile Tyr Asp Leu Ser Asn Gly
             100                 105                 110

Glu Phe Val Arg Gly Asn Glu Leu Pro Arg Pro Ile Gln Tyr Leu Cys
         115                 120                 125

Trp Ser Pro Val Gly Ser Lys Leu Ala Tyr Val Tyr Gln Asn Asn Ile
130                 135                 140

Tyr Leu Lys Gln Arg Pro Gly Asp Pro Pro Phe Gln Ile Thr Phe Asn
145                 150                 155                 160

Gly Arg Glu Asn Lys Ile Phe Asn Gly Ile Pro Asp Trp Val Tyr Glu
                 165                 170                 175

Glu Glu Met Leu Ala Thr Lys Tyr Ala Leu Trp Trp Ser Pro Asn Gly
             180                 185                 190

Lys Phe Leu Ala Tyr Ala Glu Phe Asn Asp Thr Asp Ile Pro Val Ile
         195                 200                 205

Ala Tyr Ser Tyr Tyr Gly Asp Glu Gln Tyr Pro Arg Thr Ile Asn Ile
210                 215                 220

Pro Tyr Pro Lys Ala Gly Ala Lys Asn Pro Val Val Arg Ile Phe Ile
225                 230                 235                 240

Ile Asp Thr Thr Tyr Pro Ala Tyr Val Gly Pro Gln Glu Val Pro Val
                 245                 250                 255

Pro Ala Met Ile Ala Ser Ser Asp Tyr Tyr Phe Ser Trp Leu Thr Trp
             260                 265                 270

Val Thr Asp Glu Arg Val Cys Leu Gln Trp Leu Lys Arg Val Gln Asn
         275                 280                 285

Val Ser Val Leu Ser Ile Cys Asp Phe Arg Glu Asp Trp Gln Thr Trp
290                 295                 300

Asp Cys Pro Lys Thr Gln Glu His Ile Glu Glu Ser Arg Thr Gly Trp
305                 310                 315                 320

Ala Gly Gly Phe Phe Val Ser Thr Pro Val Phe Ser Tyr Asp Ala Ile
                 325                 330                 335

Ser Tyr Tyr Lys Ile Phe Ser Asp Lys Asp Gly Tyr Lys His Ile His
             340                 345                 350

Tyr Ile Lys Asp Thr Val Glu Asn Ala Ile Gln Ile Thr Ser Gly Lys
         355                 360                 365

Trp Glu Ala Ile Asn Ile Phe Arg Val Thr Gln Asp Ser Leu Phe Tyr
370                 375                 380

Ser Ser Asn Glu Phe Glu Glu Tyr Pro Gly Arg Arg Asn Ile Tyr Arg
385                 390                 395                 400

Ile Ser Ile Gly Ser Tyr Pro Pro Ser Lys Lys Cys Val Thr Cys His
                 405                 410                 415

Leu Arg Lys Glu Arg Cys Gln Tyr Tyr Thr Ala Ser Phe Ser Asp Tyr
             420                 425                 430

Ala Lys Tyr Tyr Ala Leu Val Cys Tyr Gly Pro Gly Ile Pro Ile Ser
         435                 440                 445

Thr Leu His Asp Gly Arg Thr Asp Gln Glu Ile Lys Ile Leu Glu Glu
450                 455                 460

Asn Lys Glu Leu Glu Asn Ala Leu Lys Asn Ile Gln Leu Pro Lys Glu
465                 470                 475                 480

Glu Ile Lys Lys Leu Glu Val Asp Glu Ile Thr Leu Trp Tyr Lys Met
```

Ile Leu Pro Pro Gln Phe Asp Arg Ser Lys Lys Tyr Pro Leu Leu Ile
            500                 505                 510

Gln Val Tyr Gly Gly Pro Cys Ser Gln Ser Val Arg Ser Val Phe Ala
        515                 520                 525

Val Asn Trp Ile Ser Tyr Leu Ala Ser Lys Glu Gly Met Val Ile Ala
        530                 535                 540

Leu Val Asp Gly Arg Gly Thr Ala Phe Gln Gly Asp Lys Leu Leu Tyr
545                 550                 555                 560

Ala Val Tyr Arg Lys Leu Gly Val Tyr Glu Val Glu Asp Gln Ile Thr
                565                 570                 575

Ala Val Arg Lys Phe Ile Glu Met Gly Phe Ile Asp Glu Lys Arg Ile
            580                 585                 590

Ala Ile Trp Gly Trp Ser Tyr Gly Gly Tyr Val Ser Ser Leu Ala Leu
        595                 600                 605

Ala Ser Gly Thr Gly Leu Phe Lys Cys Gly Ile Ala Val Ala Pro Val
        610                 615                 620

Ser Ser Trp Glu Tyr Tyr Ala Ser Val Tyr Thr Glu Arg Phe Met Gly
625                 630                 635                 640

Leu Pro Thr Lys Asp Asp Asn Leu Glu His Tyr Lys Asn Ser Thr Val
                645                 650                 655

Met Ala Arg Ala Glu Tyr Phe Arg Asn Val Asp Tyr Leu Leu Ile His
            660                 665                 670

Gly Thr Ala Asp Asp Asn Val His Phe Gln Asn Ser Ala Gln Ile Ala
        675                 680                 685

Lys Ala Leu Val Asn Ala Gln Val Asp Phe Gln Ala Met Trp Tyr Ser
        690                 695                 700

Asp Gln Asn His Gly Leu Ser Gly Leu Ser Thr Asn His Leu Tyr Thr
705                 710                 715                 720

His Met Thr His Phe Leu Lys Gln Cys Phe Ser Leu Ser Asp Gly Lys
                725                 730                 735

Lys Lys Lys Lys Lys Gly His His His His His
            740                 745

<210> SEQ ID NO 82
<211> LENGTH: 2244
<212> TYPE: DNA
<213> ORGANISM: Artificial Sequence
<220> FEATURE:
<223> OTHER INFORMATION: Human FAP ectodomain+poly-lys-tag+his6-tag

<400> SEQUENCE: 82
cgcccttcaa gagttcataa ctctgaagaa aatacaatga gagcactcac actgaaggat      60
attttaaatg gaacattttc ttataaaaca ttttttccaa actggatttc aggacaagaa     120
tatcttcatc aatctgcaga taacaatata gtactttata atattgaaac aggacaatca     180
tataccattt tgagtaatag aaccatgaaa agtgtgaatg cttcaaatta cggcttatca     240
cctgatcggc aatttgtata tctagaaagt gattattcaa agctttggag atactcttac     300
acagcaacat attacatcta tgaccttagc aatggagaat ttgtaagagg aaatgagctt     360
cctcgtccaa ttcagtattt atgctggtcg cctgttggga gtaaattagc atatgtctat     420
caaaacaata tctatttgaa acaaagacca ggagatccac ttttcaat aacatttaat     480 ggaagagaaa ataaaatatt taatggaatc ccagactggg tttatgaaga ggaaatgctt     540
gctacaaaat atgctctctg gtggtctcct aatggaaaat tttggcata tgcggaattt     600

```
aatgatacgg atataccagt tattgcctat tcctattatg gcgatgaaca atatcctaga    660
acaataaata ttccataccc aaaggctgga gctaagaatc ccgttgttcg gatatttatt    720
atcgatacca cttaccctgc gtatgtaggt ccccaggaag tgcctgttcc agcaatgata    780
gcctcaagtg attattattt cagttggctc acgtgggtta ctgatgaacg agtatgtttg    840
cagtggctaa aaagagtcca gaatgtttcg gtcctgtcta tatgtgactt cagggaagac    900
tggcagacat gggattgtcc aaagacccag gagcatatag aagaaagcag aactggatgg    960
gctggtggat tctttgtttc aacaccagtt ttcagctatg atgccatttc gtactacaaa   1020
atatttagtg acaaggatgg ctacaaacat attcactata tcaaagacac tgtggaaaat   1080
gctattcaaa ttacaagtgg caagtgggag gccataaata tattcagagt aacacaggat   1140
tcactgtttt attctagcaa tgaatttgaa gaatacctg gaagaagaaa catctacaga    1200
attagcattg gaagctatcc tccaagcaag aagtgtgtta cttgccatct aaggaaagaa   1260
aggtgccaat attacacagc aagtttcagc gactacgcca agtactatgc acttgtctgc   1320
tacggcccag gcatccccat ttccacccct catgatggac gcactgatca agaaattaaa   1380
atcctggaag aaaacaagga attggaaaat gctttgaaaa atatccagct gcctaaagag   1440
gaaattaaga aacttgaagt agatgaaatt actttatggt acaagatgat tcttcctcct   1500
caatttgaca gatcaaagaa gtatcccttg ctaattcaag tgtatggtgg tccctgcagt   1560
cagagtgtaa ggtctgtatt tgctgttaat tggatatctt atcttgcaag taaggaaggg   1620
atggtcattg ccttggtgga tggtcgagga acagctttcc aaggtgacaa actcctctat   1680
gcagtgtatc gaaagctggg tgtttatgaa gttgaagacc agattacagc tgtcagaaaa   1740
ttcatagaaa tgggtttcat tgatgaaaaa agaatagcca tgggggctg gtcctatgga   1800 ggatacgttt catcactggc ccttgcatct ggaactggtc ttttcaaatg tggtatagca   1860
gtggctccag tctccagctg ggaatattac gcgtctgtct acacagagag attcatgggt   1920
ctcccaacaa aggatgataa tcttgagcac tataagaatt caactgtgat ggcaagagca   1980
gaatatttca gaaatgtaga ctatcttctc atccacggaa cagcagatga taatgtgcac   2040
tttcaaaact cagcacagat tgctaaagct ctggttaatg cacaagtgga tttccaggca   2100
atgtggtact ctgaccagaa ccacggctta tccggcctgt ccacgaacca cttatacacc   2160
cacatgaccc acttcctaaa gcagtgtttc tctttgtcag acggcaaaaa gaaaagaaa    2220 aagggccacc accatcacca tcac                                          2244
```

<210> SEQ ID NO 83
<211> LENGTH: 749
<212> TYPE: PRT
<213> ORGANISM: Artificial Sequence
<220> FEATURE:
<223> OTHER INFORMATION: Murine FAP ectodomain+poly-lys-tag+his6-tag

<400> SEQUENCE: 83

```
Arg Pro Ser Arg Val Tyr Lys Pro Glu Gly Asn Thr Lys Arg Ala Leu
1               5                   10                  15

Thr Leu Lys Asp Ile Leu Asn Gly Thr Phe Ser Tyr Lys Thr Tyr Phe
                20                  25                  30

Pro Asn Trp Ile Ser Glu Gln Glu Tyr Leu His Gln Ser Glu Asp Asp
            35                  40                  45

Asn Ile Val Phe Tyr Asn Ile Glu Thr Arg Glu Ser Tyr Ile Ile Leu
        50                  55                  60
```

```
Ser Asn Ser Thr Met Lys Ser Val Asn Ala Thr Asp Tyr Gly Leu Ser
 65                  70                  75                  80

Pro Asp Arg Gln Phe Val Tyr Leu Glu Ser Asp Tyr Ser Lys Leu Trp
                 85                  90                  95

Arg Tyr Ser Tyr Thr Ala Thr Tyr Tyr Ile Tyr Asp Leu Gln Asn Gly
                100                 105                 110

Glu Phe Val Arg Gly Tyr Glu Leu Pro Arg Pro Ile Gln Tyr Leu Cys
            115                 120                 125

Trp Ser Pro Val Gly Ser Lys Leu Ala Tyr Val Tyr Gln Asn Asn Ile
130                 135                 140

Tyr Leu Lys Gln Arg Pro Gly Asp Pro Pro Phe Gln Ile Thr Tyr Thr
145                 150                 155                 160

Gly Arg Glu Asn Arg Ile Phe Asn Gly Ile Pro Asp Trp Val Tyr Glu
                165                 170                 175

Glu Glu Met Leu Ala Thr Lys Tyr Ala Leu Trp Trp Ser Pro Asp Gly
            180                 185                 190

Lys Phe Leu Ala Tyr Val Glu Phe Asn Asp Ser Asp Ile Pro Ile Ile
            195                 200                 205

Ala Tyr Ser Tyr Tyr Gly Asp Gly Gln Tyr Pro Arg Thr Ile Asn Ile
210                 215                 220

Pro Tyr Pro Lys Ala Gly Ala Lys Asn Pro Val Val Arg Val Phe Ile
225                 230                 235                 240

Val Asp Thr Thr Tyr Pro His His Val Gly Pro Met Glu Val Pro Val
                245                 250                 255

Pro Glu Met Ile Ala Ser Ser Asp Tyr Tyr Phe Ser Trp Leu Thr Trp
            260                 265                 270

Val Ser Ser Glu Arg Val Cys Leu Gln Trp Leu Lys Arg Val Gln Asn
            275                 280                 285

Val Ser Val Leu Ser Ile Cys Asp Phe Arg Glu Asp Trp His Ala Trp
            290                 295                 300

Glu Cys Pro Lys Asn Gln Glu His Val Glu Glu Ser Arg Thr Gly Trp
305                 310                 315                 320

Ala Gly Gly Phe Phe Val Ser Thr Pro Ala Phe Ser Gln Asp Ala Thr
                325                 330                 335

Ser Tyr Tyr Lys Ile Phe Ser Asp Lys Asp Gly Tyr Lys His Ile His
                340                 345                 350

Tyr Ile Lys Asp Thr Val Glu Asn Ala Ile Gln Ile Thr Ser Gly Lys
            355                 360                 365

Trp Glu Ala Ile Tyr Ile Phe Arg Val Thr Gln Asp Ser Leu Phe Tyr
370                 375                 380

Ser Ser Asn Glu Phe Glu Gly Tyr Pro Gly Arg Arg Asn Ile Tyr Arg
385                 390                 395                 400

Ile Ser Ile Gly Asn Ser Pro Pro Ser Lys Lys Cys Val Thr Cys His
                405                 410                 415

Leu Arg Lys Glu Arg Cys Gln Tyr Tyr Thr Ala Ser Phe Ser Tyr Lys
            420                 425                 430

Ala Lys Tyr Tyr Ala Leu Val Cys Tyr Gly Pro Gly Leu Pro Ile Ser
            435                 440                 445

Thr Leu His Asp Gly Arg Thr Asp Gln Glu Ile Gln Val Leu Glu Glu
            450                 455                 460

Asn Lys Glu Leu Glu Asn Ser Leu Arg Asn Ile Gln Leu Pro Lys Val
465                 470                 475                 480

Glu Ile Lys Lys Leu Lys Asp Gly Gly Leu Thr Phe Trp Tyr Lys Met
```

```
                485                 490                 495
Ile Leu Pro Pro Gln Phe Asp Arg Ser Lys Lys Tyr Pro Leu Leu Ile
                500                 505                 510

Gln Val Tyr Gly Gly Pro Cys Ser Gln Ser Val Lys Ser Val Phe Ala
            515                 520                 525

Val Asn Trp Ile Thr Tyr Leu Ala Ser Lys Glu Gly Ile Val Ile Ala
        530                 535                 540

Leu Val Asp Gly Arg Gly Thr Ala Phe Gln Gly Asp Lys Phe Leu His
545                 550                 555                 560

Ala Val Tyr Arg Lys Leu Gly Val Tyr Glu Val Glu Asp Gln Leu Thr
                565                 570                 575

Ala Val Arg Lys Phe Ile Glu Met Gly Phe Ile Asp Glu Glu Arg Ile
                580                 585                 590

Ala Ile Trp Gly Trp Ser Tyr Gly Gly Tyr Val Ser Ser Leu Ala Leu
                595                 600                 605

Ala Ser Gly Thr Gly Leu Phe Lys Cys Gly Ile Ala Val Ala Pro Val
            610                 615                 620

Ser Ser Trp Glu Tyr Tyr Ala Ser Ile Tyr Ser Glu Arg Phe Met Gly
625                 630                 635                 640

Leu Pro Thr Lys Asp Asp Asn Leu Glu His Tyr Lys Asn Ser Thr Val
                645                 650                 655

Met Ala Arg Ala Glu Tyr Phe Arg Asn Val Asp Tyr Leu Leu Ile His
                660                 665                 670

Gly Thr Ala Asp Asp Asn Val His Phe Gln Asn Ser Ala Gln Ile Ala
            675                 680                 685

Lys Ala Leu Val Asn Ala Gln Val Asp Phe Gln Ala Met Trp Tyr Ser
        690                 695                 700

Asp Gln Asn His Gly Ile Leu Ser Gly Arg Ser Gln Asn His Leu Tyr
705                 710                 715                 720

Thr His Met Thr His Phe Leu Lys Gln Cys Phe Ser Leu Ser Asp Gly
                725                 730                 735

Lys Lys Lys Lys Lys Lys Gly His His His His His His
                740                 745
```

<210> SEQ ID NO 84
<211> LENGTH: 2247
<212> TYPE: DNA
<213> ORGANISM: Artificial Sequence
<220> FEATURE:
<223> OTHER INFORMATION: Murine FAP ectodomain+poly-lys-tag+his6-tag

<400> SEQUENCE: 84

```
cgtccctcaa gagtttacaa acctgaagga aacacaaaga gagctcttac cttgaaggat    60
attttaaatg gaacattctc atataaaaca tattttccca actggatttc agaacaagaa   120
tatcttcatc aatctgagga tgataacata gtatttatat atattgaaac aagagaatca   180
tatatcattt tgagtaatag caccatgaaa agtgtgaatg ctacagatta tggtttgtca   240
cctgatcggc aatttgtgta tctagaaagt gattattcaa agctctggcg atattcatac   300
acagcgacat actacatcta cgaccttcag aatggggaat tgtaagagg atacgagctc   360 cctcgtccaa ttcagtatct atgctggtcg cctgttggga gtaaattagc atatgtatat   420
caaaacaata tttatttgaa acaaagacca ggagatccac cttttcaaat aacttatact   480
ggaagagaaa atagaatatt taatggaata ccagactggg tttatgaaga ggaaatgctt   540
gccacaaaat atgctctttg gtggtctcca gatggaaaat ttttggcata tgtagaattt   600
```

```
aatgattcag atataccaat tattgcctat tcttattatg gtgatggaca gtatcctaga    660
actataaata ttccatatcc aaaggctggg gctaagaatc cggttgttcg tgtttttatt    720
gttgacacca cctaccctca ccacgtgggc ccaatggaag tgccagttcc agaaatgata    780
gcctcaagtg actattattt cagctggctc acatgggtgt ccagtgaacg agtatgcttg    840
cagtggctaa aaagagtgca gaatgtctca gtcctgtcta tatgtgattt cagggaagac    900
tggcatgcat gggaatgtcc aaagaaccag gagcatgtag aagaaagcag aacaggatgg    960
gctggtggat tctttgtttc gacaccagct tttagccagg atgccacttc ttactacaaa   1020
atatttagcg acaaggatgg ttacaaacat attcactaca tcaaagacac tgtggaaaat   1080
gctattcaaa ttacaagtgg caagtgggag gccatatata tattccgcgt aacacaggat   1140
tcactgtttt attctagcaa tgaatttgaa ggttaccctg aagaagaaa catctacaga   1200
attagcattg gaaactctcc tccgagcaag aagtgtgtta cttgccatct aaggaaagaa   1260
aggtgccaat attacacagc aagtttcagc tacaaagcca agtactatgc actcgtctgc   1320
tatggccctg gcctccccat ttccaccctc catgatggcc gcacagacca gaaatacaa   1380
gtattagaag aaaacaaaga actgaaaat tctctgagaa atatccagct gcctaaagtg   1440
gagattaaga agctcaaaga cgggggactg actttctggt acaagatgat tctgcctcct   1500
cagtttgaca gatcaaagaa gtacccttg ctaattcaag tgtatggtgg tccttgtagc   1560
cagagtgtta agtctgtgtt tgctgttaat tggataactt atctcgcaag taaggagggg   1620
atagtcattg ccctggtaga tggtcgggc actgctttcc aaggtgacaa attcctgcat   1680
gccgtgtatc gaaaactggg tgtatatgaa gttgaggacc agctcacagc tgtcagaaaa   1740
ttcatagaaa tggggtttcat tgatgaagaa agaatagcca tgggggctg gtcctacgga   1800
ggttatgttt catccctggc ccttgcatct ggaactggtc tttttcaaatg tggcatagca   1860
gtggctccag tctccagctg ggaatattac gcatctatct actcagagag attcatgggc   1920
ctcccaacaa aggacgacaa tctcgaacac tataaaatt caactgtgat ggcaagagca   1980
gaatatttca gaaatgtaga ctatcttctc atccacggaa cagcagatga taatgtgcac   2040
tttcagaact cagcacagat tgctaaagct ttggttaatg cacaagtgga tttccaggcg   2100
atgtggtact ctgaccagaa ccatggtata ttatctgggc gctcccagaa tcatttatat   2160
acccacatga cgcacttcct caagcaatgc ttttctttat cagacggcaa aagaaaaag   2220
aaaaagggcc accaccatca ccatcac                                       2247
```

<210> SEQ ID NO 85
<211> LENGTH: 748
<212> TYPE: PRT
<213> ORGANISM: Artificial Sequence
<220> FEATURE:
<223> OTHER INFORMATION: Cynomolgus FAP ectodomain+poly-lys-tag+his6-tag

<400> SEQUENCE: 85

Arg Pro Pro Arg Val His Asn Ser Glu Glu Asn Thr Met Arg Ala Leu
1               5                   10                  15

Thr Leu Lys Asp Ile Leu Asn Gly Thr Phe Ser Tyr Lys Thr Phe Phe
            20                  25                  30

Pro Asn Trp Ile Ser Gly Gln Glu Tyr Leu His Gln Ser Ala Asp Asn
        35                  40                  45

Asn Ile Val Leu Tyr Asn Ile Glu Thr Gly Gln Ser Tyr Thr Ile Leu
    50                  55                  60

```
Ser Asn Arg Thr Met Lys Ser Val Asn Ala Ser Asn Tyr Gly Leu Ser
 65                  70                  75                  80

Pro Asp Arg Gln Phe Val Tyr Leu Glu Ser Asp Tyr Ser Lys Leu Trp
                 85                  90                  95

Arg Tyr Ser Tyr Thr Ala Thr Tyr Tyr Ile Tyr Asp Leu Ser Asn Gly
            100                 105                 110

Glu Phe Val Arg Gly Asn Glu Leu Pro Arg Pro Ile Gln Tyr Leu Cys
        115                 120                 125

Trp Ser Pro Val Gly Ser Lys Leu Ala Tyr Val Tyr Gln Asn Asn Ile
    130                 135                 140

Tyr Leu Lys Gln Arg Pro Gly Asp Pro Pro Phe Gln Ile Thr Phe Asn
145                 150                 155                 160

Gly Arg Glu Asn Lys Ile Phe Asn Gly Ile Pro Asp Trp Val Tyr Glu
                165                 170                 175

Glu Glu Met Leu Ala Thr Lys Tyr Ala Leu Trp Trp Ser Pro Asn Gly
            180                 185                 190

Lys Phe Leu Ala Tyr Ala Glu Phe Asn Asp Thr Asp Ile Pro Val Ile
        195                 200                 205

Ala Tyr Ser Tyr Tyr Gly Asp Glu Gln Tyr Pro Arg Thr Ile Asn Ile
    210                 215                 220

Pro Tyr Pro Lys Ala Gly Ala Lys Asn Pro Phe Val Arg Ile Phe Ile
225                 230                 235                 240

Ile Asp Thr Thr Tyr Pro Ala Tyr Val Gly Pro Gln Glu Val Pro Val
                245                 250                 255

Pro Ala Met Ile Ala Ser Ser Asp Tyr Tyr Phe Ser Trp Leu Thr Trp
            260                 265                 270

Val Thr Asp Glu Arg Val Cys Leu Gln Trp Leu Lys Arg Val Gln Asn
        275                 280                 285

Val Ser Val Leu Ser Ile Cys Asp Phe Arg Glu Asp Trp Gln Thr Trp
    290                 295                 300

Asp Cys Pro Lys Thr Gln Glu His Ile Glu Glu Ser Arg Thr Gly Trp
305                 310                 315                 320

Ala Gly Gly Phe Phe Val Ser Thr Pro Val Phe Ser Tyr Asp Ala Ile
                325                 330                 335

Ser Tyr Tyr Lys Ile Phe Ser Asp Lys Asp Gly Tyr Lys His Ile His
            340                 345                 350

Tyr Ile Lys Asp Thr Val Glu Asn Ala Ile Gln Ile Thr Ser Gly Lys
        355                 360                 365

Trp Glu Ala Ile Asn Ile Phe Arg Val Thr Gln Asp Ser Leu Phe Tyr
    370                 375                 380

Ser Ser Asn Glu Phe Glu Asp Tyr Pro Gly Arg Arg Asn Ile Tyr Arg
385                 390                 395                 400

Ile Ser Ile Gly Ser Tyr Pro Pro Ser Lys Lys Cys Val Thr Cys His
                405                 410                 415

Leu Arg Lys Glu Arg Cys Gln Tyr Tyr Thr Ala Ser Phe Ser Asp Tyr
            420                 425                 430

Ala Lys Tyr Tyr Ala Leu Val Cys Tyr Gly Pro Gly Ile Pro Ile Ser
        435                 440                 445

Thr Leu His Asp Gly Arg Thr Asp Gln Glu Ile Lys Ile Leu Glu Glu
    450                 455                 460

Asn Lys Glu Leu Glu Asn Ala Leu Lys Asn Ile Gln Leu Pro Lys Glu
465                 470                 475                 480

Glu Ile Lys Lys Leu Glu Val Asp Glu Ile Thr Leu Trp Tyr Lys Met
```

```
                      485                 490                 495
Ile Leu Pro Pro Gln Phe Asp Arg Ser Lys Lys Tyr Pro Leu Leu Ile
                500                 505                 510

Gln Val Tyr Gly Gly Pro Cys Ser Gln Ser Val Arg Ser Val Phe Ala
            515                 520                 525

Val Asn Trp Ile Ser Tyr Leu Ala Ser Lys Glu Gly Met Val Ile Ala
        530                 535                 540

Leu Val Asp Gly Arg Gly Thr Ala Phe Gln Gly Asp Lys Leu Leu Tyr
545                 550                 555                 560

Ala Val Tyr Arg Lys Leu Gly Val Tyr Glu Val Glu Asp Gln Ile Thr
                565                 570                 575

Ala Val Arg Lys Phe Ile Glu Met Gly Phe Ile Asp Glu Lys Arg Ile
                580                 585                 590

Ala Ile Trp Gly Trp Ser Tyr Gly Gly Tyr Val Ser Ser Leu Ala Leu
                595                 600                 605

Ala Ser Gly Thr Gly Leu Phe Lys Cys Gly Ile Ala Val Ala Pro Val
            610                 615                 620

Ser Ser Trp Glu Tyr Tyr Ala Ser Val Tyr Thr Glu Arg Phe Met Gly
625                 630                 635                 640

Leu Pro Thr Lys Asp Asp Asn Leu Glu His Tyr Lys Asn Ser Thr Val
                645                 650                 655

Met Ala Arg Ala Glu Tyr Phe Arg Asn Val Asp Tyr Leu Leu Ile His
                660                 665                 670

Gly Thr Ala Asp Asp Asn Val His Phe Gln Asn Ser Ala Gln Ile Ala
            675                 680                 685

Lys Ala Leu Val Asn Ala Gln Val Asp Phe Gln Ala Met Trp Tyr Ser
        690                 695                 700

Asp Gln Asn His Gly Leu Ser Gly Leu Ser Thr Asn His Leu Tyr Thr
705                 710                 715                 720

His Met Thr His Phe Leu Lys Gln Cys Phe Ser Leu Ser Asp Gly Lys
                725                 730                 735

Lys Lys Lys Lys Lys Gly His His His His His
                740                 745
```

<210> SEQ ID NO 86
<211> LENGTH: 2244
<212> TYPE: DNA
<213> ORGANISM: Artificial Sequence
<220> FEATURE:
<223> OTHER INFORMATION: Cynomolgus FAP ectodomain+poly-lys-tag+his6-tag
      (DNA)

<400> SEQUENCE: 86

| | |
|---|---|
| cgccctccaa gagttcataa ctctgaagaa aatacaatga gagcactcac actgaaggat | 60 |
| atttaaatg ggacattttc ttataaaaca ttttttccaa actggatttc aggacaagaa | 120 |
| tatcttcatc aatctgcaga taacaatata gtactttata atattgaaac aggacaatca | 180 |
| ataccatttt tgagtaacag aaccatgaaa agtgtgaatg cttcaaatta tggcttatca | 240 |
| cctgatcggc aatttgtata tctagaaagt gattattcaa agctttggag atactcttac | 300 |
| acagcaacat attacatcta tgaccttagc aatggagaat tgtaagagg aaatgagctt | 360 |
| cctcgtccaa ttcagtattt atgctggtcg cctgttggga gtaaattagc atatgtctat | 420 |
| caaaacaata tctatttgaa acaaagacca ggagatccac cttttcaaat aacatttaat | 480 |
| ggaagagaaa ataaatatt taatggaatc ccagactggg tttatgaaga ggaaatgctt | 540 |

```
gctacaaaat atgctctctg gtggtctcct aatggaaaat ttttggcata tgcggaattt       600
aatgatacag atataccagt tattgcctat tcctattatg cgatgaaca atatcccaga       660 acaataaata ttccataccc aaaggccgga gctaagaatc cttttgttcg gatatttatt       720
atcgatacca cttaccctgc gtatgtaggt ccccaggaag tgcctgttcc agcaatgata       780
gcctcaagtg attattattt cagttggctc acgtgggtta ctgatgaacg agtatgtttg       840
cagtggctaa aaagagtcca gaatgtttcg gtcttgtcta tatgtgattt cagggaagac       900
tggcagacat gggattgtcc aaagacccag gagcatatag aagaaagcag aactggatgg       960
gctggtggat tctttgtttc aacaccagtt ttcagctatg atgccatttc atactacaaa      1020
atatttagtg acaaggatgg ctacaaacat attcactata tcaaagacac tgtggaaaat      1080
gctattcaaa ttacaagtgg caagtgggag gccataaata tattcagagt aacacaggat      1140
tcactgtttt attctagcaa tgaatttgaa gattaccctg aagaagaaa catctacaga      1200 attagcattg gaagctatcc tccaagcaag aagtgtgtta cttgccatct aaggaaagaa      1260
aggtgccaat attacacagc aagtttcagc gactacgcca agtactatgc acttgtctgc      1320
tatggcccag gcatccccat ttccacccctt catgacggac gcactgatca agaaattaaa      1380
atcctggaag aaaacaagga attggaaaat gctttgaaaa atatccagct gcctaaagag      1440
gaaattaaga aacttgaagt agatgaaatt actttatggt acaagatgat tcttcctcct      1500
caatttgaca gatcaaagaa gtatcccttg ctaattcaag tgtatggtgg tccctgcagt      1560
cagagtgtaa ggtctgtatt tgctgttaat tggatatctt atcttgcaag taaggaaggg      1620
atggtcattg ccttggtgga tggtcgggga acagctttcc aaggtgacaa actcctgtat      1680
gcagtgtatc gaaagctggg tgtttatgaa gttgaagacc agattacagc tgtcagaaaa      1740
ttcatagaaa tggtttcat tgatgaaaaa agaaatagcca tggggctg gtcctatgga      1800 ggatatgttt catcactggc ccttgcatct ggaactggtc ttttcaaatg tgggatagca      1860
gtggctccag tctccagctg gaatattac gcgtctgtct acacagagag attcatgggt      1920
ctcccaacaa aggatgataa tcttgagcac tataagaatt caactgtgat ggcaagagca      1980
gaatatttca gaaatgtaga ctatcttctc atccacggaa cagcagatga taatgtgcac      2040
tttcaaaact cagcacagat tgctaaagct ctggttaatg cacaagtgga tttccaggca      2100
atgtggtact ctgaccagaa ccacggctta tccggcctgt ccacgaacca cttatacacc      2160
cacatgaccc acttcctaaa gcagtgtttc tctttgtcag acggcaaaaa gaaaagaaa      2220 aagggccacc accatcacca tcac                                            2244
```

<210> SEQ ID NO 87
<211> LENGTH: 474
<212> TYPE: PRT
<213> ORGANISM: Artificial Sequence
<220> FEATURE:
<223> OTHER INFORMATION: Human IL-10R1-Fc fusion + Avi-tag

<400> SEQUENCE: 87

```
His Gly Thr Glu Leu Pro Ser Pro Pro Ser Val Trp Phe Glu Ala Glu
1               5                   10                  15

Phe Phe His His Ile Leu His Trp Thr Pro Ile Pro Asn Gln Ser Glu
            20                  25                  30

Ser Thr Cys Tyr Glu Val Ala Leu Leu Arg Tyr Gly Ile Glu Ser Trp
        35                  40                  45

Asn Ser Ile Ser Asn Cys Ser Gln Thr Leu Ser Tyr Asp Leu Thr Ala
    50                  55                  60
```

```
Val Thr Leu Asp Leu Tyr His Ser Asn Gly Tyr Arg Ala Arg Val Arg
 65                  70                  75                  80

Ala Val Asp Gly Ser Arg His Ser Asn Trp Thr Val Thr Asn Thr Arg
                 85                  90                  95

Phe Ser Val Asp Glu Val Thr Leu Thr Val Gly Ser Val Asn Leu Glu
            100                 105                 110

Ile His Asn Gly Phe Ile Leu Gly Lys Ile Gln Leu Pro Arg Pro Lys
        115                 120                 125

Met Ala Pro Ala Asn Asp Thr Tyr Glu Ser Ile Phe Ser His Phe Arg
130                 135                 140

Glu Tyr Glu Ile Ala Ile Arg Lys Val Pro Gly Asn Phe Thr Phe Thr
145                 150                 155                 160

His Lys Lys Val Lys His Glu Asn Phe Ser Leu Leu Thr Ser Gly Glu
                165                 170                 175

Val Gly Glu Phe Cys Val Gln Val Lys Pro Ser Val Ala Ser Arg Ser
            180                 185                 190

Asn Lys Gly Met Trp Ser Lys Glu Glu Cys Ile Ser Leu Thr Arg Gln
        195                 200                 205

Tyr Phe Thr Val Thr Asn Val Asp Glu Gln Leu Tyr Phe Gln Gly Gly
210                 215                 220

Ser Pro Lys Ser Ala Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Gly Ser Gly Gly Leu Asn Asp Ile
450                 455                 460

Phe Glu Ala Gln Lys Ile Glu Trp His Glu
465                 470
```

<210> SEQ ID NO 88
<211> LENGTH: 1422
<212> TYPE: DNA
<213> ORGANISM: Artificial Sequence
<220> FEATURE:
<223> OTHER INFORMATION: Human IL-10R1-Fc fusion + Avi-tag

<400> SEQUENCE: 88

```
catgggacag agctgcccag ccctccgtct gtgtggtttg aagcagaatt tttccaccac      60
atcctccact ggacacccat cccaaatcag tctgaaagta cctgctatga agtggcactc     120
ctgaggtatg aatagagtc ctggaactcc atctccaact gtagccagac cctgtcctat      180
gaccttaccg cagtgacctt ggacctgtac cacagcaatg gctaccgggc cagagtgcgg     240
gctgtggacg gcagccggca ctccaactgg accgtcacca cacccgcttc tctgtggat      300
gaagtgactc tgacagttgg cagtgtgaac ctagagatcc acaatggctt catcctcggg     360
aagattcagc tacccaggcc caagatggcc cccgcaaatg cacatatga aagcatcttc     420
agtcacttcc gagagtatga gattgccatt cgcaaggtgc cgggaaactt cacgttcaca     480
cacaagaaag taaaacatga aaacttcagc ctcctaacct ctggagaagt gggagagttc     540
tgtgtccagg tgaaaccatc tgtcgcttcc gaagtaaca aggggatgtg gtctaaagag      600
gagtgcatct ccctcaccag gcagtatttc accgtgacca acgtcgacga acagttatat     660
tttcagggcg gctcacccaa atctgcagac aaaactcaca catgcccacc gtgcccagca     720
cctgaactcc tgggggggacc gtcagtcttc ctcttccccc caaaaccaa ggacaccctc     780
atgatctccc ggaccctga ggtcacatgc gtggtggtgg acgtgagcca cgaagaccct      840
gaggtcaagt tcaactggta cgtggacggc gtggaggtgc ataatgccaa gacaaagccg     900
cgggaggagc agtacaacag cacgtaccgt gtggtcagcg tcctcaccgt cctgcaccag     960
gactggctga atggcaagga gtacaagtgc aaggtctcca acaaagccct cccagccccc    1020
atcgagaaaa ccatctccaa agccaaaggg cagccccgag aaccacaggt gtacaccctg    1080
cccccatccc gggatgagct gaccaagaac caggtcagcc tgacctgcct ggtcaaaggc    1140
ttctatccca gcgacatcgc cgtggagtgg gagagcaatg ggcagccgga gaacaactac    1200
aagaccacgc ctcccgtgct ggactccgac ggctccttct tcctctacag caagctcacc    1260
gtggacaaga gcaggtggca gcaggggaac gtcttctcat gctccgtgat gcatgaggct    1320
ctgcacaacc actacacgca gaagagcctc tccctgtctc cgggtggcgg gtccggaggc    1380
ctgaacgaca tcttcgaggc cagaagatt gaatggcacg ag                        1422
```

<210> SEQ ID NO 89
<211> LENGTH: 15
<212> TYPE: DNA
<213> ORGANISM: Artificial Sequence
<220> FEATURE:
<223> OTHER INFORMATION: HCDR Kabat (1)

<400> SEQUENCE: 89

```
agctacgcca tgagc                                                        15
```